United States Patent
Toledo-Sherman et al.

(10) Patent No.: US 9,884,853 B2
(45) Date of Patent: *Feb. 6, 2018

(54) KYNURENINE-3-MONOOXYGENASE INHIBITORS, PHARMACEUTICAL COMPOSITIONS, AND METHODS OF USE THEREOF

(71) Applicant: CHDI Foundation, Inc., New York, NY (US)

(72) Inventors: Leticia M. Toledo-Sherman, Santa Monica, CA (US); Celia Dominguez, Los Angeles, CA (US); Michael Prime, Abingdon (GB); William Mitchell, Market Rasen (GB); Naomi Went, Didcot (GB)

(73) Assignee: CHDI Foundation, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/392,304

(22) PCT Filed: Sep. 23, 2014

(86) PCT No.: PCT/US2014/056898
§ 371 (c)(1),
(2) Date: Dec. 23, 2015

(87) PCT Pub. No.: WO2015/047982
PCT Pub. Date: Apr. 2, 2015

(65) Prior Publication Data
US 2016/0257674 A1    Sep. 8, 2016

Related U.S. Application Data
(60) Provisional application No. 61/882,810, filed on Sep. 26, 2013.

(51) Int. Cl.
| | | |
|---|---|---|
| C07D 413/00 | (2006.01) | |
| C07D 263/00 | (2006.01) | |
| C07D 307/00 | (2006.01) | |
| C07D 277/60 | (2006.01) | |
| C07D 231/56 | (2006.01) | |
| C07D 209/04 | (2006.01) | |
| C07D 237/26 | (2006.01) | |
| C07D 239/72 | (2006.01) | |
| C07D 217/00 | (2006.01) | |
| C07D 215/00 | (2006.01) | |

(Continued)

(52) U.S. Cl.
CPC ......... *C07D 413/12* (2013.01); *C07D 209/08* (2013.01); *C07D 213/46* (2013.01); *C07D 215/18* (2013.01); *C07D 217/02* (2013.01); *C07D 231/56* (2013.01); *C07D 235/08* (2013.01); *C07D 237/28* (2013.01); *C07D 239/74* (2013.01); *C07D 241/42* (2013.01); *C07D 261/20* (2013.01); *C07D 263/56* (2013.01); *C07D 277/24* (2013.01); *C07D 277/64* (2013.01); *C07D 307/79* (2013.01); *C07D 319/18* (2013.01); *C07D 333/06* (2013.01); *C07D 333/10* (2013.01); *C07D 333/28* (2013.01); *C07D 407/12* (2013.01)

(58) Field of Classification Search
CPC .................................................... C07D 307/78
USPC .... 548/217, 229, 299, 152, 242, 362.5, 469; 549/434; 544/235, 283; 546/139, 152
See application file for complete search history.

(56) References Cited

U.S. PATENT DOCUMENTS

| | | |
|---|---|---|
| 4,474,785 A | 10/1984 | Rossy et al. |
| 4,772,598 A | 9/1988 | Geiss et al. |

(Continued)

FOREIGN PATENT DOCUMENTS

| | | |
|---|---|---|
| EP | 0068310 | 1/1983 |
| EP | 0293294 | 11/1988 |

(Continued)

OTHER PUBLICATIONS

Chemical Abstract, RN 27998-39-6, 1970.*

(Continued)

*Primary Examiner* — Shengjun Wang
(74) *Attorney, Agent, or Firm* — Sheppard Mullin Richter & Hampton LLP

(57) ABSTRACT

Certain compounds, or pharmaceutically acceptable salts or prodrugs thereof, are provided herein. Also provided are pharmaceutical compositions comprising at least one compound, or pharmaceutically acceptable salt or prodrug thereof, described herein and one or more pharmaceutically acceptable vehicle. Methods of treating patients suffering from certain diseases and disorders responsive to the inhibition of KMO activity are described, which comprise administering to such patients an amount of at least one compound, or pharmaceutically acceptable salt or prodrug thereof, described herein effective to reduce signs or symptoms of the disease or disorder are disclosed. These diseases include neurodegenerative disorders such as Huntington's disease. Also described are methods of treatment include administering at least one compound, or pharmaceutically acceptable salt or prodrug thereof, described herein as a single active agent or administering at least one compound, or pharmaceutically acceptable salt or prodrug thereof, described herein in combination with one or more other therapeutic agents. Also provided are methods for screening compounds capable of inhibiting KMO activity.

16 Claims, No Drawings

(51) Int. Cl.

| | | |
|---|---|---|
| *C07D 413/12* | (2006.01) | |
| *C07D 215/18* | (2006.01) | |
| *C07D 319/18* | (2006.01) | |
| *C07D 333/06* | (2006.01) | |
| *C07D 241/42* | (2006.01) | |
| *C07D 277/24* | (2006.01) | |
| *C07D 277/64* | (2006.01) | |
| *C07D 213/46* | (2006.01) | |
| *C07D 307/79* | (2006.01) | |
| *C07D 209/08* | (2006.01) | |
| *C07D 217/02* | (2006.01) | |
| *C07D 235/08* | (2006.01) | |
| *C07D 237/28* | (2006.01) | |
| *C07D 239/74* | (2006.01) | |
| *C07D 261/20* | (2006.01) | |
| *C07D 263/56* | (2006.01) | |
| *C07D 333/10* | (2006.01) | |
| *C07D 333/28* | (2006.01) | |
| *C07D 407/12* | (2006.01) | |

(56) References Cited

U.S. PATENT DOCUMENTS

| | | | |
|---|---|---|---|
| 6,133,302 A | 10/2000 | Pevarello et al. | |
| 2003/0139417 A1 | 7/2003 | Eberlein et al. | |
| 2004/0077616 A1 | 4/2004 | Bennani et al. | |
| 2005/0143422 A1 | 6/2005 | Levin et al. | |
| 2006/0116329 A1* | 6/2006 | Benatti | C07D 333/28 514/23 |
| 2011/0065681 A1 | 3/2011 | Wei et al. | |
| 2015/0057238 A1 | 2/2015 | Toledo-Sherman et al. | |
| 2016/0272611 A1 | 9/2016 | Dominguez et al. | |

FOREIGN PATENT DOCUMENTS

| | | |
|---|---|---|
| EP | 1424333 | 6/2004 |
| EP | 1475385 | 11/2004 |
| EP | 1628977 | 3/2006 |
| GB | 2230779 | 10/1990 |
| WO | WO 97/17316 | 5/1997 |
| WO | WO 98/40344 | 9/1998 |
| WO | WO 99/02506 | 1/1999 |
| WO | WO 02/079152 | 10/2002 |
| WO | WO 2006/013085 | 2/2006 |
| WO | WO2009/034029 A2 * | 3/2009 |
| WO | WO 2013/033085 | 3/2013 |
| WO | WO 2013/151707 | 10/2013 |

OTHER PUBLICATIONS

International Search Report and Written Opinion for PCT/US2014/056898 dated Feb. 19, 2015 (10 pages).
International Search Report and Written Opinion for PCT/US2014/056887 filed Sep. 23, 2014, dated Feb. 10, 2015 (10 pages).
International Search Report and Written Opinion for PCT/US13/31051 filed Mar. 13, 2013 dated May 21, 2013 (9 pages).
European Supplementary Search Report for EP 13772200.5 dated Feb. 2, 2016 (17 pages).
European Supplementary Search Report for EP 16186005 dated Dec. 9, 2016 (11 pages).
European Supplementary Search Report for EP 14847911 dated Jan. 13, 2017 (13 pages).
Search Report dated Sep. 4, 2015 and Written Opinion dated Jan. 19, 2016 for Singapore Application No. 11201406311U (10 pages).
Kunz et al., "Enantioselective Organocatalytic Cyclopropanations. The Identification of a New Class of Iminium Catalyst Based Upon Directed Electrostatic Activation," J. Am. Chem. Soc. 2005, vol. 127, No. 10, p. 3240-3241.
Lv et al., "Formal Diels—Alder Reactions of Chalcones and Formylcyclopropanes Catalyzed by Chiral N-Heterocyclic Carbenes," Organic Letters 2011, vol. 13, No. 19, p. 5366-5369.
Shibata et al., "Novel Michael Addition Promoted by Tributysltannylcarbamate. Synthesis of Diacylcyclopropanes", Tetrahedron Letters 1993, vol. 34, No. 41, p. 6567-6570.
National Center of Biotechnology Information, PubChem Compound Database; CID=23288293, https://pubchem.ncbi.nlm.nih.gov/compound/23288293 (Dec. 5, 2007).
CAS Registry No. 934085-92-4, which entered STN on May 2, 2007.
Database Registry[online], 2008, RN 1053729-71-7, 1017374-17-2, 1017351-31-3, 1017323-42-0, 1017216-35-1, 1017165-29-5, 1017112-16-1; Retrieved from STN international [online]; retrieved on Dec. 26, 2016.
Venkatesh et al. J. Org. Chem. 2002, 67, 9477-9480.
Patani et al. Chem. Rev. 1996, 96, 3147-3176.
Wohlfarth et al, First Metabolic Profile of XLR-11, A Novel Synthetic Cannabinoid, Obtained by Using Human Hepatocytes and High Resolution mass Spectrometry, Clinical Chemisty, vol. 59, No. 11, Sep. 6, 2013, 1638-1648.
Samet et al., "Preparation of chiral cyclopropanearboxylic acids and 3-oxabicyclo[3.1.0]hexane-2-ones from levoglucosenone," Tetrahedron Assymetry, pergamon Press LTD, Oxford, GB, vol. 19, No. 6, Apr. 2008, 691-694.
Database accession No. 1978:132116, Compound with RN: 27998-39-6 (Schmidt, Ulrich et al: "Cyclopropane compounds from ethyl phosphoenolpyruvate").
Database accession No. 2007:1177604, Compound with RN: 953066-35-8 (Ivashchenko, Alexander Vasilievich et al: "Azaheterocycles, combinatorial library, focused library, pharmaceutical composition and methods for their preparation from isonitriles, primary amines, and oxo-carboxylates or amino acid derivatives").
European Supplementary Search Report for EP 14848555 dated Mar. 20, 2017 (8 pages).

* cited by examiner

KYNURENINE-3-MONOOXYGENASE INHIBITORS, PHARMACEUTICAL COMPOSITIONS, AND METHODS OF USE THEREOF

This application claims the benefit of priority under 35 U.S.C. § 371 of PCT International Application No. PCT/US2014/056898, filed Sep. 23, 2014, which in turn claims the benefit of priority to U.S. Provisional Application No. 61/882,810, filed Sep. 26, 2013, both of which are incorporated herein by reference for all purposes.

Provided herein are certain kynurenine-3-monooxygenase inhibitors, pharmaceutical compositions thereof, and methods of their use.

Kynurenine-3-monooxygenase (KMO) is an enzyme in the tryptophan degradation pathway that catalyzes the conversion of kynurenine (KYN) into 3-hydroxykynurenine (3-HK or 3-OH-KYN), which is further degraded to the excitotoxic NMDA receptor agonist QUIN (3-hydroxyanthranilate oxygenase). 3-OH-KYN and QUIN act synergistically, i.e. 3-OH-KYN significantly potentiates the excitotoxic actions of QUIN. Studies from several laboratories have provided evidence that the shift of KYN pathway metabolism away from the 3-OH-KYN/QUIN branch to increase the formation of the neuroprotectant KYNA (kynurenic acid) in the brain leads to neuroprotection. In addition to having effects in the brain, the inhibition of KMO is further contemplated to impact peripheral tissues. Thus, the inhibition of KMO may be useful in the treatment of peripheral diseases as well as diseases of the brain. Furthermore, the relationship between KMO inhibition and elevations in AA (Anthranilic acid) could also have significant biological effects.

It has also been reported that KMO expression increases in inflammatory conditions or after immune stimulation. 3-OH-KYN, the product of its activity, accumulates in the brain of vitamin B-6 deficient neonatal rats and it causes cytotoxicity when added to neuronal cells in primary cultures or when locally injected into the brain. Recently, it was reported that relatively low concentrations (nanomolar) of 3-OH-KYN may cause apoptotic cell death of neurons in primary neuronal cultures. Structure-activity studies have in fact shown that 3-OH-KYN, and other o-amino phenols, may be subject to oxidative reactions initiated by their conversion to quinoneimines, a process associated with concomitant production of oxygen-derived free radicals. The involvement of these reactive species in the pathogenesis of ischemic neuronal death has been widely studied in the last several years and it has been shown that oxygen derived free radicals and glutamate mediated neurotransmission co-operate in the development of ischemic neuronal death.

It was also recently demonstrated that KMO activity is particularly elevated in the iris-ciliary body and that neoformed 3-OH-KYN is secreted into the fluid of the lens. An excessive accumulation of 3-OH-KYN in the lens may cause cataracts.

QUIN is an agonist of a subgroup of NMDA receptors and when directly injected into brain areas it destroys most neuronal cell bodies sparing fibers en passant and neuronal terminals. QUIN is a relatively poor agonist of the NMDA receptor complex containing either NR2C or NR2D subunits, while it interacts with relatively high affinity with the NMDA receptor complex containing NR2A and NR2B subunits. The neurotoxicity profile found after intrastriatal injection of QUIN resembles that found in the basal nuclei of Huntington's disease patients: while most of the intrinsic striatal neurons are destroyed, NADH-diaphorase-staining neurons (which are now considered able to express nitric oxide synthetase) and neurons containing neuropeptide Y seem to be spared together with axon terminals and fiber en passant.

In vivo-infusion of KYNA has shown to modulate synaptic release of critical neurotransmitters implicated in cognitive processes and affective mental faculties, such as acetylcholine (Ach), dopamine, and glutamate; therefore elevation of KYNA in brain can have effects in cognitive disorders and disorders arising from, or influenced by, changes in the levels of the neurotransmitters glutamate, dopamine, or Ach (such as Alzheimer's Disease, mild cognitive impairment (MCI), Parkinson's Disease (PD), schizophrenia, Huntington's Disease (HD), obsessive-compulsive disorder (OCD), and Tourette's Syndrome).

In vitro, the neurotoxic effects of the compound have been studied in different model systems with variable results: chronic exposure of organotypic cortico-striatal cultures to submicromolar concentration of QUIN causes histological signs of pathology, similar results have been obtained after chronic exposure of cultured neuronal cells.

In models of inflammatory neurological disorders such as experimental allergic encephalitis, bacterial and viral infections, forebrain global ischemia or spinal trauma, brain QUIN levels are extremely elevated. This increased brain QUIN concentration could be due to either an elevated circulating concentration of the excitotoxin or to an increased de novo synthesis in activated microglia or in infiltrating macrophages. In retrovirus-infected macaques, it has been proposed that most of the increased content of brain QUIN (approximately 98%) is due to local production. In fact, a robust increase in the activities of IDO (indoleamine 2,3-dioxygenase), KMO and kynureninase has been found in areas of brain inflammation.

Previous studies have shown that agents able to increase brain KYNA content cause sedation, mild analgesia, increase in the convulsive threshold, and neuroprotection against excitotoxic or ischemic damage. In addition to the above reported evidences, it has been recently demonstrated that a number of compounds able to increase brain KYNA formation may cause a robust decrease in glutamate (GLU) mediated neurotransmission by reducing GLU concentrations in brain extracellular spaces.

There remains a need for compounds that are effective inhibitors of KMO and may be used in treating neurodegenerative disorders.

Accordingly, provided is a compound of Formula I

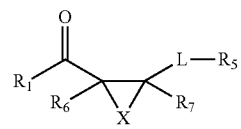

Formula I or a pharmaceutically acceptable salt or prodrug thereof, wherein
$R_1$ is optionally substituted heteroaryl;
X is —$CR_2R_3$—;
$R_2$ and $R_3$ are independently chosen from hydrogen, optionally substituted amino, hydroxyl, lower alkoxy, and optionally substituted lower alkyl;
L is —C(O)O—;
$R_5$ is hydrogen; and $R_6$ and $R_7$ are independently chosen from hydrogen, halo, optionally substituted amino, hydroxyl, lower alkoxy, and optionally substituted lower alkyl.

Also provided are prodrugs of a compound of Formula I.

Also provided is a pharmaceutical composition comprising at least one compound, or pharmaceutically acceptable salt or prodrug, described herein and at least one pharmaceutically acceptable excipient.

Also provided is a method of treating a condition or disorder mediated by Kynurenine 3-mono-oxygenase activity in a subject in need of such a treatment which method comprises administering to the subject a therapeutically effective amount of at least one compound, or pharmaceutically acceptable salt or prodrug described herein.

Also provided is a method of treating a condition or disorder mediated by Kynurenine 3-mono-oxygenase activity in a subject in need of such a treatment which method comprises administering to the subject a therapeutically effective amount of at least one compound, or pharmaceutically acceptable salt or prodrug, described herein.

Also provided is a packaged pharmaceutical composition comprising at least one pharmaceutical composition described herein and instructions for using the composition to treat a subject suffering from a condition or disorder mediated by Kynurenine 3-mono-oxygenase activity.

As used in the present specification, the following words, phrases and symbols are generally intended to have the meanings as set forth below, except to the extent that the context in which they are used indicates otherwise. The following abbreviations and terms have the indicated meanings throughout:

A dash ("-") that is not between two letters or symbols is used to indicate a point of attachment for a substituent. For example, —CONH$_2$ is attached through the carbon atom.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

"Alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is another subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having 1 to 4 carbons.

"Aryl" indicates an aromatic carbon ring having the indicated number of carbon atoms, for example, 6 to 12 or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring (e.g., cycloalkyl, cycloalkenyl, heterocycloalkyl, heterocycloalkenyl) fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl", as defined herein, regardless of the point of attachment (e.g., both quinolin-5-yl and quinolin-2-yl are heteroaryl groups). In some instances, aryl is phenyl or naphthyl. In certain instances, aryl is phenyl. Additional examples of aryl groups comprising an aromatic carbon ring fused to a non-aromatic ring are described below.

"Cycloalkyl" indicates a non-aromatic, fully saturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentyl, cyclopentenyl and cyclohexyl, as well as bridged and caged ring groups (e.g., norbornane, bicyclo[2.2.2]octane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group. Examples of polycyclic cycloalkyl groups consisting of a cycloalkyl group fused to an aromatic ring are described below.

"Cycloalkenyl" indicates a non-aromatic carbocyclic ring, containing the indicated number of carbon atoms (e.g., 3 to 10, or 3 to 8, or 3 to 6 ring carbon atoms) and at least one carbon-carbon double bond derived by the removal of one molecule of hydrogen from adjacent carbon atoms of the corresponding cycloalkyl. Cycloalkenyl groups may be monocyclic or polycyclic (e.g., bicyclic, tricyclic). Examples of cycloalkenyl groups include cyclopropenyl, cyclobutenyl, cyclopentenyl, cyclopentadienyl, and cyclohexenyl, as well as bridged and caged ring groups (e.g., bicyclo[2.2.2]octene). In addition, one ring of a polycyclic cycloalkenyl group may be aromatic, provided the polycyclic alkenyl group is bound to the parent structure via a non-aromatic carbon atom. For example, inden-1-yl (wherein the moiety is bound to the parent structure via a non-aromatic carbon atom) is considered a cycloalkenyl group, while inden-4-yl (wherein the moiety is bound to the parent structure via an aromatic carbon atom) is not considered a cycloalkenyl group. Examples of polycyclic cycloalkenyl groups consisting of a cycloalkenyl group fused to an aromatic ring are described below.

"Heteroaryl" indicates an aromatic ring containing the indicated number of atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups. When nitrogen is present in a heteroaryl ring, it may, where the nature of the adjacent atoms and groups permits, exist in an oxidized state (i.e., $N^+$—$O^-$). Additionally, when sulfur is present in a heteroaryl ring, it may, where the nature of the adjacent atoms and groups permits, exist in an oxidized state (i.e., $S^+$—$O^-$ or $SO_2$). Heteroaryl groups may be monocyclic or polycyclic (e.g., bicyclic, tricyclic).

In some instances, a heteroaryl group is monocyclic. Examples include pyrrole, pyrazole, imidazole, triazole (e.g., 1,2,3-triazole, 1,2,4-triazole, 1,2,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, both rings of a polycyclic heteroaryl group are aromatic. Examples include indole, isoindole, indazole, benzoimidazole, benzotriazole, benzofuran, benzoxazole, benzoisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H-[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group. Examples of polycyclic heteroaryl groups consisting of a heteroaryl ring fused to a non-aromatic ring are described below.

"Heterocycloalkyl" indicates a non-aromatic, fully saturated ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon. Heterocycloalkyl groups may be monocyclic or polycyclic (e.g., bicyclic, tricyclic). Examples of heterocycloalkyl groups include oxiranyl, aziridinyl, azetidinyl, pyrrolidinyl, imidazolidinyl, pyrazolidinyl, piperidinyl, piperazinyl, morpholinyl and thiomorpholinyl. When nitrogen is present in a heterocycloalkyl ring, it may, where the nature of the adjacent atoms and groups permits, exist in an oxidized state (i.e., $N^+$—$O^-$). Examples include piperidinyl N-oxide and morpholinyl-N-oxide. Additionally, when sulfur is present in a heterocycloalkyl ring, it may, where the nature of the adjacent atoms and groups permits, exist in an oxidized state (i.e., $S^+$—$O^-$ or —$SO_2$—). Examples include thiomorpholine S-oxide and thiomorpholine S,S-dioxide. In addition, one ring of a polycyclic heterocycloalkyl group may be aromatic (e.g., aryl or heteroaryl), provided the polycyclic heterocycloalkyl group is bound to the parent structure via a non-aromatic carbon or nitrogen atom. For example, a 1,2,3,4-tetrahydroquinolin-1-yl group (wherein the moiety is bound to the parent structure via a non-aromatic nitrogen atom) is considered a heterocycloalkyl group, while 1,2,3,4-tetrahydroquinolin-8-yl group (wherein the moiety is bound to the parent structure via an aromatic carbon atom) is not considered a heterocycloalkyl group. Examples of polycyclic heterocycloalkyl groups consisting of a heterocycloalkyl group fused to an aromatic ring are described below.

"Heterocycloalkenyl" indicates a non-aromatic ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon, and at least one double bond derived by the removal of one molecule of hydrogen from adjacent carbon atoms, adjacent nitrogen atoms, or adjacent carbon and nitrogen atoms of the corresponding heterocycloalkyl. Heterocycloalkenyl groups may be monocyclic or polycyclic (e.g., bicyclic, tricyclic). When nitrogen is present in a heterocycloalkenyl ring, it may, where the nature of the adjacent atoms and groups permits, exist in an oxidized state (i.e., $N^+$—$O^-$). Additionally, when sulfur is present in a heterocycloalkenyl ring, it may, where the nature of the adjacent atoms and groups permits, exist in an oxidized state (i.e., $S^+$—$O^-$ or —$SO_2$—). Examples of heterocycloalkenyl groups include dihydrofuranyl (e.g., 2,3-dihydrofuranyl, 2,5-dihydrofuranyl), dihydrothiophenyl (e.g., 2,3-dihydrothiophenyl, 2,5-dihydrothiophenyl), dihydropyrrolyl (e.g., 2,3-dihydro-1H-pyrrolyl, 2,5-dihydro-1H-pyrrolyl), dihydroimidazolyl (e.g., 2,3-dihydro-1H-imidazolyl, 4,5-dihydro-1H-imidazolyl), pyranyl, dihydropyranyl (e.g., 3,4-dihydro-2H-pyranyl, 3,6-dihydro- 2H-pyranyl), tetrahydropyridinyl (e.g., 1,2,3,4-tetrahydropyridinyl, 1,2,3,6-tetrahydropyridinyl) and dihydropyridine (e.g., 1,2-dihydropyridine, 1,4-dihydropyridine). In addition, one ring of a polycyclic heterocycloalkenyl group may be aromatic (e.g., aryl or heteroaryl), provided the polycyclic heterocycloalkenyl group is bound to the parent structure via a non-aromatic carbon or nitrogen atom. For example, a 1,2-dihydroquinolin-1-yl group (wherein the moiety is bound to the parent structure via a non-aromatic nitrogen atom) is considered a heterocycloalkenyl group, while 1,2-dihydroquinolin-8-yl group (wherein the moiety is bound to the parent structure via an aromatic carbon atom) is not considered a heterocycloalkenyl group. Examples of polycyclic heterocycloalkenyl groups consisting of a heterocycloalkenyl group fused to an aromatic ring are described below.

Examples of polycyclic rings consisting of an aromatic ring (e.g., aryl or heteroaryl) fused to a non-aromatic ring (e.g., cycloalkyl, cycloalkenyl, heterocycloalkyl, heterocycloalkenyl) include indenyl, 2,3-dihydro-1H-indenyl, 1,2,3,4-tetrahydronaphthalenyl, benzo[1,3]dioxolyl, tetrahydroquinolinyl, 2,3-dihydrobenzo[1,4]dioxinyl, indolinyl, isoindolinyl, 2,3-dihydro-1H-indazolyl, 2,3-dihydro-1H-benzo[d]imidazolyl, 2,3-dihydrobenzofuranyl, 1,3-dihydroisobenzofuranyl, 1,3-dihydrobenzo[c]isoxazolyl, 2,3-dihydrobenzo[d]isoxazolyl, 2,3-dihydrobenzo[d]oxazolyl, 2,3-dihydrobenzo[b]thiophenyl, 1,3-dihydrobenzo[c]thiophenyl, 1,3-dihydrobenzo[c]isothiazolyl, 2,3-dihydrobenzo[d]isothiazolyl, 2,3-dihydrobenzo[d]thiazolyl, 5,6-dihydro-4H-cyclopenta[d]thiazolyl, 4,5,6,7-tetrahydrobenzo[d]thiazolyl, 5,6-dihydro-4H-pyrrolo[3,4-d]thiazolyl, 4,5,6,7-tetrahydrothiazolo[5,4-c]pyridinyl, indolin-2-one, indolin-3-one, isoindolin-1-one, 1,2-dihydroindazol-3-one, 1H-benzo[d]imidazol-2(3H)-one, benzofuran-2(3H)-one, benzofuran-3(2H)-one, isobenzofuran-1(3H)-one, benzo[c]isoxazol-3(1H)-one, benzo[d]isoxazol-3(2H)-one, benzo[d]oxazol-2(3H)-one, benzo[b]thiophen-2(3H)-one, benzo[b]thiophen-3(2H)-one, benzo[c]thiophen-1(3H)-one, benzo[c]isothiazol-3(1H)-one, benzo[d]isothiazol-3(2H)-one, benzo[d]thiazol-2(3H)-one, 4,5-dihydropyrrolo[3,4-d]thiazol-6-one, 1,2-dihydropyrazolo[3,4-d]thiazol-3-one, quinolin-4(3H)-one, quinazolin-4(3H)-one, quinazoline-2,4(1H,3H)-dione, quinoxalin-2(1H)-one, quinoxaline-2,3(1H,4H)-dione, cinnolin-4(3H)-one, pyridin-2(1H)-one, pyrimidin-2(1H)-one, pyrimidin-4(3H)-one, pyridazin-3(2H)-one, 1H-pyrrolo[3,2-b]pyridin-2(3H)-one, 1H-pyrrolo[3,2-c]pyridin-2(3H)-one, 1H-pyrrolo[2,3-c]pyridin-2(3H)-one, 1H-pyrrolo[2,3-b]pyridin-2(3H)-one, 1,2-dihydropyrazolo[3,4-d]thiazol-3-one and 4,5-dihydropyrrolo[3,4-d]thiazol-6-one. As discussed herein, whether each ring is considered an aryl, heteroaryl, cycloalkyl, cycloalkenyl, heterocycloalkyl or heterocycloalkenyl group is determined by the atom through which the moiety is bound to the parent structure.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. An alkoxy group is further meant to encompass a cycloalkyl group, as defined above, that is likewise attached through an oxygen bridge. Alkoxy groups will usually have from 1 to 6 carbon atoms attached through the oxygen bridge. "Lower alkoxy" refers to alkoxy groups having 1 to 4 carbons.

The term "halo" includes fluoro, chloro, bromo, and iodo, and the term "halogen" includes fluorine, chlorine, bromine, and iodine.

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl (including without limitation lower alkyl), cycloalkyl, aryl (including without limitation phenyl), heterocycloalkyl (including without limitation morpholin-4-yl, 3,4-dihydroquinolin-1(2H)-yl, indolin-1-yl, 3-oxopiperazin-1-yl, piperidin-1-yl, piperazin-1-yl, pyrrolidin-1-yl, azetidin-1-yl, and isoindolin-2-yl), and heteroaryl (including without limitation pyridinyl), unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently chosen from:

—$R^a$, —$OR^b$, —O($C_1$-$C_2$ alkyl)O— (e.g., methylenedioxy-), —$SR^b$, guanidine, guanidine wherein one or more of the guanidine hydrogens are replaced with a lower-alkyl group, —$NR^bR^c$, halo, cyano, oxo (as a substituent for heterocycloalkyl), nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$SOR^a$, —$SO_2R^a$, —$SO_2NR^bR^c$, and —$NR^cSO_2R^a$, where $R^a$ is chosen from optionally substituted $C_1$-$C_6$ alkyl, optionally substituted cycloalkyl, optionally substituted aryl, optionally substituted heterocycloalkyl, and optionally substituted heteroaryl;

$R^b$ is chosen from H, optionally substituted $C_1$-$C_6$ alkyl, optionally substituted cycloalkyl, optionally substituted aryl, optionally substituted heterocycloalkyl, and optionally substituted heteroaryl; and $R^c$ is chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, cycloalkyl, aryl, heterocycloalkyl, heteroaryl, aryl-$C_1$-$C_4$ alkyl-, heteroaryl-$C_1$-$C_4$ alkyl-, $C_1$-$C_4$ haloalkyl-, —O$C_1$-$C_4$ alkyl, —O$C_1$-$C_4$ alkylphenyl, —$C_1$-$C_4$ alkyl-OH, —$C_1$-$C_4$ alkyl-O—$C_1$-$C_4$ alkyl, —O$C_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$ ($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl).

The term "substituted alkoxy" refers to alkoxy wherein the alkyl constituent is substituted (i.e., —O-(substituted alkyl)) wherein "substitutedalkyl" is as described herein. "Substituted alkoxy" also includes glycosides (i.e., glycosyl groups) and derivatives of ascorbic acid.

The term "substituted amino" refers to the group —$NHR^d$ or —$NR^dR^d$ where each $R^d$ is independently chosen from: hydroxy, optionally substituted alkyl, optionally substituted cycloalkyl, optionally substituted acyl, aminocarbonyl, optionally substituted aryl, optionally substituted heteroaryl, optionally substituted heterocycloalkyl, optionally substituted alkoxycarbonyl, sulfinyl and sulfonyl, each as described herein, and provided that only one $R^d$ may be hydroxyl. The term "substituted amino" also refers to N-oxides of the groups —$NHR^d$, and $NR^dR^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

"Aminocarbonyl" encompasses a group of the formula —(C=O)(optionally substituted amino) wherein substituted amino is as described herein.

"Acyl" refers to the groups (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a $C_2$ acyl group is an acetyl group having the formula $CH_3$(C=O)—.

By "alkoxycarbonyl" is meant an ester group of the formula (alkoxy)(C=O)-attached through the carbonyl carbon wherein the alkoxy group has the indicated number of carbon atoms. Thus a $C_1$-$C_6$alkoxycarbonyl group is an alkoxy group having from 1 to 6 carbon atoms attached through its oxygen to a carbonyl linker.

By "amino" is meant the group —$NH_2$.

The term "sulfinyl" includes the groups: —S(O)-(optionally substituted ($C_1$-$C_6$)alkyl), —S(O)-optionally substituted aryl), —S(O)-optionally substituted heteroaryl), —S(O)-(optionally substituted heterocycloalkyl); and —S(O)-(optionally substituted amino).

The term "sulfonyl" includes the groups —$S(O_2)$-(optionally substituted ($C_1$-$C_6$)alkyl), —$S(O_2)$-optionally substituted aryl), —$S(O_2)$-optionally substituted heteroaryl), —$S(O_2)$-(optionally substituted heterocycloalkyl), —$S(O_2)$-(optionally substituted alkoxy), —$S(O_2)$-optionally substituted aryloxy), —$S(O_2)$-optionally substituted heteroaryloxy), —$S(O_2)$-(optionally substituted heterocyclyloxy); and —$S(O_2)$-(optionally substituted amino).

The term "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl are as described herein.

The term "substituted alkoxycarbonyl" refers to the group (substituted alkyl)-O—C(O)— wherein the group is attached to the parent structure through the carbonyl functionality and wherein substituted alkyl is as described herein.

"Glycosides" refer to any of a number of sugar derivatives that contain a non-sugar group bonded to an oxygen or nitrogen atom of a sugar and that on hydrolysis yield that sugar. An example of a glycosyl group is glucosyl.

"Derivatives of ascorbic acid" or "ascorbic acid derivatives" refer to any of a number of derivatives that contain a non-sugar group bonded to an oxygen or nitrogen atom of ascorbic acid and that on hydrolysis yield ascorbic acid (i.e., (R)-5-((S)-1,2-dihydroxyethyl)-3,4-dihydroxyfuran-2(5H)-one).

"Isomers" are different compounds that have the same molecular formula. "Stereoisomers" are isomers that differ only in the way the atoms are arranged in space. "Enantiomers" are stereoisomers that are non-superimposable mirror images of each other. A 1:1 mixture of a pair of enantiomers is a "racemic" mixture. The symbol "(±)" may be used to designate a racemic mixture where appropriate. "Diastereoisomers" are stereoisomers that have at least two asymmetric atoms, but which are not mirror-images of each other. A "meso compound" or "meso isomer" is a non-optically active member of a set of stereoisomers. Meso isomers contain two or more stereocenters but are not chiral (i.e., a plane of symmetry exists within the molecule). The absolute stereochemistry is specified according to the Cahn-Ingold-Prelog R-S system. When a compound is a pure enantiomer the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds disclosed and/or described herein contain one or more asymmetric centers and can thus give rise to enantiomers, diastereomers, meso isomers and other stereoisomeric forms. Unless otherwise indicated, compounds disclosed and/or described herein include all such possible enantiomers, diastereomers, meso isomers and other stereoisomeric forms, including racemic mixtures, optically pure forms and intermediate mixtures. Enantiomers, diastereomers, meso isomers and other stereoisomeric formscan be prepared using chiral synthons or chiral reagents, or resolved using conventional techniques. Unless specified otherwise, when the compounds disclosed and/or described herein contain olefinic double bonds or other centers of geometric asymmetry, it is intended that the compounds include both E and Z isomers.

"Tautomers" are structurally distinct isomers that interconvert by tautomerization. Tautomerization is a form of isomerization and includes prototropic or proton-shift tautomerization, which is considered a subset of acid-base chemistry. Prototropic tautomerization or proton-shift tautomerization involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers. When the compounds described herein contain moieties capable of tautomerization, and unless specified otherwise, it is intended that the compounds include all possible tautomers.

Pharmaceutically acceptable forms of the compounds recited herein include pharmaceutically acceptable salts, prodrugs, and mixtures thereof. In some embodiments, the compounds described herein are in the form of pharmaceutically acceptable salts and prodrugs.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—$(CH_2)_n$—COOH where n is 0-4, and like salts. Similarly, pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

The term "prodrug" refers to a substance administered in an inactive or less active form that is then transformed (e.g., by metabolic processing of the prodrug in the body) into an active compound. The rationale behind administering a prodrug is to optimize absorption, distribution, metabolism, and/or excretion of the drug. Prodrugs may be obtained by making a derivative of an active compound (e.g., a compound of Formula I or another compound disclosed and/or described herein) that will undergo a transformation under the conditions of use (e.g., within the body) to form the active compound. The transformation of the prodrug to the active compound may proceed spontaneously (e.g., by way of a hydrolysis reaction) or it can be catalyzed or induced by another agent (e.g., an enzyme, light, acid or base, and/or temperature). The agent may be endogenous to the conditions of use (e.g., an enzyme present in the cells to which the prodrug is administered, or the acidic conditions of the stomach) or the agent may be supplied exogenously. Prodrugs can be obtained by converting one or more functional groups in the active compound into another functional group, which is then converted back to the original functional group when administered to the body. For example, a hydroxyl functional group can be converted to a sulfonate, phosphate, ester or carbonate group, which in turn can be hydrolyzed in vivo back to the hydroxyl group. Similarly, an amino functional group can be converted, for example, into an amide, carbamate, imine, urea, phosphenyl, phosphoryl or sulfenyl functional group, which can be hydrolyzed in vivo back to the amino group. A carboxyl functional group can be converted, for example, into an ester (including silyl esters and thioesters), amide or hydrazide functional group, which can be hydrolyzed in vivo back to the carboxyl group. Examples of prodrugs include, but are not limited to, phosphate, acetate, formate and benzoate derivatives of functional groups (such as alcohol or amine groups) present in the compounds of Formula I and other compounds disclosed and/or described herein.

The compounds disclosed and/or described herein can be enriched isotopic forms, e.g., enriched in the content of $^2H$, $^3H$, $^{11}C$, $^{13}C$ and/or $^{14}C$. In one embodiment, the compound contains at least one deuterium atom. Such deuterated forms can be made, for example, by the procedure described in U.S. Pat. Nos. 5,846,514 and 6,334,997. Such deuterated compounds may improve the efficacy and increase the duration of action of compounds disclosed and/or described herein. Deuterium substituted compounds can be synthesized using various methods, such as those described in: Dean, D., Recent Advances in the Synthesis and Applications of Radiolabeled Compounds for Drug Discovery and Development, *Curr. Pharm. Des.*, 2000; 6(10); Kabalka, G. et al., The Synthesis of Radiolabeled Compounds via Organometallic Intermediates, *Tetrahedron*, 1989, 45(21), 6601-21; and Evans, E., Synthesis of radiolabeled compounds, *J. Radioanal. Chem.*, 1981, 64(1-2), 9-32.

A "solvate" is formed by the interaction of a solvent and a compound. The term "compound" is intended to include solvates of compounds. Similarly, "salts" includes solvates of salts. Suitable solvates are pharmaceutically acceptable solvates, such as hydrates, including monohydrates and hemi-hydrates.

A "chelate" is formed by the coordination of a compound to a metal ion at two (or more) points. The term "compound" is intended to include chelates of compounds. Similarly, "salts" includes chelates of salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound".

The term "hydrogen bond" refers to a form of association between an electronegative atom (also known as a hydrogen bond acceptor) and a hydrogen atom attached to a second, relatively electronegative atom (also known as a hydrogen bond donor). Suitable hydrogen bond donor and acceptors are well understood in medicinal chemistry (G. C. Pimentel and A. L. McClellan, The Hydrogen Bond, Freeman, San Francisco, 1960; R. Taylor and O. Kennard, "Hydrogen Bond Geometry in Organic Crystals", Accounts of Chemical Research, 17, pp. 320-326 (1984)).

"Hydrogen bond acceptor" refers to a group comprising an oxygen or nitrogen, such as an oxygen or nitrogen that is $sp^2$-hybridized, an ether oxygen, or the oxygen of a sulfoxide or N-oxide.

The term "hydrogen bond donor" refers to an oxygen, nitrogen, or heteroaromatic carbon that bears a hydrogen. group containing a ring nitrogen or a heteroaryl group containing a ring nitrogen.

As used herein the terms "group", "radical" or "fragment" are synonymous and are intended to indicate functional groups or fragments of molecules attachable to a bond or other fragments of molecules.

The term "active agent" is used to indicate a substance which has biological activity. In some embodiments, an "active agent" is a substance having pharmaceutical utility. For example an active agent may be an anti-neurodegenerative therapeutic.

The term "therapeutically effective amount" means an amount effective, when administered to a human or non-human subject, to provide a therapeutic benefit such as amelioration of symptoms, slowing of disease progression, or prevention of disease e.g., a therapeutically effective amount may be an amount sufficient to decrease the symptoms of a disease responsive to inhibition of KMO activity and modulation of kynurenine pathway metabolites (such as kynurenine, kynurenic acid, anthranilic acid, 3-OH-kynurenine, 3-OH anthranilic acid, or quinolinic acid). In some embodiments, a therapeutically effective amount is an amount sufficient to treat the symptoms of neurodegenerative pathway or disease. In some embodiments a therapeutically effective amount is an amount sufficient to reduce the signs or side effects of a neurodegenerative disease. In some embodiments, a therapeutically effective amount is an amount sufficient to prevent a significant increase or significantly reduce the level of neuronal cell death. In some embodiments, a therapeutically effective amount entity is an amount sufficient to prevent a significant increase or significantly reduce the level of QUIN associated with neuronal cell death. In some embodiments, a therapeutically effective amount is an amount sufficient to effect an increase in the level of KYNA associated with neuronal cell health. In some embodiments, a therapeutically effective amount is an amount sufficient to increase the anticonvulsant and neuroprotective properties associated with lowered levels of QUIN and increased levels of KYNA. In some embodiments, a therapeutically effective amount is an amount sufficient to modulate an inflammatory process in the body, including but not limited to inflammation in the brain, spinal cord, and peripheral nervous system, or meninges. In some embodiments, a therapeutically effective amount is an amount sufficient to modulate the production of cytokines responsible for mounting an effective immune response (such as IL-1 beta or TNF-alpha) or an amount sufficient to affect monocyte/macrophage pro-inflammatory activity in the periphery or in the brain in conditions where the blood-brain barrier is compromised, such as in multiple sclerosis).

In methods described herein for treating a neurodegenerative disorder, a therapeutically effective amount may also be an amount sufficient, when administered to a patient, to detectably slow the progression of the neurodegenerative disease, or prevent the patient to whom the at least one compound, or pharmaceutically acceptable salt or prodrug thereof, described herein is given from presenting symptoms of the neurodegenerative disease. In some methods described herein for treating a neurodegenerative disease, a therapeutically effective amount may also be an amount sufficient to produce a detectable decrease in the level of neuronal cell death. For example, in some embodiments a therapeutically effective amount is an amount sufficient to significantly decrease the level of neuronal death by effecting a detectable decrease in the amount of QUIN, and an increase in the amount of kynurenine, KYNA, or anthranilic acid.

In addition, an amount is considered to be a therapeutically effective amount if it is characterized as such by at least one of the above criteria or experimental conditions, regardless of any inconsistent or contradictory results under a different set of criteria or experimental conditions.

The term "inhibition" indicates a significant decrease in the baseline activity of a biological activity or process. "Inhibition of KMO activity" refers to a decrease in KMO activity as a direct or indirect response to the presence of at least one compound, or pharmaceutically acceptable salt or prodrug thereof, described herein, relative to the activity of KMO in the absence of the at least one compound, or pharmaceutically acceptable salt or prodrug thereof, described herein. The decrease in activity may be due to the direct interaction of the at least one compound, or pharmaceutically acceptable salt or prodrug thereof, described herein with KMO, or due to the interaction of the at least one compound, or pharmaceutically acceptable salt or prodrug thereof, described herein with one or more other factors that in turn affect KMO activity. For example, the presence of the at least one compound, or pharmaceutically acceptable salt or prodrug thereof, described herein may decrease KMO activity by directly binding to the KMO, by causing (directly or indirectly) another factor to decrease KMO activity, or by (directly or indirectly) decreasing the amount of KMO present in the cell or organism.

"Inhibition of KMO activity" refers to a decrease in KMO activity as a direct or indirect response to the presence of at least one compound, or pharmaceutically acceptable salt or prodrug thereof, described herein, relative to the activity of KMO in the absence of the at least one compound, or pharmaceutically acceptable salt or prodrug thereof, described herein. The decrease in activity may be due to the direct interaction of the at least one compound, or pharmaceutically acceptable salt or prodrug thereof, described herein with KMO or with one or more other factors that in turn affect KMO activity.

Inhibition of KMO activity also refers to an observable inhibition of 3-HK and QUIN production in a standard assay such as the assay described below. The inhibition of KMO activity also refers to an observable increase in the production of KYNA. In some embodiments, the compound, or pharmaceutically acceptable salt or prodrug thereof, described herein has an $IC_{50}$ value less than or equal to 1 micromolar. In some embodiments, the compound, or pharmaceutically acceptable salt or prodrug thereof, described herein has an $IC_{50}$ value less than or equal to less than 100 micromolar. In some embodiments, the compound, or pharmaceutically acceptable salt or prodrug thereof, described herein has an $IC_{50}$ value less than or equal to 10 nanomolar.

"KMO activity" also includes activation, redistribution, reorganization, or capping of one or more various KMO membrane-associated proteins (such as those receptors found in the mitochondria), or binding sitescan undergo redistribution and capping that can initiate signal transduction. KMO activity also can modulate the availability of kynurenine, which can effect the synthesis or production of QUIN, KYNA, anthranilic acid, and/or 3-HK.

A "disease responsive to inhibition of KMO activity" is a disease in which inhibiting KMO provides a therapeutic benefit such as an amelioration of symptoms, decrease in disease progression, prevention or delay of disease onset, prevention or amelioration of an inflammatory response, or inhibition of aberrant activity and/or death of certain cell-types (such as neuronal cells).

"Treatment" or "treating" means any treatment of a disease in a patient, including:
a) preventing the disease, that is, causing the clinical symptoms of the disease not to develop;
b) inhibiting the progression of the disease;
c) slowing or arresting the development of clinical symptoms; and/or
d) relieving the disease, that is, causing the regression of clinical symptoms.

"Subject" or "patient" refers to an animal, such as a mammal, that has been or will be the object of treatment, observation or experiment. The methods described herein may be useful in both human therapy and veterinary applications. In some embodiments, the subject is a mammal; and in some embodiments the subject is human.

The term "disease" as used herein is intended to be generally synonymous, and is used interchangeably with, the terms "disorder" and "condition" (as in medical condition), in that all reflect an abnormal condition of the human or animal body or of one or more of its parts that impairs normal functioning, is typically manifested by distinguishing signs and symptoms, and causes the human or animal to have a reduced duration or quality of life.

Provided is a compound of Formula I

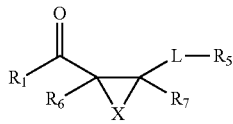

Formula I or a pharmaceutically acceptable salt or prodrug thereof, wherein $R_1$ is optionally substituted heteroaryl;

X is —$CR_2R_3$—;

$R_2$ and $R_3$ are independently chosen from hydrogen, optionally substituted amino, hydroxyl, lower alkoxy, and optionally substituted lower alkyl;

L is —C(O)O—;

$R_5$ is hydrogen; and $R_6$ and $R_7$ are independently chosen from hydrogen, halo, optionally substituted amino, hydroxyl, lower alkoxy, and optionally substituted lower alkyl.

In some embodiments, $R_1$ is chosen from thiophenyl, thiazolyl, and pyridyl, any of which may be optionally substituted with one, two or three groups independently chosen from halogen and lower alkyl.

In some embodiments, $R_1$ is chosen from 5-chlorothiophen-2-yl, thiophen-3-yl, thiophen-2-yl, thiazol-2-yl, and pyridin-2-yl.

In some embodiments, $R_1$ is chosen from 1,3-benzothiazol-2-yl, 1,3-benzothiazol-6-yl, quinoxalin-6-yl, quinolin-6-yl, 1-benzofuran-5-yl, isoquinolin-6-yl, quinazolin-7-yl, quinazolin-6-yl, cinnolin-6-yl, benzo[d]oxazol-6-yl, 1H-benzo[d]imidazol-6-yl, benzo[d]oxazol-5-yl, benzo[d]thiazol-5-yl, 1H-indol-5-yl, 1H-indazol-5-yl, 1H-indazol-5-yl, 2,3-dihydrobenzo[d]oxazol-6-yl, 2,3-dihydro-1H-benzo[d]imidazol-5-yl, benzo[d]isoxazol-5-yl, and benzofuran-5-yl, any of which may be optionally substituted with one, two or three groups independently chosen from oxo, halogen and lower alkyl.

In some embodiments, $R_1$ is chosen from 1,3-benzothiazol-2-yl, 2-methyl-1,3-benzothiazol-6-yl, 8-chloroquinoxalin-6-yl, 8-chloroquinolin-6-yl, 7-chloro-2-methyl-1-benzofuran-5-yl, 7-chloro-1-benzofuran-5-yl, 8-chloroisoquinolin-6-yl, 5-chloroquinazolin-7-yl, 8-chloroquinazolin-6-yl, 8-chlorocinnolin-6-yl, 4-chlorobenzo[d]oxazol-6-yl, 4-chloro-2-methylbenzo[d]oxazol-6-yl, 4-chloro-1H-benzo[d]imidazol-6-yl, 7-chlorobenzo[d]oxazol-5-yl, 7-chloro-2-methylbenzo[d]oxazol-5-yl, 7-chlorobenzo[d]thiazol-5-yl, 7-chloro-2-methylbenzo[d]thiazol-5-yl, 7-chloro-1H-indol-5-yl, 7-chloro-1H-indazol-5-yl, 7-chloro-1-methyl-1H-indazol-5-yl, 4-chloro-2-oxo-2,3-dihydrobenzo[d]oxazol-6-yl, 7-chloro-3-methyl-2-oxo-2,3-dihydro-1H-benzo[d]imidazol-5-yl, 7-chlorobenzo[d]isoxazol-5-yl, 7-chloro-1-methyl-1H-indol-5-yl, and 7-chlorobenzofuran-5-yl.

In some embodiments, $R_1$ is chosen from 7-chlorobenzofuran-5-yl, 7-chloro-2-methylbenzo[d]oxazol-5-yl, and 4-chlorobenzo[d]oxazol-6-yl.

In some embodiments, $R_2$ is chosen from hydrogen, hydroxyl, lower alkoxy, amino optionally substituted with one or more alkyl groups, and lower alkyl optionally substituted with one or more groups independently chosen from halo, hydroxyl, lower alkoxy, and amino optionally substituted with one or more alkyl groups.

In some embodiments, $R_2$ is chosen from hydrogen, amino, methylamino, dimethylamino, hydroxyl, methyl, methoxy, difluoromethyl, trifluoromethyl, hydroxymethyl, methoxymethyl, aminomethyl, (methylamino)methyl, and (dimethylamino)methyl.

In some embodiments, $R_3$ is chosen from hydrogen and lower alkyl.

In some embodiments, $R_3$ is chosen from hydrogen and methyl.

In some embodiments, $R_2$ and $R_3$ are hydrogen.

In some embodiments, $R_2$ is methyl and $R_3$ is hydrogen.

In some embodiments, $R_2$ and $R_3$ are methyl.

In some embodiments, $R_6$ is chosen from hydrogen, amino, methylamino, dimethylamino, aminomethyl, methylaminomethyl, (dimethylamino)methyl, and methyl.

In some embodiments, $R_6$ is hydrogen.

In some embodiments, $R_7$ is chosen from hydrogen, amino, methylamino, dimethylamino, aminomethyl, (methylamino)methyl, (dimethylamino)methyl, methoxymethyl, methyl, 1-aminoethyl, 1-methoxy-ethyl, methoxy, and halo.

In some embodiments, $R_7$ is methyl.

In some embodiments, $R_7$ is hydrogen.

Also provided is a compound chosen from the compounds listed in Table 1 or 2, or a pharmaceutically acceptable salt or prodrug thereof.

TABLE 1

(1S,2S)-2-(2-methyl-1,3-benzothiazole-6-carbonyl)cyclopropane-1-carboxylic acid
(1S,2S)-2-(7-chloro-1-benzofuran-5-carbonyl)cyclopropane-1-carboxylic acid
(1S,2S)-2-(7-chloro-2-methyl-1-benzofuran-5-carbonyl)cyclopropane-1-carboxylic acid
(1S,2S)-2-(8-chloroquinoline-6-carbonyl)cyclopropane-1-carboxylic acid
(1S,2S)-2-(8-chloroquinoxaline-6-carbonyl)cyclopropane-1-carboxylic acid
(1S,2S)-2-[(1,3-Benzothiazol-2-yl)carbonyl]cyclopropane-1-carboxylic acid
(1S,2S)-2-[(1,3-Thiazol-2-yl)carbonyl]cyclopropane-1-carboxylic acid
(1S,2S)-2-[(5-Chlorothiophen-2-yl)carbonyl]cyclopropane-1-carboxylic acid
(1S,2S)-2-[(Pyridin-2-yl)carbonyl]cyclopropane-1-carboxylic acid
(1S,2S)-2-[(Thiophen-2-yl)carbonyl]cyclopropane-1-carboxylic acid
(1S,2S)-2-[(Thiophen-3-yl)carbonyl]cyclopropane-1-carboxylic acid
(1S,2S)-2-(8-chloroisoquinoline-6-carbonyl)cyclopropanecarboxylic acid
(1S,2S)-2-(5-chloroquinazoline-7-carbonyl)cyclopropanecarboxylic acid
(1S,2S)-2-(8-chloroquinazoline-6-carbonyl)cyclopropanecarboxylic acid
(1S,2S)-2-(8-chlorocinnoline-6-carbonyl)cyclopropanecarboxylic acid
(1S,2S)-2-(4-chlorobenzo[d]oxazole-6-carbonyl)cyclopropanecarboxylic acid
(1S,2S)-2-(4-chloro-2-methylbenzo[d]oxazole-6-carbonyl)cyclopropanecarboxylic acid
(1S,2S)-2-(4-chloro-1H-benzo[d]imidazole-6-carbonyl)cyclopropanecarboxylic acid
(1S,2S)-2-(7-chlorobenzo[d]oxazole-5-carbonyl)cyclopropanecarboxylic acid
(1S,2S)-2-(7-chloro-2-methylbenzo[d]oxazole-5-carbonyl)cyclopropanecarboxylic acid
(1S,2S)-2-(7-chlorobenzo[d]thiazole-5-carbonyl)cyclopropanecarboxylic acid

TABLE 1-continued (1S,2S)-2-(7-chloro-2-methylbenzo[d]thiazole-5-carbonyl)cyclopropanecarboxylic acid
(1S,2S)-2-(7-chloro-1H-indole-5-carbonyl)cyclopropanecarboxylic acid
(1S,2S)-2-(7-chloro-1H-indazole-5-carbonyl)cyclopropanecarboxylic acid
(1S,2S)-2-(7-chloro-1-methyl-1H-indazole-5-carbonyl)cyclopropanecarboxylic acid
(1S,2S)-2-(4-chloro-2-oxo-2,3-dihydrobenzo[d]oxazole-6-carbonyl)cyclopropanecarboxylic acid
(1S,2S)-2-(7-chloro-2-oxo-2,3-dihydro-1H-benzo[d]imidazole-5-carbonyl)cyclopropanecarboxylic acid
(1S,2S)-2-(7-chloro-3-methyl-2-oxo-2,3-dihydro-1H-benzo[d]imidazole-5-carbonyl)cyclopropanecarboxylic acid
(1S,2S)-2-(7-chloro-1-methyl-2-oxo-2,3-dihydro-1H-benzo[d]imidazole-5-carbonyl)cyclopropanecarboxylic acid
(1S,2S)-2-(7-chlorobenzo[d]isoxazole-5-carbonyl)cyclopropanecarboxylic acid
(1S,2S)-2-(7-chloro-1-methyl-1H-indole-5-carbonyl)cyclopropanecarboxylic acid
(1R,2S)-1-amino-2-(7-chlorobenzofuran-5-carbonyl)cyclopropanecarboxylic acid
(1R,2S)-2-(7-chlorobenzofuran-5-carbonyl)-1-(methylamino)cyclopropanecarboxylic acid
(1R,2S)-2-(7-chlorobenzofuran-5-carbonyl)-1-(dimethylamino)cyclopropanecarboxylic acid
(1S,2S)-1-(aminomethyl)-2-(7-chlorobenzofuran-5-carbonyl)cyclopropanecarboxylic acid
(1S,2S)-2-(7-chlorobenzofuran-5-carbonyl)-1-((methylamino)methyl)cyclopropanecarboxylic acid
(1S,2S)-2-(7-chlorobenzofuran-5-carbonyl)-1-((dimethylamino)methyl)cyclopropanecarboxylic acid
(1S,2S)-2-(7-chlorobenzofuran-5-carbonyl)-1-methylcyclopropanecarboxylic acid
(1R,2R)-2-(7-chlorobenzofuran-5-carbonyl)-1-fluorocyclopropanecarboxylic acid
(1R,2S)-2-(7-chlorobenzofuran-5-carbonyl)-1-methoxycyclopropanecarboxylic acid
(1S,2S)-2-(7-chlorobenzofuran-5-carbonyl)-1-(methoxymethyl)cyclopropanecarboxylic acid
(1R,3R)-2-amino-3-(7-chlorobenzofuran-5-carbonyl)cyclopropanecarboxylic acid
(1R,2R)-2-(7-chlorobenzofuran-5-carbonyl)-3-(methylamino)cyclopropanecarboxylic acid
(1R,2R)-2-(7-chlorobenzofuran-5-carbonyl)-3-(dimethylamino)cyclopropanecarboxylic acid
(1S,2S)-2-(7-chlorobenzofuran-5-carbonyl)-3-methylcyclopropanecarboxylic acid
(1R,3R)-3-(7-chlorobenzofuran-5-carbonyl)-2,2-dimethylcyclopropanecarboxylic acid
(1R,3R)-3-(7-chlorobenzofuran-5-carbonyl)-2-hydroxy-2-methylcyclopropanecarboxylic acid
(1R,3R)-3-(7-chlorobenzofuran-5-carbonyl)-2-(hydroxymethyl)-2-methylcyclopropanecarboxylic acid
(1R,3R)-3-(7-chlorobenzofuran-5-carbonyl)-2-(methoxymethyl)-2-methylcyclopropanecarboxylic acid
(1R,3R)-2-(aminomethyl)-3-(7-chlorobenzofuran-5-carbonyl)-2-methylcyclopropanecarboxylic acid
(1R,3R)-3-(7-chlorobenzofuran-5-carbonyl)-2-methyl-2-((methylamino)methyl)cyclopropanecarboxylic acid
(1R,3R)-2-amino-3-(7-chlorobenzofuran-5-carbonyl)-2-methylcyclopropanecarboxylic acid
(1R,3R)-3-(7-chlorobenzofuran-5-carbonyl)-2-methyl-2-(methylamino)cyclopropanecarboxylic acid
(1S,3S)-2-(aminomethyl)-3-(7-chlorobenzofuran-5-carbonyl)cyclopropanecarboxylic acid
(1S,2S)-2-(7-chlorobenzofuran-5-carbonyl)-3-((methylamino)methyl)cyclopropanecarboxylic acid
(1S,2S)-2-(7-chlorobenzofuran-5-carbonyl)-3-((dimethylamino)methyl)cyclopropanecarboxylic acid
(1S,2R)-2-amino-2-(7-chlorobenzofuran-5-carbonyl)cyclopropanecarboxylic acid
(1S,2R)-2-(7-chlorobenzofuran-5-carbonyl)-2-(methylamino)cyclopropanecarboxylic acid
(1S,2R)-2-(7-chlorobenzofuran-5-carbonyl)-2-(dimethylamino)cyclopropanecarboxylic acid
(1S,2S)-2-(aminomethyl)-2-(7-chlorobenzofuran-5-carbonyl)cyclopropanecarboxylic acid
(1S,2S)-2-(7-chlorobenzofuran-5-carbonyl)-2-((methylamino)methyl)cyclopropanecarboxylic acid
(1S,2S)-2-(7-chlorobenzofuran-5-carbonyl)-2-((dimethylamino)methyl)cyclopropanecarboxylic acid
(1S,2S)-2-(7-chlorobenzofuran-5-carbonyl)-2-methylcyclopropanecarboxylic acid

TABLE 2

(1S,2S)-2-(2-methyl-1,3-benzothiazole-6-carbonyl)cyclopropane-1-carboxylic acid
(1S,2S)-2-(7-chloro-1-benzofuran-5-carbonyl)cyclopropane-1-carboxylic acid
(1S,2S)-2-(7-chloro-2-methyl-1-benzofuran-5-carbonyl)cyclopropane-1-carboxylic acid
(1S,2S)-2-(8-chloroquinoline-6-carbonyl)cyclopropane-1-carboxylic acid
(1S,2S)-2-(8-chloroquinoxaline-6-carbonyl)cyclopropane-1-carboxylic acid
(1S,2S)-2-[(1,3-Benzothiazol-2-yl)carbonyl]cyclopropane-1-carboxylic acid
(1S,2S)-2-[(1,3-Thiazol-2-yl)carbonyl]cyclopropane-1-carboxylic acid
(1S,2S)-2-[(5-Chlorothiophen-2-yl)carbonyl]cyclopropane-1-carboxylic acid
(1S,2S)-2-[(Pyridin-2-yl)carbonyl]cyclopropane-1-carboxylic acid
(1S,2S)-2-[(Thiophen-2-yl)carbonyl]cyclopropane-1-carboxylic acid
(1S,2S)-2-[(Thiophen-3-yl)carbonyl]cyclopropane-1-carboxylic acid Also provided is a compound chosen from the compounds listed in Table 3, each of which may be considered a prodrug of a compound of Formula I.

TABLE 3 methyl (1S,2S)-2-(7-chloro-1-benzofuran-5-carbonyl)cyclopropane-1-carboxylate
[(3R,4S,5R,6S)-3,4,5,6-tetrahydroxyoxan-2-yl]methyl (1S,2S)-2-(7-chloro-1-benzofuran-5-carbonyl)cyclopropane-1-carboxylate TABLE 3-continued

[(3S,4S,5R)-3,4,5,6-tetrahydroxyoxan-2-yl]methyl (1S,2S)-2-(7-chloro-1-benzofuran-5-carbonyl)cyclopropane-1-carboxylate
2-hydroxyethyl (1S,2S)-2-(7-chloro-1-benzofuran-5-carbonyl)cyclopropane-1-carboxylate
(1S,2S)-2-(7-chloro-1-benzofuran-5-carbonyl)-N-hydroxycyclopropane-1-carboxamide
propan-2-yl (1S,2S)-2-(7-chloro-1-benzofuran-5-carbonyl)cyclopropane-1-carboxylate
2-(diethylamino)ethyl (1S,2S)-2-(7-chloro-1-benzofuran-5-carbonyl)cyclopropane-1-carboxylate
(2S)-2-amino-6-{[(1S,2S)-2-(7-chloro-1-benzofuran-5-carbonyl)cyclopropyl]formamido}hexanoic acid
[(1S,2S)-2-(7-chloro-1-benzofuran-5-carbonyl)cyclopropanecarbonyloxy]methyl 2,2-dimethylpropanoate
1-[(1S,2S)-2-(7-chloro-1-benzofuran-5-carbonyl)cyclopropanecarbonyloxy]ethyl acetate
{3-carboxy-2-[(1S,2S)-2-(7-chloro-1-benzofuran-5-carbonyl)cyclopropanecarbonyloxy]propyl}trimethylazanium
1-{[(propan-2-yloxy)carbonyl]oxy}ethyl (1S,2S)-2-(7-chloro-1-benzofuran-5-carbonyl)cyclopropane-1-carboxylate
1-[(ethoxycarbonyl)oxy]ethyl (1S,2S)-2-(7-chloro-1-benzofuran-5-carbonyl)cyclopropane-1-carboxylate
4-tert-butylphenyl (1S,2S)-2-(7-chloro-1-benzofuran-5-carbonyl)cyclopropane-1-carboxylate
2-methylpropyl (1S,2S)-2-(7-chloro-1-benzofuran-5-carbonyl)cyclopropane-1-carboxylate
butyl (1S,2S)-2-(7-chloro-1-benzofuran-5-carbonyl)cyclopropane-1-carboxylate
(2S)-2-{[(1S,2S)-2-(7-chloro-1-benzofuran-5-carbonyl)cyclopropyl]formamido}-3-hydroxypropanoic acid
methyl (1S,2S)-2-(7-chloro-2-methyl-1-benzofuran-5-carbonyl)cyclopropane-1-carboxylate
[(3R,4S,5R,6S)-3,4,5,6-tetrahydroxyoxan-2-yl]methyl (1S,2S)-2-(7-chloro-2-methyl-1-benzofuran-5-carbonyl)cyclopropane-1-carboxylate
[(3S,4S,5R)-3,4,5,6-tetrahydroxyoxan-2-yl]methyl (1S,2S)-2-(7-chloro-2-methyl-1-benzofuran-5-carbonyl)cyclopropane-1-carboxylate
2-hydroxyethyl (1S,2S)-2-(7-chloro-2-methyl-1-benzofuran-5-carbonyl)cyclopropane-1-carboxylate
(1S,2S)-2-(7-chloro-2-methyl-1-benzofuran-5-carbonyl)-N-hydroxycyclopropane-1-carboxamide
propan-2-yl (1S,2S)-2-(7-chloro-2-methyl-1-benzofuran-5-carbonyl)cyclopropane-1-carboxylate
2-(diethylamino)ethyl (1S,2S)-2-(7-chloro-2-methyl-1-benzofuran-5-carbonyl)cyclopropane-1-carboxylate
(2S)-2-amino-6-{[(1S,2S)-2-(7-chloro-2-methyl-1-benzofuran-5-carbonyl)cyclopropyl]formamido}hexanoic acid
[(1S,2S)-2-(7-chloro-2-methyl-1-benzofuran-5-carbonyl)cyclopropanecarbonyloxy]methyl 2,2-dimethylpropanoate
1-[(1S,2S)-2-(7-chloro-2-methyl-1-benzofuran-5-carbonyl)cyclopropanecarbonyloxy]ethyl acetate
{3-carboxy-2-[(1S,2S)-2-(7-chloro-2-methyl-1-benzofuran-5-carbonyl)cyclopropanecarbonyloxy]propyl}trimethylazanium
1-{[(propan-2-yloxy)carbonyl]oxy}ethyl (1S,2S)-2-(7-chloro-2-methyl-1-benzofuran-5-carbonyl)cyclopropane-1-carboxylate
1-[(ethoxycarbonyl)oxy]ethyl (1S,2S)-2-(7-chloro-2-methyl-1-benzofuran-5-carbonyl)cyclopropane-1-carboxylate
4-tert-butylphenyl (1S,2S)-2-(7-chloro-2-methyl-1-benzofuran-5-carbonyl)cyclopropane-1-carboxylate
2-methylpropyl (1S,2S)-2-(7-chloro-2-methyl-1-benzofuran-5-carbonyl)cyclopropane-1-carboxylate
butyl (1S,2S)-2-(7-chloro-2-methyl-1-benzofuran-5-carbonyl)cyclopropane-1-carboxylate
(2S)-2-{[(1S,2S)-2-(7-chloro-2-methyl-1-benzofuran-5-carbonyl)cyclopropyl]formamido}-3-hydroxypropanoic acid
methyl (1S,2S)-2-(4-chloro-2-methyl-1,3-benzoxazole-6-carbonyl)cyclopropane-1-carboxylate
[(3R,4S,5R,6S)-3,4,5,6-tetrahydroxyoxan-2-yl]methyl (1S,2S)-2-(4-chloro-2-methyl-1,3-benzoxazole-6-carbonyl)cyclopropane-1-carboxylate
[(3S,4S,5R)-3,4,5,6-tetrahydroxyoxan-2-yl]methyl (1S,2S)-2-(4-chloro-2-methyl-1,3-benzoxazole-6-carbonyl)cyclopropane-1-carboxylate
2-hydroxyethyl (1S,2S)-2-(4-chloro-2-methyl-1,3-benzoxazole-6-carbonyl)cyclopropane-1-carboxylate
(1S,2S)-2-(4-chloro-2-methyl-1,3-benzoxazole-6-carbonyl)-N-hydroxycyclopropane-1-carboxamide
propan-2-yl (1S,2S)-2-(4-chloro-2-methyl-1,3-benzoxazole-6-carbonyl)cyclopropane-1-carboxylate
2-(diethylamino)ethyl (1S,2S)-2-(4-chloro-2-methyl-1,3-benzoxazole-6-carbonyl)cyclopropane-1-carboxylate
(2S)-2-amino-6-{[(1S,2S)-2-(4-chloro-2-methyl-1,3-benzoxazole-6-carbonyl)cyclopropyl]formamido}hexanoic acid
[(1S,2S)-2-(4-chloro-2-methyl-1,3-benzoxazole-6-carbonyl)cyclopropanecarbonyloxy]methyl 2,2-dimethylpropanoate TABLE 3-continued 1-[(1S,2S)-2-(4-chloro-2-methyl-1,3-benzoxazole-6-carbonyl)cyclopropanecarbonyloxy]ethyl acetate
{3-carboxy-2-[(1S,2S)-2-(4-chloro-2-methyl-1,3-benzoxazole-6-carbonyl)cyclopropanecarbonyloxy]propyl}trimethylazanium
1-{[(propan-2-yloxy)carbonyl]oxy}ethyl (1S,2S)-2-(4-chloro-2-methyl-1,3-benzoxazole-6-carbonyl)cyclopropane-1-carboxylate
1-[(ethoxycarbonyl)oxy]ethyl (1S,2S)-2-(4-chloro-2-methyl-1,3-benzoxazole-6-carbonyl)cyclopropane-1-carboxylate
4-tert-butylphenyl (1S,2S)-2-(4-chloro-2-methyl-1,3-benzoxazole-6-carbonyl)cyclopropane-1-carboxylate
2-methylpropyl (1S,2S)-2-(4-chloro-2-methyl-1,3-benzoxazole-6-carbonyl)cyclopropane-1-carboxylate
butyl (1S,2S)-2-(4-chloro-2-methyl-1,3-benzoxazole-6-carbonyl)cyclopropane-1-carboxylate
(2S)-2-{[(1S,2S)-2-(4-chloro-2-methyl-1,3-benzoxazole-6-carbonyl)cyclopropyl]formamido}-3-hydroxypropanoic acid
methyl (1S,2S)-2-(7-chloro-2-methyl-1,3-benzoxazole-5-carbonyl)cyclopropane-1-carboxylate
[(3R,4S,5R,6S)-3,4,5,6-tetrahydroxyoxan-2-yl]methyl (1S,2S)-2-(7-chloro-2-methyl-1,3-benzoxazole-5-carbonyl)cyclopropane-1-carboxylate
[(3S,4S,5R)-3,4,5,6-tetrahydroxyoxan-2-yl]methyl (1S,2S)-2-(7-chloro-2-methyl-1,3-benzoxazole-5-carbonyl)cyclopropane-1-carboxylate
2-hydroxyethyl (1S,2S)-2-(7-chloro-2-methyl-1,3-benzoxazole-5-carbonyl)cyclopropane-1-carboxylate
(1S,2S)-2-(7-chloro-2-methyl-1,3-benzoxazole-5-carbonyl)-N-hydroxycyclopropane-1-carboxamide
propan-2-yl (1S,2S)-2-(7-chloro-2-methyl-1,3-benzoxazole-5-carbonyl)cyclopropane-1-carboxylate
2-(diethylamino)ethyl (1S,2S)-2-(7-chloro-2-methyl-1,3-benzoxazole-5-carbonyl)cyclopropane-1-carboxylate
(2S)-2-amino-6-{[(1S,2S)-2-(7-chloro-2-methyl-1,3-benzoxazole-5-carbonyl)cyclopropyl]formamido}hexanoic acid
[(1S,2S)-2-(7-chloro-2-methyl-1,3-benzoxazole-5-carbonyl)cyclopropanecarbonyloxy]methyl 2,2-dimethylpropanoate
1-[(1S,2S)-2-(7-chloro-2-methyl-1,3-benzoxazole-5-carbonyl)cyclopropanecarbonyloxy]ethyl acetate
{3-carboxy-2-[(1S,2S)-2-(7-chloro-2-methyl-1,3-benzoxazole-5-carbonyl)cyclopropanecarbonyloxy]propyl}trimethylazanium
1-{[(propan-2-yloxy)carbonyl]oxy}ethyl (1S,2S)-2-(7-chloro-2-methyl-1,3-benzoxazole-5-carbonyl)cyclopropane-1-carboxylate
1-[(ethoxycarbonyl)oxy]ethyl (1S,2S)-2-(7-chloro-2-methyl-1,3-benzoxazole-5-carbonyl)cyclopropane-1-carboxylate
4-tert-butylphenyl (1S,2S)-2-(7-chloro-2-methyl-1,3-benzoxazole-5-carbonyl)cyclopropane-1-carboxylate
2-methylpropyl (1S,2S)-2-(7-chloro-2-methyl-1,3-benzoxazole-5-carbonyl)cyclopropane-1-carboxylate
butyl (1S,2S)-2-(7-chloro-2-methyl-1,3-benzoxazole-5-carbonyl)cyclopropane-1-carboxylate
(2S)-2-{[(1S,2S)-2-(7-chloro-2-methyl-1,3-benzoxazole-5-carbonyl)cyclopropyl]formamido}-3-hydroxypropanoic acid Methods for obtaining the compound, or pharmaceutically acceptable salt or prodrug thereof, described herein will be apparent to those of ordinary skill in the art, suitable procedures being described, for example, in examples below, and in the references cited herein.

Provided is a method of inhibiting the catalytic activity of KMO, comprising contacting said KMO with an effective amount of at least one compound, or pharmaceutically acceptable salt or prodrug thereof, described herein.

Also provided is a method of treating a condition or disorder mediated by KMO activity in a subject in need of such a treatment, comprising administering to the subject a therapeutically effective amount of at least one compound, or pharmaceutically acceptable salt or prodrug thereof, described herein.

Also provided is a method of treating a neurodegenerative pathology mediated by KMO activity in a subject in need of such a treatment, comprising administering to the subject a therapeutically effective amount of at least one compound, or pharmaceutically acceptable salt or prodrug thereof, described herein.

Also provided is a method for treating disorders mediated by (or at least in part by) the presence 3-OH-KYN, QUIN and/or KYNA. Also provided is a method of treating a degenerative or inflammatory condition in which an increased synthesis in the brain of QUIN, 3-OH-KYN or increased release of GLU are involved and which may cause neuronal damage.

Such diseases include, for example, Huntington's disease and other polyglutamine disorders such as spinocerebellar ataxias neurodegenerative diseases, psychiatric of neurological diseases or disorders, Alzheimer's disease, Parkinson's disease, amyotropic lateral sclerosis, Creutzfeld-Jacob disease, trauma-induced neurodegeneration, high-pressure neurological syndrome, dystonia, olivopontocerebellar atrophy, amyotrophic lateral sclerosis, multiple sclerosis, epilepsy, consequences of stroke, cerebral ischemia, ischemic disorders including stroke (focal ischemia), hypoxia, multi-infarct dementia, consequences of cerebral trauma or damage, damage to the spinal cord, Dementia such as senile dementia and AIDS-dementia complex, AIDS-induced encephalopathy, other infection related encephalopathy, viral or bacterial meningitis, infectious diseases caused by viral, bacterial and other parasites, for example, general central nervous system (CNS) infections such as viral, bacterial or parasites, for example, poliomyelitis, Lyme disease (*Borrelia burgdorferi* infection) septic shock, and malaria, cancers, cancers with cerebral localization, hepatic encephalopathy, systemic lupus, analgesia and opiate withdrawal symptoms, feeding behavior, psychiatric disorders, such as insomnia, depression, schizophrenia, severe deficit in working memory, severe deficit in long term memory storage, decrease in cognition, severe deficit in attention, severe deficit in executive functioning, sloweness in information processing, slowness in neural activity, anxiety, generalized anxiety disorders, panic anxiety, obsessive compulsive disorders, social phobia, performance anxiety, post-traumatic stress disorder, acute stress reaction, adjustment reaction, separation anxiety disorder, alcohol withdrawal anxiety, depressive disorders, disorders of the developing or aged brain, diabetes, and complications thereof, Tourette's syndrome, Fragile X syndrome, autism spectrum disorders, disorders that cause severe and pervasive impairment in thinking feeling, language and the ability to relate to others, mood disorders, psychological disorders characterized by abnormalities of emotional state, such as without limitation, bipolar disorder, unipolar depression, major depression, ondougenous depression, involutional depression, reactive depression, psychotic depression, depression caused by underlying medical conditions, depressive disorders, cyclothymic disorders, dysthymic disorders, mood disorders due to general medical condition, mood disorders not otherwise specified and substance-induced mood disorders. Such disease also include, for example, Acute necrotizing Pancreatitis, AIDS (disease), Analgesia, Aseptic meningitis, Brain disease, for example, Gilles de la Tourette syndrome, Asperger syndrome, Rett syndrome, pervasive developmental disorders, aging-related Brain disease, and developmental Brain disease, burnout syndrome, carbon monoxide poisoning, cardiac arrest or insufficiency and hemorrhagic shock (global brain ischemia), cataract formation and aging of the eye, Central nervous system disease, Cerebrovascular disease, chronic fatigue syndrome, Chronic Stress, Cognitive disorders, convulsive Disorders, such as variants of Grand mal and petit mal epilepsy and Partial Complex Epilepsy, Diabetes mellitus, Disease of the nervous system (e.g., dyskinesia, L-DOPA induced movement disorders, drug addiction, pain and cataract), Drug dependence, Drug withdrawal, feeding disorders, Guillain Barr Syndrome and other neurophaties, Hepatic encephalopathy, Immune disease, immunitary disorders and therapeutic treatment aimed at modifying biological responses (for instance administrations of interferons or interleukins), Inflammation (systemic inflammatory response syndrome), inflammatory disorders of the central and/or peripheral nervous system, Injury (trauma, polytrauma), Mental and behavioral disorders, Metabolic disease, pain disease, or disorder selected from a group of inflammatory pain, neurophathic pain or migraine, allodynia, hyperalgesis pain, phantom pain, neurophatic pain related to diabetic neuropathy, Multiple organ failure, near drowning, Necrosis, neoplasms of the brain, neoplastic disorders including lymphomas and other malignant blood disorders, Nervous system disease (high-pressure neurol. Syndrome, infection), nicotine addiction and other addictive disorders including alcoholism, *cannabis*, benzodiazepine, barbiturate, morphine and cocaine dependence, change in appetite, sleep disorders, changes in sleep pattern, lack of energy, fatigue, low self esteem, self-reproach inappropriate guilt, frequent thoughts of death or suicide, plans or attempts to commit suicide, feelings of hopelessness and worthlessness, psychomotor agitation or retardation, diminished capacity for thinking, concentration, or decisiveness, as a Neuroprotective agents, Pain, Post-traumatic stress disorder, Sepsis, Spinal cord disease, Spinocerebellar ataxia, Systemic lupus erythematosis, traumatic damage to the brain and spinal cord, and tremor syndromes and different movement disorders (diskynesia). Poor balance, brakykinesia, rigidity, tremor, change in speech, loss of facial expression, micrographia, difficulty swallowing, drooling, dementia, confusion, fear, sexual disfunction, language impairment, impairment in decision making, violent outbursts, aggression, hallucination, apathy, impairment in abstract thinking.

Such diseases include, for example, cardiovascular diseases, which refers to diseases and disorders of the heart and circulatory system. These diseases are often associated with dyslipoproteinemias and/or dyslipidemias. Cardiovascular diseases include but are not limited to cardiomegaly, atherosclerosis, myocardial infarction, and congestive heart failure, coronary heart disease, hypertension and hypotension.

Other such diseases include hyperproliferative diseases of benign or malignant behaviour, in which cells of various tissues and organs exhibit aberrant patterns of growth, proliferation, migration, signaling, senescence, and death. Generally hyperproliferative disease refers to diseases and disorders associated with, the uncontrolled proliferation of cells, including but not limited to uncontrolled growth of organ and tissue cells resulting in cancers and benign tumors. Hyperproliferative disorders associated with endothelial cells can result in diseases of angiogenesis such as angiomas, endometriosis, obesity, Age-related Macular Degeneration and various retinopaties, as well as the proliferation of ECs and smooth muscle cells that cause restenosis as a consequence of stenting in the treatment of atherosclerosis. Hyperproliferative disorders involving fibroblasts (i.e., fibrogenesis) include but are not limited to disorders of excessive scaring (i.e., fibrosis) such as Age-related Macular Degeneration, cardiac remodeling and failure associated with myocardial infarction, excessive wound healing such as commonly occurs as a consequence of surgery or injury, keloids, and fibroid tumors and stenting.

Additional diseases include transplant rejection (suppression of T-cells) and graft vs host disease, chronic kidney disease, systemic inflammatory disorders, brain inflammatory disorders including malaria and African trypanosomiasis, stroke, and pneumococcal meningitis.

Also provided are methods of treatment in which at least one compound, or pharmaceutically acceptable salt or prodrug thereof, described herein is the only active agent given to the subject and also includes methods of treatment in which at least one compound, or pharmaceutically acceptable salt or prodrug thereof, described herein is given to the subject in combination with one or more additional active agents.

In general, at least one compound, or pharmaceutically acceptable salt or prodrug thereof, described herein will be administered in a therapeutically effective amount by any of the accepted modes of administration for agents that serve similar utilities. The actual amount of the compound, i.e., the active ingredient, will depend upon numerous factors such as the severity of the disease to be treated, the age and relative health of the subject, the potency of the compound used, the route and fonn of administration, and other factors well know to the skilled artisan. The drug can be administered at least once a day, such as once or twice a day.

In some embodiments, at least one compound, or pharmaceutically acceptable salt or prodrug thereof, described herein is administered as a pharmaceutical composition. Accordingly, provided are pharmaceutical compositions comprising at least one compound, or pharmaceutically acceptable salt or prodrug thereof, described herein, together with at least one pharmaceutically acceptable vehicle chosen from carriers, adjuvants, and excipients.

Pharmaceutically acceptable vehicles must be of sufficiently high purity and sufficiently low toxicity to render them suitable for administration to the animal being treated. The vehicle can be inert or it can possess pharmaceutical benefits. The amount of vehicle employed in conjunction with the one compound, or pharmaceutically acceptable salt or prodrug thereof, described herein is sufficient to provide a practical quantity of material for administration per unit dose of the compound, or pharmaceutically acceptable salt or prodrug thereof, described herein.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENS; wetting agents, such sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the compound, or pharmaceutically acceptable salt or prodrug thereof, described herein.

Effective concentrations of the compound, or pharmaceutically acceptable salt or prodrug thereof, described herein described herein are mixed with a suitable pharmaceutically acceptable vehicle. In instances in which the compound, or pharmaceutically acceptable salt or prodrug thereof, described herein exhibits insufficient solubility, methods for solubilizing compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate.

Upon mixing or addition of the compound, or pharmaceutically acceptable salt or prodrug thereof, described herein, the resulting mixture may be a solution, suspension, emulsion or the like. The form of the resulting mixture depends upon a number of factors, including the intended mode of administration and the solubility of the compound, or pharmaceutically acceptable salt or prodrug thereof, described herein in the chosen vehicle. The effective concentration sufficient for ameliorating the symptoms of the disease treated may be empirically determined.

The compound, or pharmaceutically acceptable salt or prodrug thereof, described herein may be administered orally, topically, parenterally, intravenously, by intramuscular injection, by inhalation or spray, sublingually, transdermally, via buccal administration, rectally, as an ophthalmic solution, or by other means, in dosage unit formulations.

Pharmaceutical compositions may be formulated for oral use, such as for example, tablets, troches, lozenges, aqueous or oily suspensions, dispersible powders or granules, emulsions, hard or soft capsules, or syrups or elixirs. Pharmaceutical compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. In some embodiments, oral pharmaceutical compositions contain from 0.1 to 99% of at least one compound, or pharmaceutically acceptable salt or prodrug thereof, described herein. In some embodiments, oral pharmaceutical compositions contain at least 5% (weight %) of at least one compound, or pharmaceutically acceptable salt or prodrug thereof, described herein. Some embodiments contain from 25% to 50% or from 5% to 75% of at least one compound, or pharmaceutically acceptable salt or prodrug thereof, described herein.

Orally administered pharmaceutical compositions also include liquid solutions, emulsions, suspensions, powders, granules, elixirs, tinctures, syrups, and the like. The pharmaceutically acceptable carriers suitable for preparation of such compositions are well known in the art. Oral pharmaceutical compositions may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such pharmaceutical compositions may also contain a demulcent.

The compound, or pharmaceutically acceptable salt or prodrug thereof, described herein can be incorporated into oral liquid preparations such as aqueous or oily suspensions, solutions, emulsions, syrups, or elixirs, for example. Moreover, pharmaceutical compositions containing at least one compound, or pharmaceutically acceptable salt or prodrug thereof, described herein can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monsoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

For a suspension, typical suspending agents include methylcellulose, sodium carboxymethyl cellulose, AVICEL RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxycthylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These pharmaceutical compositions may be preserved by the addition of an anti-oxidant such as ascorbic acid.

Pharmaceutical compositions may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets typically comprise conventional pharmaceutically acceptable adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, can be useful adjuvants for chewable tablets. Capsules (including time release and sustained release formulations) typically comprise one or more solid diluents disclosed above. The selection of carrier components often depends on secondary considerations like taste, cost, and shelf stability.

Such pharmaceutical compositions may also be coated by conventional methods, typically with pH or time-dependent coatings, such that the compound, or pharmaceutically acceptable salt or prodrug thereof, described herein is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Pharmaceutical compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable vehicle, for example as a solution in 1,3-butanediol. Among the acceptable vehicles that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables.

The compound, or pharmaceutically acceptable salt or prodrug thereof, described herein may be administered parenterally in a sterile medium. Parenteral administration includes subcutaneous injections, intravenous, intramuscular, intrathecal injection or infusion techniques. The compound, or pharmaceutically acceptable salt or prodrug thereof, described herein, depending on the vehicle and concentration used, can either be suspended or dissolved in the vehicle. Advantageously, adjuvants such as local anesthetics, preservatives and buffering agents can be dissolved in the vehicle. In many pharmaceutical compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

The compound, or pharmaceutically acceptable salt or prodrug thereof, described herein may also be administered in the form of suppositories for rectal administration of the drug. These pharmaceutical compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

The compound, or pharmaceutically acceptable salt or prodrug thereof, described herein may be formulated for local or topical application, such as for topical application to the skin and mucous membranes, such as in the eye, in the form of gels, creams, and lotions and for application to the eye. Topical pharmaceutical compositions may be in any form including, for example, solutions, creams, ointments, gels, lotions, milks, cleansers, moisturizers, sprays, skin patches, and the like.

Such solutions may be formulated as 0.01%-10% isotonic solutions, pH 5-7, with appropriate salts. The compound, or pharmaceutically acceptable salt or prodrug thereof, described herein may also be formulated for transdermal administration as a transdermal patch.

Topical pharmaceutical compositions comprising at least one compound, or pharmaceutically acceptable salt or prodrug thereof, described herein can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows:

Representative emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, *arachis* oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

The compound, or pharmaceutically acceptable salt or prodrug thereof, described herein may also be topically administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Other pharmaceutical compositions useful for attaining systemic delivery of the compound, or pharmaceutically acceptable salt or prodrug thereof, described herein include sublingual, buccal and nasal dosage forms. Such pharmaceutical compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Pharmaceutical compositions for inhalation typically can be provided in the form of a solution, suspension or emulsion that can be administered as a dry powder or in the form of an aerosol using a conventional propellant (e.g., dichlorodifluoromethane or trichlorofluoromethane).

The pharmaceutical compositions may also optionally comprise an activity enhancer. The activity enhancer can be chosen from a wide variety of molecules that function in different ways to enhance or be independent of therapeutic effects of the compound, or pharmaceutically acceptable salt or prodrug thereof, described herein. Particular classes of activity enhancers include skin penetration enhancers and absorption enhancers.

Pharmaceutical compositions may also contain additional active agents that can be chosen from a wide variety of molecules, which can function in different ways to enhance the therapeutic effects of the compound, or pharmaceutically acceptable salt or prodrug thereof, described herein. These optional other active agents, when present, are typically employed in the pharmaceutical compositions at a level ranging from 0.01% to 15%. Some embodiments contain from 0.1% to 10% by weight of the composition. Other embodiments contain from 0.5% to 5% by weight of the composition.

Also provided are packaged pharmaceutical compositions. Such packaged compositions include a pharmaceutical composition comprising at least one compound, or pharmaceutically acceptable salt or prodrug thereof, described herein, and instructions for using the composition to treat a subject (typically a human patient). In some embodiments, the instructions are for using the pharmaceutical composition to treat a subject suffering a condition or disorder mediated by Kynurenine 3-mono-oxygenase activity. The packaged pharmaceutical composition can include providing prescribing information; for example, to a patient or health care provider, or as a label in a packaged pharmaceutical composition. Prescribing information may include for example efficacy, dosage and administration, contraindication and adverse reaction information pertaining to the pharmaceutical composition.

In all of the foregoing the compound, or pharmaceutically acceptable salt or prodrug thereof, described herein can be administered alone, as mixtures, or in combination with other active agents.

The methods described herein include methods for treating Huntington's disease, including treating memory and/or cognitive impairment associated with Huntington's disease, comprising administering to a subject, simultaneously or sequentially, at least one compound, or pharmaceutically acceptable salt or prodrug thereof, described herein and one or more additional agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone. In methods using simultaneous administration, the agents can be present in a combined composition or can be administered separately. As a result, also provided are pharmaceutical compositions comprising at least one compound, or pharmaceutically acceptable salt or prodrug thereof, described herein and one or more additional pharmaceutical agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone. Similarly, also provided are packaged pharmaceutical compositions containing a pharmaceutical composition comprising at least one compound, or pharmaceutically acceptable salt or prodrug thereof, described herein, and another composition comprising one or more additional pharmaceutical agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone.

Also provided are methods for treating Parkinson's disease, including treating memory and/or cognitive impairment associated with Parkinson's disease, comprising administering to a subject, simultaneously or sequentially, at least one compound, or pharmaceutically acceptable salt or prodrug thereof, described herein and one or more additional agents used in the treatment of Parkinson's disease such as, but not limited to, Levodopa, Parlodel, Permax, Mirapex, Tasmar, Contan, Kemadin, Artane, and Cogentin. In methods using simultaneous administration, the agents can be present in a combined composition or can be administered separately. Also provided are pharmaceutical compositions comprising at least one compound, or pharmaceutically acceptable salt or prodrug thereof, described herein, and one or more additional pharmaceutical agents used in the treatment of Parkinson's disease, such as, but not limited to, Levodopa, Parlodel, Permax, Mirapex, Tasmar, Contan, Kemadin, Artane, and Cogentin. Also provided are packaged pharmaceutical compositions containing a pharmaceutical composition comprising at least one compound, or pharmaceutically acceptable salt or prodrug thereof, described herein, and another composition comprising one or more additional pharmaceutical agents gent used in the treatment of Parkinson's disease such as, but not limited to, Levodopa, Parlodel, Permax, Mirapex, Tasmar, Contan, Kemadin, Artane, and Cogentin.

Also provided are methods for treating memory and/or cognitive impairment associated with Alzheimer's disease, comprising administering to a subject, simultaneously or sequentially, at least one compound, or pharmaceutically acceptable salt or prodrug thereof, described herein and one or more additional agents used in the treatment of Alzheimer's disease such as, but not limited to, Reminyl, Cognex, Aricept, Exelon, Akatinol, Neotropin, Eldepryl, Estrogen and Cliquinol. In methods using simultaneous administration, the agents can be present in a combined composition or can be administered separately. Also provided are pharmaceutical compositions comprising at least one compound, or pharmaceutically acceptable salt or prodrug thereof, described herein, and one or more additional pharmaceutical agents used in the treatment of Alzheimer's disease such as, but not limited to, Reminyl, Cognex, Aricept, Exelon, Akatinol, Neotropin, Eldepryl, Estrogen and Cliquinol. Similarly, also provided are packaged pharmaceutical compositions containing a pharmaceutical composition comprising at least one compound, or pharmaceutically acceptable salt or prodrug thereof, described herein, and another composition comprising one or more additional pharmaceutical agents used in the treatment of Alzheimer's disease such as, but not limited to Reminyl, Cognex, Aricept, Exelon, Akatinol, Neotropin, Eldepryl, Estrogen and Cliquinol.

Also provided are methods for treating memory and/or cognitive impairment associated with dementia or cognitive impairment comprising administering to a subject, simultaneously or sequentially, at least one compound, or pharmaceutically acceptable salt or prodrug thereof, described herein and one or more additional agents used in the treatment of dementia such as, but not limited to, Thioridazine, Haloperidol, Risperidone, Cognex, Aricept, and Exelon. In methods using simultaneous administration, the agents can be present in a combined composition or can be administered separately. Also provided are pharmaceutical compositions comprising at least one compound, or pharmaceutically acceptable salt or prodrug thereof, described herein, and one or more additional pharmaceutical agents used in the treatment of dementia such as, but not limited to, Thioridazine, Haloperidol, Risperidone, Cognex, Aricept, and Exelon. Also provided are packaged pharmaceutical compositions containing a pharmaceutical composition comprising at least one compound, or pharmaceutically acceptable salt or prodrug thereof, described herein, and another composition comprising one or more additional pharmaceutical agents used in the treatment of dementia such as, but not limited to, Thioridazine, Haloperidol, Risperidone, Cognex, Aricept, and Exelon.

Also provided are methods for treating memory and/or cognitive impairment associated with epilepsy comprising administering to a subject, simultaneously or sequentially, at least one compound, or pharmaceutically acceptable salt or prodrug thereof, described herein and one or more additional agents used in the treatment of epilepsy such as, but not limited to, Dilantin, Luminol, Tegretol, Depakote, Depakene, Zarontin, Neurontin, Barbita, Solfeton, and Felbatol. In methods using simultaneous administration, the agents can be present in a combined composition or can be administered separately. Also provided are pharmaceutical compositions comprising at least one compound, or pharmaceutically acceptable salt or prodrug thereof, described herein, and one or more additional pharmaceutical agents used in the treatment of epilepsy such as, but not limited to, Dilantin, Luminol, Tegretol, Depakote, Depakene, Zarontin, Neurontin, Barbita, Solfeton, and Felbatol. Also provided are packaged pharmaceutical compositions containing a pharmaceutical composition comprising at least one compound, or pharmaceutically acceptable salt or prodrug thereof, described herein, and another composition comprising one or more additional pharmaceutical agents used in the treatment of epilepsy such as, but not limited to, Dilantin, Luminol, Tegretol, Depakote, Depakene, Zarontin, Neurontin, Barbita, Solfeton, and Felbatol.

Also provided are methods for treating memory and/or cognitive impairment associated with multiple sclerosis comprising administering to a subject, simultaneously or sequentially, at least one compound, or pharmaceutically acceptable salt or prodrug thereof, described herein and one or more additional agents used in the treatment of multiple sclerosis such as, but not limited to, Detrol, Ditropan XL, OxyContin, Betaseron, Avonex, Azothioprine, Methotrexate, and Copaxone. In methods using simultaneous administration, the agents can be present in a combined composition or can be administered separately. Also provided are pharmaceutical compositions comprising at least one compound, or pharmaceutically acceptable salt or prodrug thereof, described herein, and one or more additional pharmaceutical agents used in the treatment of multiple sclerosis such as, but not limited to, Detrol, Ditropan XL, OxyContin, Betaseron, Avonex, Azothioprine, Methotrexate, and Copaxone. Also provided are packaged pharmaceutical compositions containing a pharmaceutical composition comprising at least one compound, or pharmaceutically acceptable salt or prodrug thereof, described herein, and another composition comprising one or more additional pharmaceutical agents used in the treatment of multiple sclerosis such as, but not limited to, Detrol, Ditropan XL, OxyContin, Betaseron, Avonex, Azothioprine, Methotrexate, and Copaxone.

When used in combination with one or more additional pharmaceutical agent or agents, the compound, or pharmaceutically acceptable salt or prodrug thereof, described herein may be administered prior to, concurrently with, or following administration of the additional pharmaceutical agent or agents.

The dosages of the compounds described herein depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The compound, or pharmaceutically acceptable salt or prodrug thereof, described herein are typically administered at dosage levels and in a manner customary for KMO inhibitors. For example, the compound, or pharmaceutically acceptable salt or prodrug thereof, described herein can be administered, in single or multiple doses, by oral administration at a dosage level of generally 0.001-100 mg/kg/day, for example, 0.01-100 mg/kg/day, such as 0.1-70 mg/kg/day, for example, 0.5-10 mg/kg/day. Unit dosage forms can contain generally 0.01-1000 mg of at least one compound, or pharmaceutically acceptable salt or prodrug thereof, described herein, for example, 0.1-50 mg of at least one compound, or pharmaceutically acceptable salt or prodrug thereof, described herein. For intravenous administration, the at least one compound, or pharmaceutically acceptable salt or prodrug thereof, described herein can be administered, in single or multiple dosages, at a dosage level of, for example, 0.001-50 mg/kg/day, such as 0.001-10 mg/kg/day, for example, 0.01-1 mg/kg/day. Unit dosage forms can contain, for example, 0.1-10 mg of at least one compound, or pharmaceutically acceptable salt or prodrug thereof, described herein.

A labeled form of a compound, or pharmaceutically acceptable salt or prodrug thereof, described herein can be used as a diagnostic for identifying and/or obtaining compounds that have the function of modulating an activity of KMO as described herein. The compound, or pharmaceutically acceptable salt or prodrug thereof, described herein may additionally be used for validating, optimizing, and standardizing bioassays.

By "labeled" herein is meant that the compound, or pharmaceutically acceptable salt or prodrug thereof, described herein is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In carrying out the procedures of the methods described herein, it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

EXAMPLES

The compounds, pharmaceutically acceptable salts and prodrugs thereof, described herein, compositions, and methods described herein are further illustrated by the following non-limiting examples.

As used herein, the following abbreviations have the following meanings. If an abbreviation is not defined, it has its generally accepted meaning.

CDI=carbonyldiimidazole
DCM=dichloromethane
DME=dimethyl ether
DMEM=Dulbecco's modified Eagle's medium
DMF=N,N-dimethylformamide
DMSO=dimethylsulfoxide
EDC.HCl=1-Ethyl-3-(3-dimethylaminopropyl)carbodiimide hydrochloride
EtOH=ethanol
Et$_2$O=diethylether
EtOAc=ethyl acetate
g=gram
hr=hour
hrs=hours
HOBt=1-Hydroxybenzotriazol
LiHMDS=lithium hexamethyl-disilazide
LC/MS=liquid chromatography/mass spectrometry
mg=milligram
min=minutes
mL=milliliter
mmol=millimoles
mM=millimolar
ng=nanogram
nm=nanometer
nM=nanomolar
PBS=phosphate buffered saline
rt=room temperature
TBME=t-butyl methyl ether
THF=tetrahydrofuran
TMOF=trimethylorthoformate
μL=microliter
μM=micromolar
1 g/1 ml=1 vol

EXPERIMENTAL

Commercially available reagents and solvents (HPLC grade) were used without further purification.

Thin-layer chromatography (TLC) analysis was performed with Kieselgel 60 F$_{254}$ (Merck) plates and visualized using UV light. Microwave reactions were carried out using CEM focussed microwaves.

$^1$H NMR spectra were recorded on a Bruker DRX 500 MHz spectrometer or Bruker DPX 250 MHz spectrometer in deuterated solvents.

Analytical HPLC-MS was performed on Agilent HP1100 and Shimadzu 2010, systems using reverse phase Atlantis dC18 columns (5 μm, 2.1×50 mm), gradient 5-100% B (A=water/0.1% formic acid, B=acetonitrile/0.1% formic acid) over 2 or 3.5 minutes, injection volume 3 μl, flow=1.0 ml/min. UV spectra were recorded at 215 nm using a Waters 2487 dual wavelength UV detector or the Shimadzu 2010 system. Mass spectra were obtained over the range m/z 150 to 850 at a sampling rate of 2 scans per second using Waters ZMD and over m/z 100 to 1000 at a sampling rate of 2 Hz using Electrospray ionisation, by a Shimadzu 2010 LC-MS system, or analytical HPLC-MS was performed on Agilent HP1100 and Shimadzu 2010, systems using reverse phase Water Atlantis dC18 columns (3 μm, 2.1×100 mm), gradient 5-100% B (A=water/0.1% formic acid, B=acetonitrile/0.1% formic acid) over 7 min, injection volume 3 μl, flow=0.6 ml/min. UV spectra were recorded at 215 nm using a Waters 2996 photo diode array or on the Shimadzu 2010 system. Mass spectra were obtained over the range m/z 150 to 850 at a sampling rate of 2 scans per second using Waters ZQ and over m/z 100 to 1000 at a sampling rate of 2 Hz using Electrospray ionisation, by a Shimadzu 2010 LC-MS system. Data were integrated and reported using OpenLynx and OpenLynx Browser software or via Shimadzu PsiPort software.

Method 1

Scheme for Method 1: (+)-(1S,2S)-cyclopropane-1,2-dicarboxylic acid monomethyl ester was Prepared as Described in EP1475385, 2004

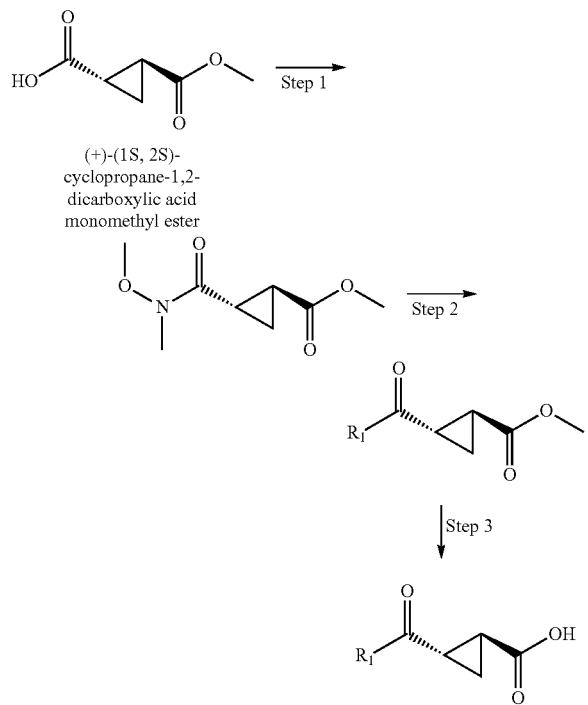

(+)-(1S, 2S)-cyclopropane-1,2-dicarboxylic acid monomethyl ester

Step 1, Method 1: Methyl (1S,2S)-2-[methoxy(methyl)carbamoyl]cyclopropane-1-carboxylate Oxalyl chloride (0.4 mL, 4.6 mmol) was added dropwise over 5 minutes to a round bottomed flask containing (+)-(1S,2S)-cyclopropane-1,2-dicarboxylic acid monomethyl ester (0.1 g, 0.69 mmol) at room temperature under a nitrogen atmosphere and the resulting mixture was stirred for 2 hours. After this time, the reaction mixture was concentrated and the resulting residue was re-dissolved in DCM (1 mL). N,O-Dimethylhydroxylamine (0.08 g, 0.76 mmol) and pyridine (0.12 mL, 1.5 mmol) were then added sequentially to the mixture and the resulting mixture was stirred at room temperature for 18 hours. The mixture was then diluted with DCM (10 mL) and washed sequentially with water (10 mL), saturated sodium bicarbonate (10 mL) and brine (10 mL) before being dried (MgSO$_4$), filtered and concentrated to give the title compound (0.12 g, 92% yield) as a colourless oil which was used directly without further purification.

Step 2, Method 1: Methyl (1S,2S)-2-[(5-chlorothiophen-2-yl)carbonyl]cyclopropane-1-carboxylate 5-Chloro-2-thienyl magnesium bromide (0.5M solution in THF, 1.28 mL, 0.64 mmol) was added dropwise to a cooled (0° C.) solution of methyl (1S,2S)-2-[methoxy(methyl)carbamoyl]cyclopropane-1-carboxylate (0.08 g, 0.43 mmol) in THF (1 mL) under a nitrogen atmosphere. Upon complete addition, the mixture was warmed to room temperature and stirred for 2 hours. After this time the reaction mixture was quenched by the addition of 2M HCl solution (2 mL) and the resulting mixture diluted with water (5 mL) before being extracted with DCM (3×10 mL). The combined organic extracts were washed with brine (10 mL) before being dried (MgSO$_4$), filtered and concentrated. The resulting residue was purified by flash column chromatography (elution: 10% ethyl acetate, 90% heptane) to give the title compound (0.04 g, 40% yield) as a green oil. Tr=2.04 min (3.5 minute method) m/z (ES$^+$) (M+H$^+$) 245.

Intermediate 2, Step 2, Method 1: Methyl (1S,2S)-2-[(Thiophen-3-yl)carbonyl]cyclopropane-1-carboxylate Tr=1.71 min (3.5 minute method) m/z (ES$^+$) (M+H$^+$) 211.

Intermediate 3, Step 2, Method 1: Methyl (1S,2S)-2-[(thiophen-2-yl)carbonyl]cyclopropane-1-carboxylate Tr=1.74 min (3.5 minute method) m/z (ES$^+$) (M+H$^+$) 211.

Step 3, Method 1: (1S,2S)-2-[(5-Chlorothiophen-2-yl)carbonyl]cyclopropane-1-carboxylic acid NaOH (1M solution, 1.0 mL, 1.0 mmol) was added in one portion to a stirred solution of methyl (1S,2S)-2-[(5-chlorothiophen-2-yl)carbonyl]cyclopropane-1-carboxylate (0.04 g, 0.16 mmol) in Methanol (1 mL) and the mixture was stirred at room temperature for 1 hour. After this time, the reaction mixture was partitioned between water (5 mL) and DCM (5 mL). The aqueous layer was removed, acidified to pH 1 with 2M HCl and extracted with DCM (3×5 mL). The combined organic extracts were combined, dried (MgSO$_4$), filtered and concentrated to give the title compound (0.02 g, 51% yield) as a yellow solid.

Example 1, Method 1: (1S,2S)-2-[(5-Chlorothiophen-2-yl)carbonyl]cyclopropane-1-carboxylic acid $\delta_H$ (500 MHz, DMSO) 8.18 (d, J=4.17 Hz, 1H), 7.34 (d, J=4.14 Hz, 1H), 3.17 (ddd, J=3.83, 5.53, 8.94 Hz, 1H), 2.08 (ddd, J=3.79, 5.99, 8.73 Hz, 1H), 1.45 (dddd, J=3.45, 5.76, 8.88, 14.01 Hz, 2H). Tr=3.71 min m/z (ES$^+$) (M+H$^+$) 231.

The following compounds were prepared substantially as described above.

Example 2, Method 1: (1S,2S)-2-[(Thiophen-3-yl)carbonyl]cyclopropane-1-carboxylic acid $\delta_H$ (500 MHz, DMSO) 8.79 (dd, J=1.24, 2.75 Hz, 1H), 7.67 (dd, J=2.79, 5.06 Hz, 1H), 7.53 (dd, J=1.23, 5.07 Hz, 1H), 3.14 (ddd, J=3.82, 5.58, 9.09 Hz, 1H), 2.06 (ddd, J=3.79, 5.88, 8.71 Hz, 1H), 1.43 (dddd, J=3.32, 5.74, 8.80, 14.07 Hz, 2H). Tr=3.12 min m/z (ES$^+$) (M+H$^+$) 197.

Example 3, Method 1: (1S,2S)-2-[(Thiophen-2-yl)carbonyl]cyclopropane-1-carboxylic acid $\delta_H$ (500 MHz, DMSO) 8.22 (dd, J=0.97, 3.82 Hz, 1H), 8.07 (dd, J=0.97, 4.93 Hz, 1H), 7.28 (dd, J=3.89, 4.88 Hz, 1H), 3.17 (ddd, J=3.81, 5.71, 8.56 Hz, 1H), 2.08 (ddd, J=3.77, 6.03, 8.53 Hz, 1H), 1.51-1.38 (m, 2H). Tr=3.13 min m/z (ES$^+$) (M+H$^+$) 197.

| Structure | IUPAC Name | Molecular Weight | LCMS Data | % Inhibition at 30 μM |
|---|---|---|---|---|
| 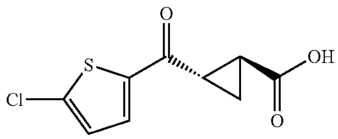 [SMILES: O=C(O)[C@H]1C[C@@H]1C(=O)c1ccc(Cl)s1] | (1S,2S)-2-[(5-Chlorothiophen-2-yl)carbonyl]cyclopropane-1-carboxylic acid | 230 | Tr = 3.71 min m/z (ES+) (M + H+) 231 | 100.7 |
| 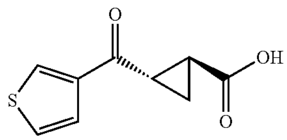 [SMILES: O=C(O)[C@H]1C[C@@H]1C(=O)c1ccsc1] | (1S,2S)-2-[(Thiophen-3-yl)carbonyl]cyclopropane-1-carboxylic acid | 196 | Tr = 3.12 min m/z (ES+) (M + H+) 197 | 83.2 |
| 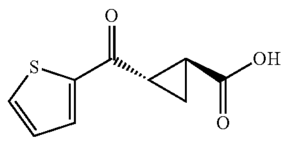 [SMILES: O=C(O)[C@H]1C[C@@H]1C(=O)c1cccs1] | (1S,2S)-2-[(Thiophen-2-yl)carbonyl]cyclopropane-1-carboxylic acid | 196 | Tr = 3.13 min m/z (ES+) (M + H+) 197 | 80.3 |

Method 2

Scheme for Method 2: (+)-(1S, 2S)-cyclopropane-1,2-dicarboxylic acid monomethyl ester was Prepared as Described in EP1475385, 2004

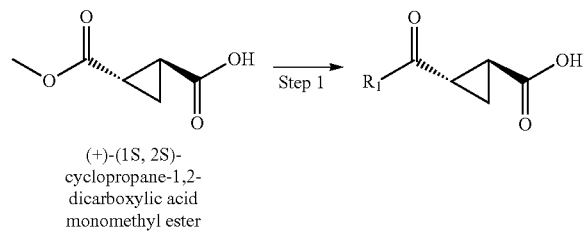

(+)-(1S, 2S)-cyclopropane-1,2-dicarboxylic acid monomethyl ester

Step 1, Method 2: (1S,2S)-2-[(1,3-Thiazol-2-yl)carbonyl]cyclopropane-1-carboxylic acid n-Butyl lithium (1.6M solution in THF, 0.87 mL, 1.4 mmol) was added dropwise over 5 minutes to a cold (−70° C.), stirred solution of 2-bromothiazole (0.23 g, 1.4 mmol) in THF (1 mL) under a nitrogen atmosphere and the mixture was stirred for 30 minutes. After this time, (+)-(1S, 2S)-cyclopropane-1,2-dicarboxylic acid monomethyl ester (0.1 g, 0.69 mmol) in THF (1 mL) was added dropwise over 10 minutes and stirring was continued for 1 hour. After this time the reaction mixture was quenched by the addition of 2M HCl solution (2 mL) and the resulting mixture diluted with water (5 mL) before being extracted with DCM (3×10 mL). The combined organic extracts were dried (MgSO$_4$), filtered and concentrated. The resulting residue was purified by prep HPLC to give the title compound (0.01 g, 4% yield) as a colourless oil.

Example 1, Method 2: (1S,2S)-2-[(1,3-Thiazol-2-yl)carbonyl]cyclopropane-1-carboxylic acid $\delta_H$ (500 MHz, DMSO) 8.28 (d, J=3.01 Hz, 1H), 8.21 (d, J=3.01 Hz, 1H), 3.48 (td, J=3.76, 7.46 Hz, 1H), 2.16-2.03 (m, 1H), 1.58-1.46 (m, 2H). Tr=2.92 min m/z (ES+) (M+H+) 198.

The following compounds were prepared substantially as described above.

Example 2, Method 2: (1S,2S)-2-[(1,3-Benzothiazol-2-yl)carbonyl]cyclopropane-1-carboxylic acid $\delta_H$ (400 MHz, DMSO) 8.29 (ddd, J=1.72, 6.90, 17.74 Hz, 2H), 7.67 (pd, J=1.43, 7.16 Hz, 2H), 3.72-3.59 (m, 1H), 2.26 (td, J=3.82, 7.29 Hz, 1H), 1.73-1.55 (m, 2H). Tr=3.73 min m/z (ES+) (M+H+) 248.

Example 3, Method 2: (1S,2S)-2-[(Pyridin-2-yl)carbonyl]cyclopropane-1-carboxylic acid $\delta_H$ (400 MHz, CDCl$_3$) 8.76 (d, J=4.10 Hz, 1H), 8.05 (d, J=7.82 Hz, 1H), 7.88 (td, J=1.67, 7.71 Hz, 1H), 7.54 (ddd, J=1.24, 4.81, 7.52 Hz, 1H), 4.12-3.94 (m, 1H), 2.36 (s, OH), 1.86-1.57 (m, 2H). Tr=2.82 min m/z (ES+) (M+H+) 192.

| Structure | IUPAC Name | Molecular Weight | LCMS Data | % Inhibition at 30 μM |
|---|---|---|---|---|
| 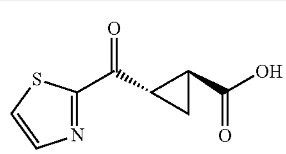 [SMILES: O=C(O)[C@H]1C[C@@H]1C(=O)c1nccs1] | (1S,2S)-2-[(1,3-Thiazol-2-yl)carbonyl]cyclopropane-1-carboxylic acid | 197 | Tr = 2.92 min m/z (ES+) (M + H+) 198 | 28.7 (at 10 uM) |

-continued

| Structure | IUPAC Name | Molecular Weight | LCMS Data | % Inhibition at 30 μM |
|---|---|---|---|---|
| 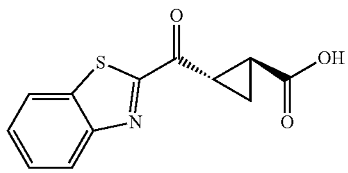 [SMILES: O=C(O)[C@H]1C[C@@H]1C(=O)c1nc2ccccc2s1] | (1S,2S)-2-[(1,3-Benzothiazol-2-yl)carbonyl]cyclopropane-1-carboxylic acid | 247 | Tr = 3.73 min m/z (ES⁺) (M + H⁺) 248 | 91.8 |
| 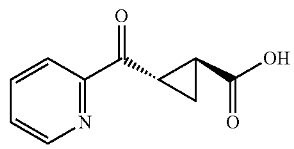 [SMILES: O=C(O)[C@H]1C[C@@H]1C(=O)c1ccccn1] | (1S,2S)-2-[(Pyridin-2-yl)carbonyl]cyclopropane-1-carboxylic acid | 191 | Tr = 2.82 min m/z (ES⁺) (M + H⁺) 192 | 45.6 |

Method 3

Scheme for Method 3: (1S,2S)-2-(2-Methyl-1,3-benzothiazole-6-carbonyl)cyclopropane-1-carboxylic acid

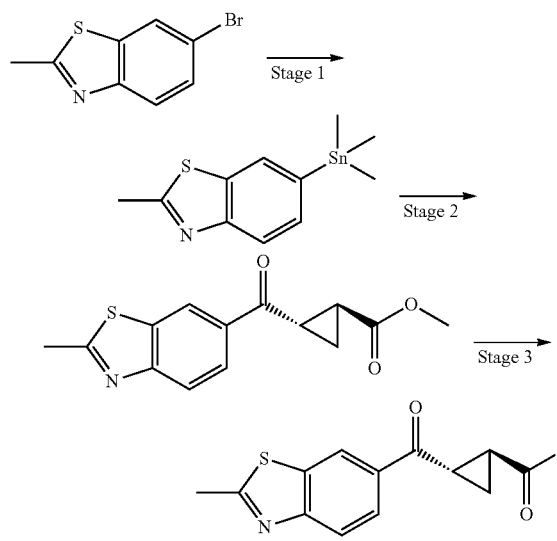

Step 1, Method 3:
2-Methyl-6-(trimethylstannyl)-1,3-benzothiazole

6-Bromo-2-methyl-1,3-benzothiazole (820 mg, 3.60 mmol) and lithium chloride (170 mg, 3.95 mmol) were dissolved in anhydrous dioxane (10 ml) and degassed with nitrogen for 5 min. Hexamethyldistannane (0.82 ml, 3.95 mmol) and Pd(PPh₃)₄ (210 mg, 1.18 mmol) were added and the reaction was stirred at 100° C. for 1 h. The dark reaction mixture was cooled to room temperature and concentrated to give a black residue. Column chromatography (eluent: 0-15% EtOAc-heptane) afforded the title compound as an orange oil (906 mg, 76%). δ$_H$ (500 MHz, CDCl₃) 8.00-7.85 (m, 2H), 7.61-7.48 (m, 1H), 2.84 (s, 3H), 0.43-0.25 (m, 9H). Tr=2.47 min m/z (ES⁺) (M+H⁺) 314, 316.

Intermediate 2, Step 1, Method 3:
5-Chloro-7-(trimethylstannyl)quinoxaline

δ$_H$ (500 MHz, DMSO-d6) 8.94 (d, J=1.64 Hz, 1H), 8.90 (d, J=1.56 Hz, 1H), 8.27-8.11 (m, 1H), 8.10-7.85 (m, 1H), 0.60-0.24 (m, 9H).. Tr=2.20 min m/z (ES⁺) (M+H⁺) 325, 327, 329, 331, 333.

Intermediate 3, Step 1, Method 3:
8-Chloro-6-(trimethylstannyl)quinoline

Tr=2.40 min m/z (ES⁺) (M+H⁺) 326, 328, 330.

Step 2, Method 3: Methyl (1S,2S)-2-(2-methyl-1,3-benzothiazole-6-carbonyl)cyclopropane-1-carboxylate 2-Methyl-6-(trimethylstannyl)-1,3-benzothiazole (94% purity, 902 mg, 2.89 mmol) and methyl (1S,2S)-2-(carbonochloridoyl)cyclopropane-1-carboxylate (470 mg, 2.89 mmol) were dissolved in anhydrous toluene (20 ml) and de-oxygenated with stream of nitrogen for 5 min. PdCl₂(PPh₃)₂ (101 mg, 0.145 mmol) was added and the reaction was stirred at 110° C. under nitrogen for 2 h. The reaction mixture was cooled to room temperature and concentrated to afford a black residue. Column chromatography (eluent 0-80% EtOAc-heptane) afforded the title compound as an orange oil (486 mg, 55%). δ$_H$ (500 MHz, DMSO-d6) 8.93 (d, J=1.6 Hz, 1H), 8.10 (dd, J=8.6, 1.8 Hz, 1H), 8.02 (d, J=8.5 Hz, 1H), 3.68 (s, 3H), 3.46-3.36 (m, 1H), 2.86 (s, 3H), 2.26 (ddd, J=8.6, 5.9, 3.9 Hz, 1H), 1.56 (dtd, J=11.0, 5.8, 2.9 Hz, 2H). Tr=1.88 min m/z (ES⁺) (M+H⁺) 276.

Intermediate 2, Step 2, Method 3: Methyl (1S,2S)-2-(8-chloroquinoxaline-6-carbonyl)cyclopropane-1-carboxylate δ$_H$ (500 MHz, DMSO-d6) 9.06 (d, J=1.72 Hz, 1H), 9.02 (d, J=1.68 Hz, 1H), 8.75 (d, J=1.78 Hz, 1H), 8.45 (d, J=1.81 Hz, 1H), 3.77 (s, 3H), 3.34 (ddd, J=3.84, 5.94, 8.27 Hz, 1H), 2.49 (ddd, J=3.81, 6.29, 8.62 Hz, 1H), 1.73 (ddd, J=3.19, 6.17, 11.35 Hz, 2H). Tr=1.98 min m/z (ES⁺) (M+H⁺) 291, 293.

Intermediate 3, Step 2, Method 3: Methyl (1S,2S)-2-(8-chloroquinoline-6-carbonyl)cyclopropane-1-carboxylate δ$_H$ (500 MHz, DMSO-d6) 9.16 (dd, J=4.26, 1.73 Hz, 1H) 9.01 (d, J=1.73 Hz, 1H) 8.72 (dd, J=8.28, 1.65 Hz, 1H) 8.34 (d, J=1.89 Hz, 1H) 7.80 (dd, J=8.28, 4.18 Hz, 1H) 3.61-3.79 (m, 3H) 3.50 (ddd, J=8.91, 5.44, 3.94 Hz, 1H) 2.29-2.38 (m, 1H) 1.50-1.69 (m, 2H). Tr=1.78 min m/z (ES⁺) (M+H⁺) 290, 292.

Step 3, Method 3: (1S,2S)-2-(2-Methyl-1,3-benzo-thiazole-6-carbonyl)cyclopropane-1-carboxylic acid Methyl (1S,2S)-2-(2-methyl-1,3-benzothiazole-6-carbonyl)cyclopropane-1-carboxylate (50 mg, 0.182 mmol) was dissolved in dioxane (3 ml) and treated with 2M NaOH (82 μl, 0.163 mmol). The reaction mixture was stirred at rt for 72 h. The reaction mixture was evaporated to dryness and the resulting residue dissolved in water (2 ml). The aqueous layer was washed with TBME (2×1 ml) and DCM (2×1 ml). The aqueous layer was acidified to pH 1 using 2M HCl, and then extracted with EtOAc (2×3 ml). The combined organic layers were washed with water (2 ml), dried using $MgSO_4$, filtered and evaporated to give a brown solid. The solid was triturated in 1 ml MeCN/water to afford the title compound as a brown solid. (7 mg, 15%).

Example 1, Method 3: (1S,2S)-2-(2-Methyl-1,3-benzothiazole-6-carbonyl)cyclopropane-1-carboxylic acid $\delta_H$ (500 MHz, DMSO-d6) 12.66 (s, 1H), 8.95-8.90 (m, 1H), 8.09 (d, J=8.5 Hz, 1H), 8.02 (d, J=8.5 Hz, 1H), 3.30 (obscured. m, 1H), 2.86 (s, 3H), 2.17-2.10 (m, 1H), 1.50 (dt, J=8.7, 4.3 Hz, 2H). Tr=2.19 min; m/z (M+H$^+$) 262.

The following examples were prepared using the method described above:

Example 2, Method 3: (1S,2S)-2-(8-Chloroquinoxaline-6-carbonyl)cyclopropane-1-carboxylic acid $\delta_H$ (500 MHz, DMSO-d6) 9.17 (s, 2H), 8.65 (d, J=1.61 Hz, 1H), 8.34 (d, J=1.52 Hz, 1H), 3.10 (dq, J=3.82, 6.66 Hz, 1H), 1.84 (td, J=3.76, 7.75 Hz, 1H), 1.42-1.29 (m, 2H). Tr=2.18 min m/z (M+H$^+$) 277, 279.

Example 3, Method 3: (1S,2S)-2-(8-Chloroquinoline-6-carbonyl)cyclopropane-1-carboxylic acid $\delta_H$ (500 MHz, $D_2O$) 8.68 (dd, J=4.41, 1.58 Hz, 1H) 8.14 (dd, J=8.35, 1.42 Hz, 1H) 8.07 (d, J=1.73 Hz, 1H) 7.74 (d, J=1.73 Hz, 1H) 7.46 (dd, J=8.28, 4.33 Hz, 1H) 2.97-3.07 (m, 1H) 2.08-2.20 (m, 1H) 1.47-1.60 (m, 2H). Tr=2.26 min m/z (M+H$^+$) 276, 278.

Method 4

Scheme for Method 4: (1S,2S)-2-(7-Chloro-1-benzofuran-5-carbonyl)cyclopropane-1-carboxylic acid

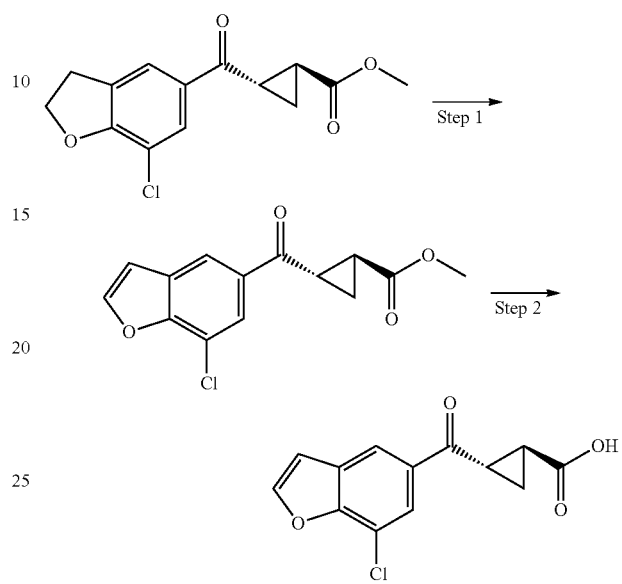

Step 1, Method 4: Methyl-(1S,2S)-2-(7-chloro-1-benzofuran-5-carbonyl)cyclopropane-1-carboxylate Methyl (1S,2S)-2-(7-chloro-2,3-dihydro-1-benzofuran-5-carbonyl)cyclopropane-1-carboxylate (0.42 g, 1.49 mmol), and DDQ (0.35 g, 1.56 mmol) were suspended in anhydrous toluene (20 mL) and stirred at reflux under a nitrogen atmosphere for 24 hours. After this time the reaction was cooled to room temperature and another 0.5 eq of DDQ

| Structure | IUPAC Name | Molecular Weight | LCMS Data | % Inhibition at 30 μM |
|---|---|---|---|---|
| 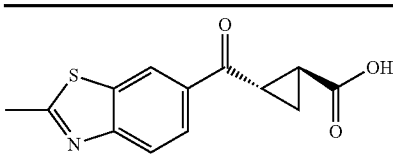 | (1S,2S)-2-(2-methyl-1,3-benzothiazole-6-carbonyl)cyclopropane-1-carboxylic acid | 261 | Tr = 2.19 min m/z (ES+) (M + H+) 262 | 74.5 |
| 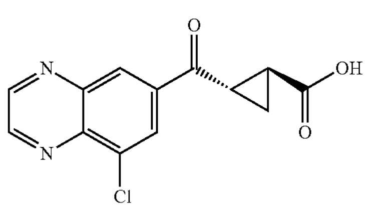 [SMILES: O=C(O)[C@H]1C[C@@H]1C(=O)c1cc(Cl)c2nccnc2c1] | (1S,2S)-2-(8-chloroquinoxaline-6-carbonyl)cyclopropane-1-carboxylic acid | 276 | Tr = 2.18 min m/z (ES+) (M + H+) 277/279 | 100.6 |
| 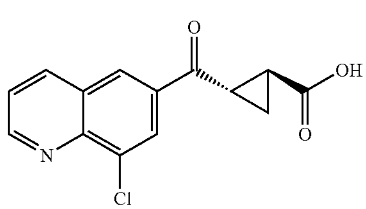 [SMILES: O=C(O)[C@H]1C[C@@H]1C(=O)c1cc(Cl)c2ncccc2c1] | (1S,2S)-2-(8-chloroquinoline-6-carbonyl)cyclopropane-1-carboxylic acid | 275 | Tr = 2.26 min m/z (ES+) (M + H+) 276/278 | 100.5 |

(0.17 g, 0.74 mmol) was added and the reaction was heated to reflux for a further 24 hours. The reaction mixture was cooled to room temperature and the reaction mixture was concentrated. The resulting residue was dry loaded onto silica and loaded onto a 50 g isolute cartridge and purified by Biotage, eluting the product in 0-30% ethyl acetate in heptanes over 12 CV. The resulting purified fractions were combined, concentrated and re-dissolved in 1.5 mL of DMSO:MeCN (2:1) before being purified by Prep HPLC (Low pH: MeCN +0.1% Formic Acid) to give the title compound (0.05 g, 11% yield) as a pale brown gum. $\delta_H$ (500 MHz, CDCl$_3$) 8.23 (d, J=1.5 Hz, 1H), 8.01 (d, J=1.4 Hz, 1H), 7.78 (d, J=2.1 Hz, 1H), 6.93 (d, J=2.2 Hz, 1H), 3.75 (s, 3H), 3.21 (ddd, J=9.4, 5.7, 3.9 Hz, 1H), 2.43 (ddd, J=8.9, 5.9, 3.8 Hz, 1H), 1.65 (dddd, J=17.9, 9.3, 5.8, 3.5 Hz, 2H). Tr=2.18 min m/z (ES+) (M+H$^+$) 279.

Step 2, Method 4: (1S,2S)-2-(7-Chloro-1-benzofuran-5-carbonyl)cyclopropane-1-carboxylic acid 2M NaOH solution (0.14 mL) was added in one portion to a stirred solution of methyl (1S,2S)-2-(7-chloro-1-benzofuran-5-carbonyl)cyclopropane-1-carboxylate (0.039 g, 0.14 mmol) in 1,4-Dioxane (1 mL) and the resulting reaction mixture was stirred for 5 hours at room temperature. After this time the reaction mixture was acidified using ~1 ml of 2M HCl, adjusting the pH to 1, the reaction mixture was then taken up into ethyl acetate (15 mL), washed with water (2×5 mL) and the aqueous extracted again with ethyl acetate (15 mL). The organic layer was dried (MgSO$_4$), filtered and concentrated to give the title compound (0.03 g, 89% yield) as a white solid.

Example 1, Method 4: (1S,2S)-2-(7-Chloro-1-benzofuran-5-carbonyl)cyclopropane-1-carboxylic acid $\delta_H$ (500 MHz, CDCl$_3$) 0.23 (d, J=1.2 Hz, 1H), 8.01 (s, 1H), 7.78 (d, J=2.0 Hz, 1H), 6.94 (d, J=2.2 Hz, 1H), 3.27 (ddd, J=9.3, 5.8, 3.9 Hz, 1H), 2.44 (ddd, J=9.1, 5.7, 3.9 Hz, 1H), 1.71 (dddd, J=22.5, 9.1, 5.7, 3.6 Hz, 2H). Tr=2.87 min (7 minute method, low pH) m/z (ES+) (M+H$^+$) 264.

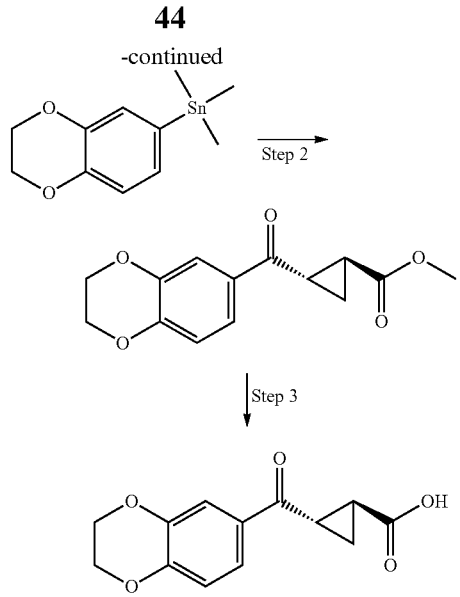

Step 1, Method 5:
2,3-Dihydro-1,4-benzodioxin-6-yltrimethylstannane n-Butyllithium (3.1 ml of a 1.6M solution in hexane, 4.98 mmol) was added dropwise under nitrogen to a stirred solution of 6-bromo-2,3-dihydro-1,4-benzodioxine (1.00 g, 4.65 mmol) in dry THF (20 ml) at −78° C. After 45 min, trimethyltin chloride (5.0 ml of a 1.0M solution in THF, 5 mmol) was added dropwise over 5 min. After 20 min the reaction mixture was allowed to warm to room temperature and left overnight. The reaction mixture was poured into brine (100 ml), extracted with ethyl acetate (3×80 ml) and the combined, dried (Na$_2$SO$_4$) organic extracts were evaporated in vacuo to give the title compound (1.363 g, 98%). as a colourless oil. $\delta_H$ (500 MHz, CDCl$_3$) 6.78 (d, J=1.1 Hz, 1H), 6.74 (dd, J=7.7, 1.1 Hz, 1H), 6.67 (d, J=7.7 Hz, 1H), 4.06 (s, 4H), 0.06 (s, 9H). Tr=2.42 min; no ionisation.

| Structure | Molecular Weight | IUPAC Name | LCMS Data | % Inhibition at 30 μM |
|---|---|---|---|---|
| 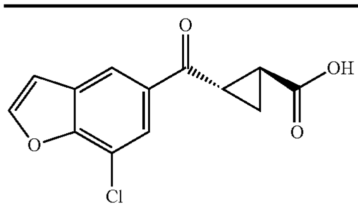 | 264.661 | (1S,2S)-2-(7-chloro-1-benzofuran-5-carbonyl)cyclopropane-1-carboxylic acid | Tr = 2.87 min m/z (ES+) (M + H+) 264 | 100.4 |

Method 5 (Modified Stannane Formation)

Scheme for Method 5

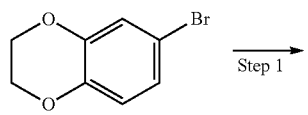

Intermediate 2, Step 1, Method 5:
2-Methyl-6-(trimethylstannyl)-1,3-benzothiazole $\delta_H$ NMR (500 MHz, Chloroform-d) 8.00-7.85 (m, 2H), 7.61-7.48 (m, 1H), 2.84 (s, 3H), 0.43-0.25 (m, 9H). Tr=2.47 min m/z (ES$^+$) (M+H$^+$) 314/316.

Intermediate 3, Step 1, Method 5:
3,4-Dihydro-2H-1-benzopyran-6-yltrimethylstannane $\delta_H$ NMR (500 MHz, Chloroform-d) 7.21 (d, J=7.9 Hz, 1H), 7.15 (s, 1H), 6.81 (d, J=7.9 Hz, 1H), 4.21-4.17 (m, 2H), 2.80 (t, J=6.6 Hz, 2H), 2.05-2.00 (m, 2H), 0.26 (s, 9H). Tr=2.59 min, 62% pure, compound doesn't ionise).

Step 2, Method 5: Methyl (1S,2S)-2-(2,3-dihydro-1,4-benzodioxine-6-carbonyl)cyclopropane-1-carboxylate A mixture of 2,3-dihydro-1,4-benzodioxin-6-yltrimethylstannane (700 mg, 2.34 mmol), (1S,2S)-2-(methoxycarbonyl)cyclopropane-1-carboxylic acid (571 mg, 3.51 mmol), PdCl$_2$(PPh$_3$)$_2$ (82 mg, 0.12 mmol), and toluene (8 mL) was de-gassed by bubbling a stream of nitrogen through the mixture for 15 min, and then stirred at 110° C. for 2 h. The reaction was cooled, and then absorbed onto silica gel (Merck 9385, 8 mL). The resultant silica was purified on a Biotage machine (100 g cartridge of silica gel) eluting with ethyl acetate-heptane (5% EtOAc, 1CV; 5% to 40% EtOAc 10 CV; 40% EtOAc, 2 CV), to give the desired product (373 mg, 58%) as pale yellow oil. $\delta_H$ (500 MHz, CDCl$_3$) 7.61-7.57 (m, 2H), 7.00-6.86 (m, 1H), 4.33 (ddd, J=20.0, 5.8, 2.6 Hz, 4H), 3.13 (ddd, J=9.4, 5.8, 3.9 Hz, 1H), 2.36 (ddd, J=9.5, 5.8, 3.9 Hz, 1H), 1.59 (dddd, J=25.1, 9.1, 5.8, 3.4 Hz, 2H).). Tr=1.86 min; 100% m/z (ES+) 263 (M+H$^+$).

Intermediate 2, Step 2, Method 5: Methyl (1S,2S)-2-(2-methyl-1,3-benzothiazole-6-carbonyl)cyclopropane-1-carboxylate $\delta_H$ NMR (500 MHz, DMSO-d6) 8.93 (d, J=1.6 Hz, 1H), 8.10 (dd, J 8.6, 1.8 Hz, 1H), 8.02 (d, J=8.5 Hz, 1H), 3.68 (s, 3H), 3.46-3.36 (m, 1H), 2.86 (s, 3H), 2.26 (ddd, J=8.6, 5.9, 3.9 Hz, 1H), 1.56 (dtd, J=11.0, 5.8, 2.9 Hz, 2H). Tr=1.88 min m/z (ES$^+$) 276 (M+H)$^+$.

Intermediate 3, Step 2, Method 5: 3,4-Dihydro-2H-1-benzopyran-6-yltrimethylstannane $\delta_H$ NMR (500 MHz, Chloroform-d) 7.80 (dd, J=8.5, 2.2 Hz, 1H), 7.77 (d, J=2.0 Hz, 1H), 6.85 (d, J=8.5 Hz, 1H), 4.29-4.23 (m, 2H), 3.74 (s, 3H), 3.14 (ddd, J=8.8, 5.8, 3.9 Hz, 1H), 2.85 (t, J=6.4 Hz, 2H), 2.36 (ddd, J=8.7, 5.8, 3.8 Hz, 1H), 2.09-2.01 (m, 2H), 1.58 (dddd, J=27.0, 9.0, 5.8, 3.4 Hz, 2H). Tr=1.90 min m/z (ES+) 261 (M+H)$^+$.

Step 3, Method 5: (1S,2S)-2-(2,3-Dihydro-1,4-benzodioxine-6-carbonyl)cyclopropane-1-carboxylic acid A solution of methyl (1S,2S)-2-(2,3-dihydro-1,4-benzodioxine-6-carbonyl)cyclopropane-1-carboxylate (347 mg, 1.32 mmol) in 1,4-dioxane (8 ml) was treated with aqueous 2M sodium hydroxide (595 µl, 1.19 mmol) at room temperature, and stirred for 22 h under nitrogen. The reaction mixture was evaporated in vacuo, treated with water (25 ml), extracted with ether (3×30 ml), and the ethereal extracts were discarded. The aqueous phase was filtered through a PTFE frit (0.45 µM). The aqueous solution was freeze-dried to give a foam (300 mg). A solution of the foam in DMSO (3 ml) was treated with aqueous 2M hydrochloric acid (0.6 ml) and purified by low pH HPLC. The resultant gum was further dried in vacuo at 40° C. to give the title compound (104 mg, 31%) as a colourless gum.

Example 2, Method 5: (1S,2S)-2-(2-Methyl-1,3-benzothiazole-6-carbonyl)cyclopropane-1-carboxylic acid $\delta_H$ NMR (500 MHz, DMSO-d6) 12.66 (s, 1H), 8.95-8.90 (m, 1H), 8.09 (d, J=8.5 Hz, 1H), 8.02 (d, J=8.5 Hz, 1H), 3.30 (obscured. m, 1H), 2.86 (s, 3H), 2.17-2.10 (m, 1H), 1.50 (dt, J=8.7, 4.3 Hz, 2H). Tr=2.19 min; m/z (ES+) 262 (M+H)$^+$.

| Structure | IUPAC Name | Molecular Weight | LCMS Data | % Inhibition at 30 µM |
|---|---|---|---|---|
| 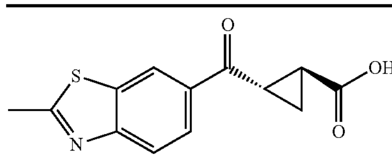 | 261.3 | (1S,2S)-2-(2-methyl-1,3-benzothiazole-6-carbonyl)cyclopropane-1-carboxylic acid | Tr = 2.19 min m/z (ES+) (M + H+) 262 | 98.3 |

Method 6

Scheme for Method 6

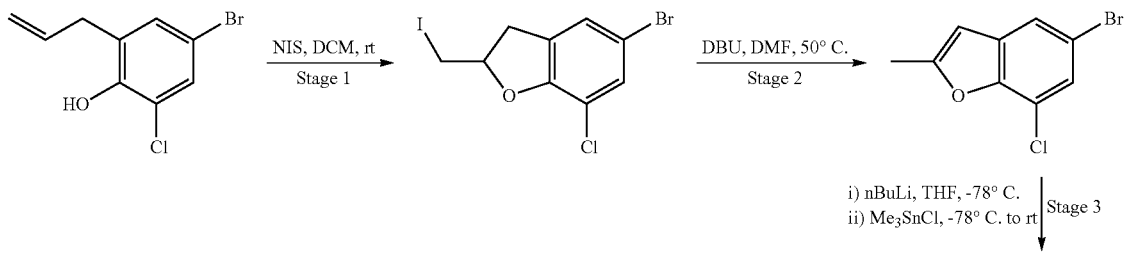

i) nBuLi, THF, -78° C.
ii) Me$_3$SnCl, -78° C. to rt   Stage 3

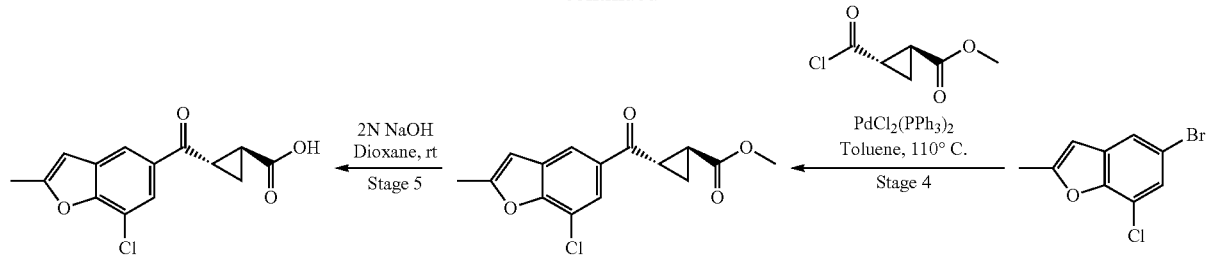

Step 1, Method 6: 5-Bromo-7-chloro-2-(iodomethyl)-2,3-dihydro-1-benzofuran

N-Iodosuccinimide (5.85 g, 26.0 mmol) was added to a solution of 4-bromo-2-chloro-6-(prop-2-en-1-yl)phenol (86%, 4.99 g, 17.34 mmol) in DCM (50 mL). The reaction mixture was stirred at room temperature for 17.5 hours, washed with a saturated aqueous solution of sodium thiosulfate (2×20 mL), dried (MgSO4), filtered and concentrated under reduced pressure to leave a thick orange oil (7.25 g). Purification by column chromatography (Biotage, 1-10% EtOAc in heptane Rf=0.29 in 5% EtOAc in heptane) afforded the title compound as a pale yellow oil (3.07 g, 38% yield), which was used in the next step without further purification. $\delta_H$ NMR (500 MHz, Chloroform-d) 7.29-7.27 (m, 1H), 7.18-7.15 (m, 1H), 4.97 (dddd, J=9.0, 8.1, 6.7, 4.1 Hz, 1H), 3.52-3.42 (m, 2H), 3.36 (dd, J=10.2, 8.1 Hz, 1H), 3.13 (dd, J=16.3, 6.6 Hz, 1H). Tr=2.34 min, no mass ion.

Step 2, Method 6: 5-Bromo-7-chloro-2-methyl-1-benzofuran

DBU (1.0 mL, 7.9 mmol) was added to a solution of 5-bromo-7-chloro-2-(iodomethyl)-2,3-dihydro-1-benzofuran (80%, 3.07 g, 6.6 mmol) in anhydrous DMF (30 mL). The reaction mixture was stirred at 50° C. under nitrogen for 16 hours, allowed to cool to room temperature and partitioned between water (50 mL) and EtOAc (50 mL). The aqueous layer was separated and extracted further with EtOAc (2×50 mL). The combined organic extracts were washed with water (2×50 mL), brine (50 mL), dried (MgSO$_4$), filtered and concentrated under reduced pressure to leave a sticky orange solid (2.01 g). Purification by column chromatography (Biotage, heptane, Rf=0.43 in heptane) afforded the title compound as a white solid (1.38 g, 100% purity, 85% yield). $\delta_H$ NMR (500 MHz, Chloroform-d) 7.49 (d, J=1.7 Hz, 1H), 7.34 (d, J=1.8 Hz, 1H), 6.38-6.35 (m, 1H), 2.49 (d, J=0.8 Hz, 3H). Tr=2.37 min, no mass ion.

Step 3, Method 6: (7-Chloro-2-methyl-1-benzofuran-5-yl)trimethylstannane n-Butyllithium (3.9 mL of a 1.6M solution in hexanes, 6.2 mmol) was added dropwise over 15 minutes to a cold (−78° C.) solution of 5-bromo-7-chloro-2-methyl-1-benzofuran (1.38 g, 5.62 mmol) in anhydrous THF (20 mL) under a nitrogen atmosphere. The reaction mixture was stirred for 45 minutes and chloro(trimethyl)stannane (1M solution in THF, 6.2 mL, 6.2 mmol) was added dropwise over 15 minutes. After 20 minutes, the reaction mixture was allowed to warm to room temperature, stirred for 22 hours and poured in brine (50 mL). The aqueous layer was separated and extracted further with EtOAc (2×50 mL). The combined organic extracts were washed with brine (50 mL), dried (MgSO$_4$), filtered and concentrated under reduced pressure to leave a yellow oil (1.72 g). Purification by column chromatography (Biotage, heptane, Rf=0.28 in heptane) afforded the title compound as a colourless oil (1.12 g, 50% yield), which was used in the next step without further purification. $\delta_H$ NMR (500 MHz, Chloroform-d) 7.45 (s, 1H), 7.26 (s, 1H), 6.38 (d, J=1.0 Hz, 1H), 2.49 (d, J=0.8 Hz, 3H), 0.32 (s, 9H). Tr=2.72 min, no mass ion.

Step 4, Method 6: Methyl (1S,2S)-2-(7-chloro-2-methyl-1-benzofuran-5-carbonyl)cyclopropane-1-carboxylate A solution of (7-chloro-2-methyl-1-benzofuran-5-yl)trimethylstannane (82%, 1.12 g, 2.79 mmol) and (1S,2S)-2-(carbonochloridoyl)cyclopropane-1-carboxylate (718 mg, 4.42 mmol) in anhydrous toluene (10 mL) was degassed for 20 minutes by bubbling nitrogen. PdCl$_2$(PPh$_3$)$_2$ (98 mg, 0.14 mmol) was added. The reaction mixture was stirred at 110° C. under an atmosphere of nitrogen for 3 hours, allowed to cool to room temperature and concentrated under reduced pressure to leave a brown oil (618 mg). Purification by column chromatography (Biotage, 5-40% EtOAc in heptane, Rf=0.29 in 20% EtOAc in heptane) afforded the title compound as a pale yellow oil (618 mg, 65% yield), which was used in the next step without further purification. Tr=2.15 min m/z (ES$^+$) (M+H$^+$) 293, 295.

Step 5, Method 6: (1S,2S)-2-(7-chloro-2-methyl-1-benzofuran-5-carbonyl)cyclopropane-1-carboxylic acid 2M Sodium hydroxide (1.8 mL, 3.6 mmol) was added to a solution of methyl (1S,2S)-2-(7-chloro-2-methyl-1-benzofuran-5-carbonyl)cyclopropane-1-carboxylate (86%, 618 mg, 1.82 mmol) in dioxane (5 mL) and the reaction mixture was stirred at room temperature for 3 hours. 2N HCl (1.8 mL, 3.6 mmol) was added and the reaction mixture was concentrated under reduced pressure to leave a pale yellow solid. Trituration with MeCN (3 mL) afforded a white solid (383 mg), which was filtered-off and discarded. The filtrate was concentrated under reduced pressure to leave an-off white solid (383 mg), which was purified by acidic preparative HPLC to afford the title compound as a white solid (214 mg, 42% yield).

Example 1, Method 6: (1S,2S)-2-(7-chloro-2-methyl-1-benzofuran-5-carbonyl)cyclopropane-1-carboxylic acid $\delta_H$ NMR (500 MHz, Chloroform-d) 8.08 (d, J=1.5 Hz, 1H), 7.92 (d, J=1.5 Hz, 1H), 6.52 (d, J=1.0 Hz, 1H), 3.25 (ddd, J=9.5, 5.9, 3.8 Hz, 1H), 2.54 (d, J=0.8 Hz, 3H), 2.46-2.39 (m, 1H), 1.69 (dddd, J=23.4, 9.2, 5.8, 3.6 Hz, 2H). Tr=3.14 min m/z (ES$^+$) (M+H$^+$) 279, 281.

| Structure | IUPAC Name | Molecular Weight | LCMS Data | % Inhibition at 30 μM |
|---|---|---|---|---|
| | (1S,2S)-2-(7-chloro-2-methyl-1-benzofuran-5-carbonyl)cyclopropane-1-carboxylic acid | 278.69 | Tr = 3.14 min m/z (ES+) (M + H+) 279/281 | 102.4 |

Method 7

The following routes (A, B, C, D, E & F) describe methods for the synthesis of compounds described in the table below. "Ar" refers to $R_1$.

Route A:

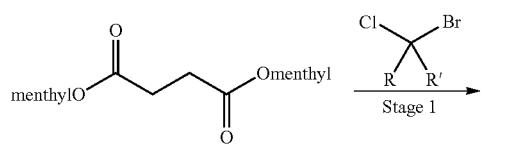

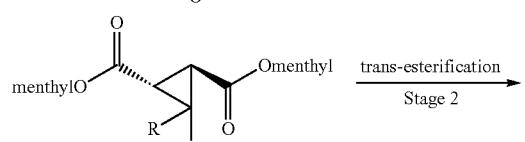 trans-esterification Stage 2

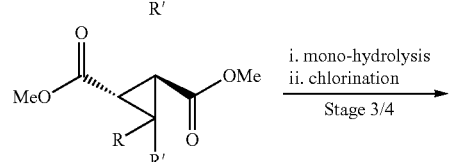 i. mono-hydrolysis ii. chlorination Stage 3/4

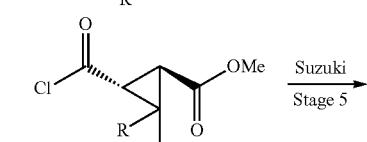 Suzuki Stage 5

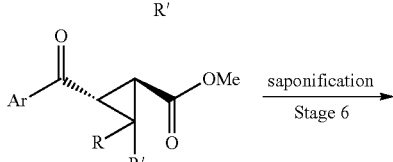 saponification Stage 6

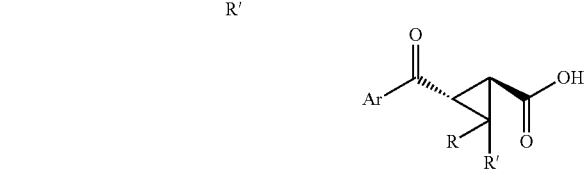

Route B:

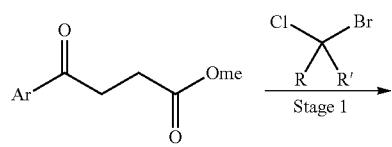 Stage 1

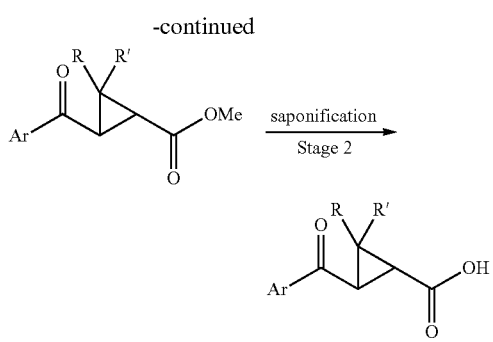 saponification Stage 2

Route C:

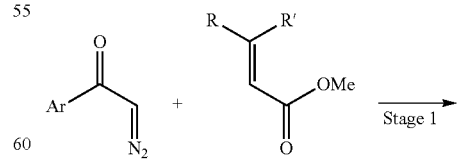 Stage 1 saponification Stage 2

Route D:

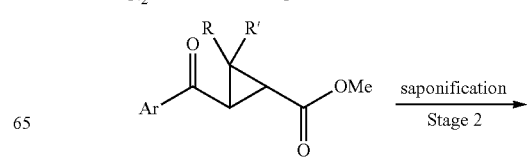 saponification Stage 2

Route E:

Route F:

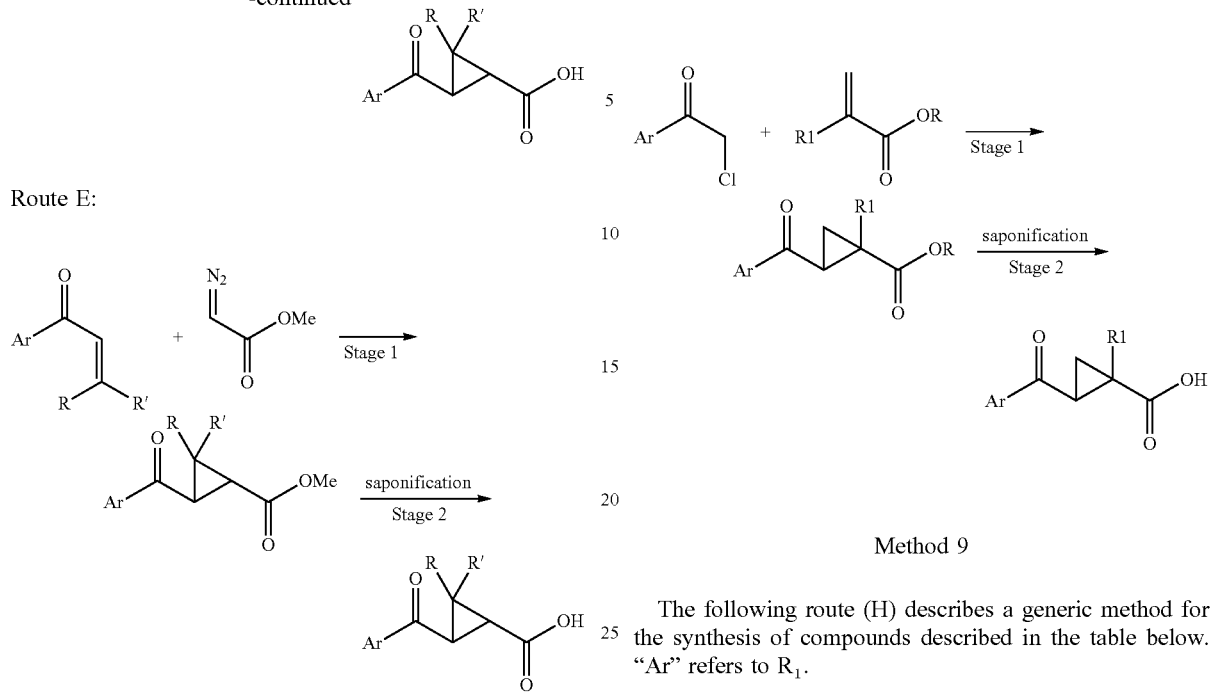

Method 8

The following route (G) describes a generic method for the synthesis of compounds described in the table below. "Ar" refers to $R_1$.

Route G:

Route H:

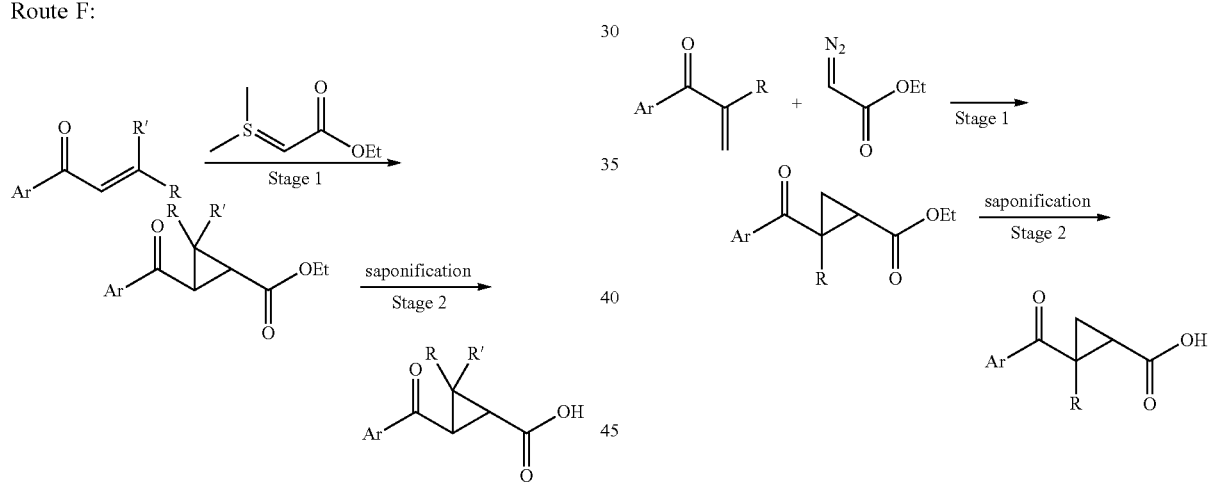

Method 9

The following route (H) describes a generic method for the synthesis of compounds described in the table below. "Ar" refers to $R_1$.

Prophetic Examples

The following examples may be prepared using the methods described above, and are expected to have activity against KMO and in the treatment of KMO-mediated diseases such as those disclosed herein.

| Structure | IUPAC Name |
|---|---|
| 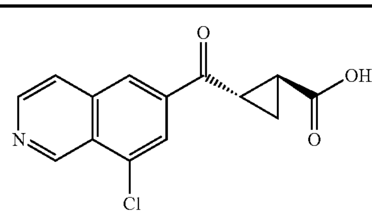 | (1S,2S)-2-(8-chloroisoquinoline-6-carbonyl)cyclopropanecarboxylic acid |

-continued

| Structure | IUPAC Name |
| --- | --- |
| 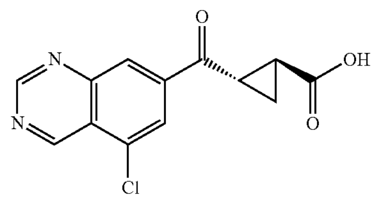 [SMILES: O=C(O)[C@H]1C[C@@H]1C(=O)c1cc(Cl)c2cncnc2c1] | (1S,2S)-2-(5-chloroquinazoline-7-carbonyl)cyclopropanecarboxylic acid |
| 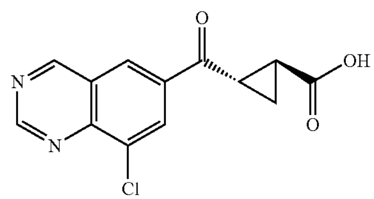 [SMILES: O=C(O)[C@H]1C[C@@H]1C(=O)c1cc(Cl)c2ncncc2c1] | (1S,2S)-2-(8-chloroquinazoline-6-carbonyl)cyclopropanecarboxylic acid |
| 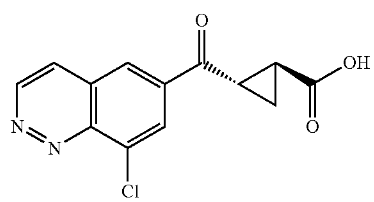 [SMILES: O=C(O)[C@H]1C[C@@H]1C(=O)c1cc(Cl)c2nnccc2c1] | (1S,2S)-2-(8-chlorocinnoline-6-carbonyl)cyclopropanecarboxylic acid |
| 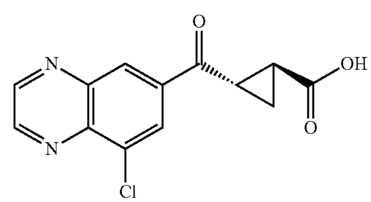 [SMILES: O=C(O)[C@H]1C[C@@H]1C(=O)c1cc(Cl)c2nccnc2c1] | (1S,2S)-2-(8-chloroquinoxaline-6-carbonyl)cyclopropanecarboxylic acid |
| 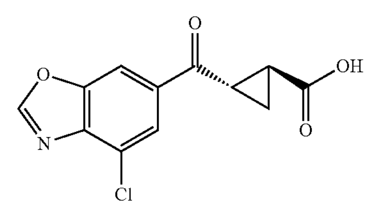 [SMILES: O=C(O)[C@H]1C[C@@H]1C(=O)c1cc(Cl)c2ncoc2c1] | (1S,2S)-2-(4-chlorobenzo[d]oxazole-6-carbonyl)cyclopropanecarboxylic acid |
| 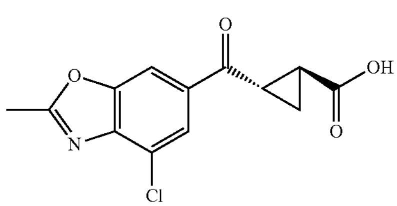 [SMILES: Cc1nc2c(Cl)cc(C(=O)[C@H]3C[C@@H]3C(=O)O)cc2o1] | (1S,2S)-2-(4-chloro-2-methylbenzo[d]oxazole-6-carbonyl)cyclopropanecarboxylic acid |
| 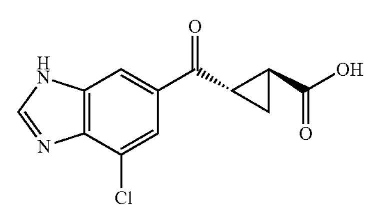 [SMILES: O=C(O)[C@H]1C[C@@H]1C(=O)c1cc(Cl)c2nc[nH]c2c1] | (1S,2S)-2-(4-chloro-1H-benzo[d]imidazole-6-carbonyl)cyclopropanecarboxylic acid |

| Structure | IUPAC Name |
|---|---|
| 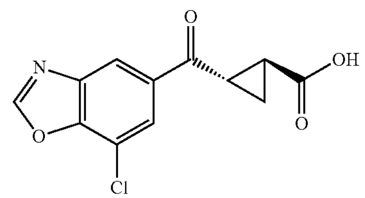 [SMILES: O=C(O)[C@H]1C[C@@H]1C(=O)c1cc(Cl)c2ocnc2c1] | (1S,2S)-2-(7-chlorobenzo[d]oxazole-5-carbonyl)cyclopropanecarboxylic acid |
| 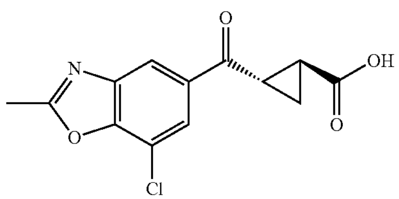 [SMILES: Cc1nc2cc(C(=O)[C@H]3C[C@@H]3C(=O)O)cc(Cl)c2o1] | (1S,2S)-2-(7-chloro-2-methylbenzo[d]oxazole-5-carbonyl)cyclopropanecarboxylic acid |
| 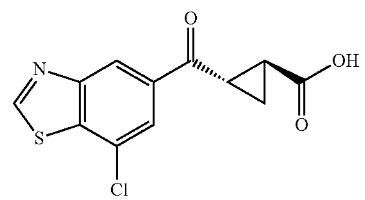 [SMILES: O=C(O)[C@H]1C[C@@H]1C(=O)c1cc(Cl)c2scnc2c1] | (1S,2S)-2-(7-chlorobenzo[d]thiazole-5-carbonyl)cyclopropanecarboxylic acid |
| 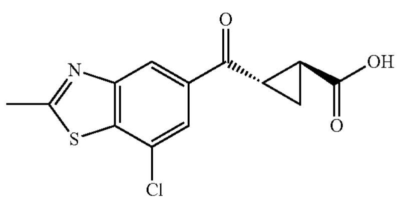 [SMILES: Cc1nc2cc(C(=O)[C@H]3C[C@@H]3C(=O)O)cc(Cl)c2s1] | (1S,2S)-2-(7-chloro-2-methylbenzo[d]thiazole-5-carbonyl)cyclopropanecarboxylic acid |
| 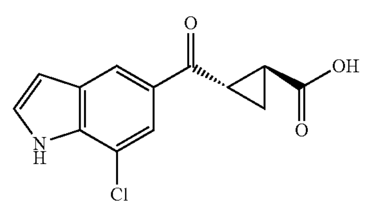 [SMILES: O=C(O)[C@H]1C[C@@H]1C(=O)c1cc(Cl)c2[nH]ccc2c1] | (1S,2S)-2-(7-chloro-1H-indole-5-carbonyl)cyclopropanecarboxylic acid |
| 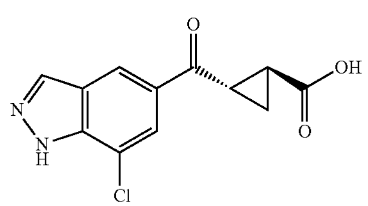 [SMILES: O=C(O)[C@H]1C[C@@H]1C(=O)c1cc(Cl)c2[nH]ncc2c1] | (1S,2S)-2-(7-chloro-1H-indazole-5-carbonyl)cyclopropanecarboxylic acid |
| 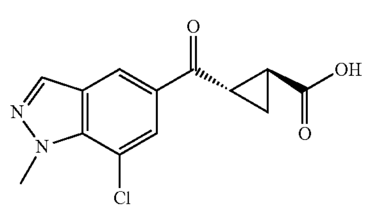 [SMILES: Cn1ncc2cc(C(=O)[C@H]3C[C@@H]3C(=O)O)cc(Cl)c21] | (1S,2S)-2-(7-chloro-1-methyl-1H-indazole-5-carbonyl)cyclopropanecarboxylic acid |

| Structure | IUPAC Name |
|---|---|
| 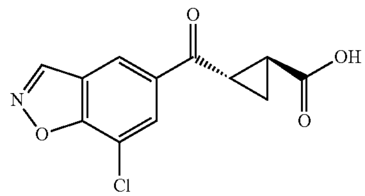 [SMILES: O=C(O)[C@H]1C[C@@H]1C(=O)c1cc(Cl)c2oncc2c1] | (1S,2S)-2-(7-chlorobenzo[d]isoxazole-5-carbonyl)cyclopropanecarboxylic acid |
| 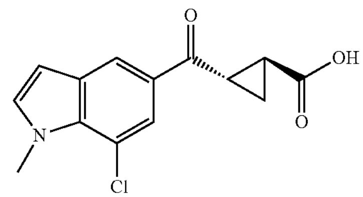 [SMILES: Cn1ccc2cc(C(=O)[C@H]3C[C@@H]3C(=O)O)cc(Cl)c21] | (1S,2S)-2-(7-chloro-1-methyl-1H-indole-5-carbonyl)cyclopropanecarboxylic acid |
| 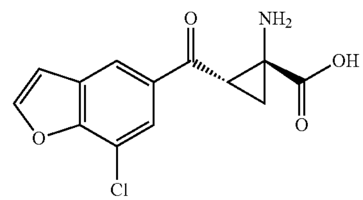 [SMILES: N[C@]1(C(=O)O)C[C@@H]1C(=O)c1cc(Cl)c2occc2c1] | (1R,2S)-1-amino-2-(7-chlorobenzofuran-5-carbonyl)cyclopropanecarboxylic acid |
| 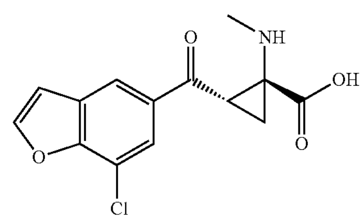 [SMILES: CN[C@]1(C(=O)O)C[C@@H]1C(=O)c1cc(Cl)c2occc2c1] | (1R,2S)-2-(7-chlorobenzofuran-5-carbonyl)-1-(methylamino)cyclopropanecarboxylic acid |
| 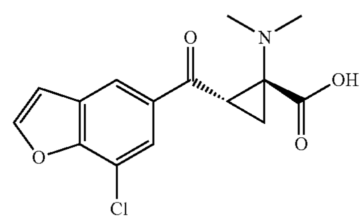 [SMILES: CN(C)[C@]1(C(=O)O)C[C@@H]1C(=O)c1cc(Cl)c2occc2c1] | (1R,2S)-2-(7-chlorobenzofuran-5-carbonyl)-1-(dimethylamino)cyclopropanecarboxylic acid |
| 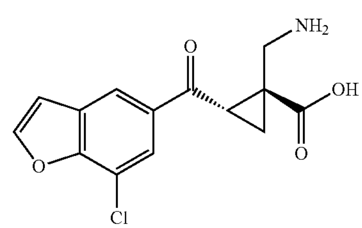 [SMILES: NC[C@]1(C(=O)O)C[C@@H]1C(=O)c1cc(Cl)c2occc2c1] | (1S,2S)-1-(aminomethyl)-2-(7-chlorobenzofuran-5-carbonyl)cyclopropanecarboxylic acid |
| 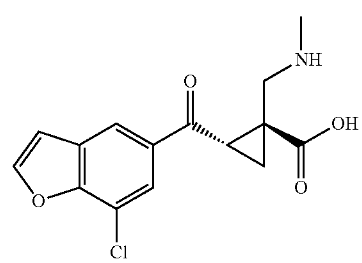 [SMILES: CNC[C@]1(C(=O)O)C[C@@H]1C(=O)c1cc(Cl)c2occc2c1] | (1S,2S)-2-(7-chlorobenzofuran-5-carbonyl)-1-((methylamino)methyl)cyclopropanecarboxylic acid |

| Structure | IUPAC Name |
|---|---|
| 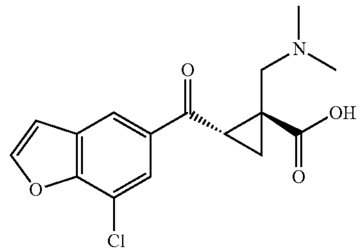 [SMILES: CN(C)C[C@]1(C(=O)O)C[C@@H]1C(=O)c1cc(Cl)c2occc2c1] | (1S,2S)-2-(7-chlorobenzofuran-5-carbonyl)-1-((dimethylamino)methyl)cyclopropanecarboxylic acid |
| 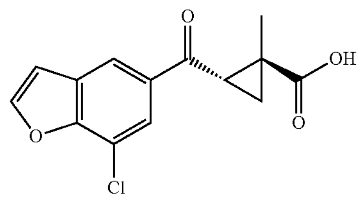 [SMILES: C[C@]1(C(=O)O)C[C@@H]1C(=O)c1cc(Cl)c2occc2c1] | (1S,2S)-2-(7-chlorobenzofuran-5-carbonyl)-1-methylcyclopropanecarboxylic acid |
| 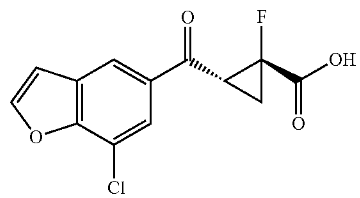 [SMILES: O=C(c1cc(Cl)c2occc2c1)[C@H]1C[C@]1(F)C(=O)O] | (1R,2R)-2-(7-chlorobenzofuran-5-carbonyl)-1-fluorocyclopropanecarboxylic acid |
| 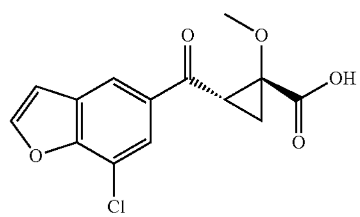 [SMILES: CO[C@]1(C(=O)O)C[C@@H]1C(=O)c1cc(Cl)c2occc2c1] | (1R,2S)-2-(7-chlorobenzofuran-5-carbonyl)-1-methoxycyclopropanecarboxylic acid |
| 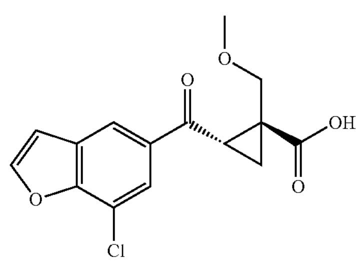 [SMILES: COC[C@]1(C(=O)O)C[C@@H]1C(=O)c1cc(Cl)c2occc2c1] | (1S,2S)-2-(7-chlorobenzofuran-5-carbonyl)-1-(methoxymethyl)cyclopropanecarboxylic acid |
| 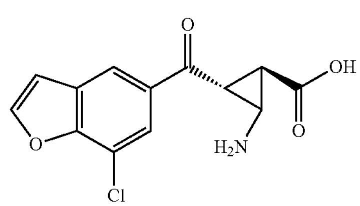 [SMILES: NC1[C@H](C(=O)O)[C@H]1C(=O)c1cc(Cl)c2occc2c1] | (1R,3R)-2-amino-3-(7-chlorobenzofuran-5-carbonyl)cyclopropanecarboxylic acid |
| 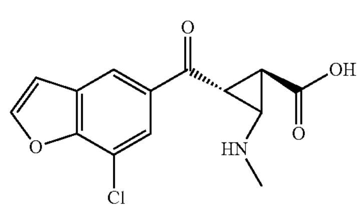 [SMILES: CNC1[C@H](C(=O)O)[C@H]1C(=O)c1cc(Cl)c2occc2c1] | (1R,2R)-2-(7-chlorobenzofuran-5-carbonyl)-3-(methylamino)cyclopropanecarboxylic acid |

-continued

| Structure | IUPAC Name |
|---|---|
| 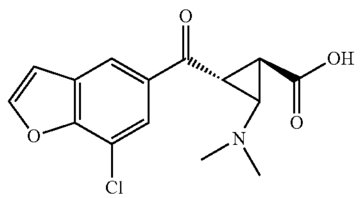 [SMILES: CN(C)C1[C@H](C(=O)O)[C@H]1C(=O)c1cc(Cl)c2occc2c1] | (1R,2R)-2-(7-chlorobenzofuran-5-carbonyl)-3-(dimethylamino)cyclopropanecarboxylic acid |
| 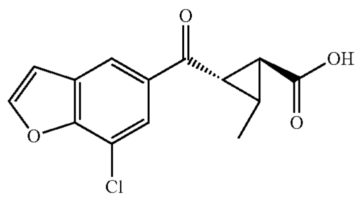 [SMILES: CC1[C@H](C(=O)O)[C@H]1C(=O)c1cc(Cl)c2occc2c1] | (1S,2S)-2-(7-chlorobenzofuran-5-carbonyl)-3-methylcyclopropanecarboxylic acid |
| 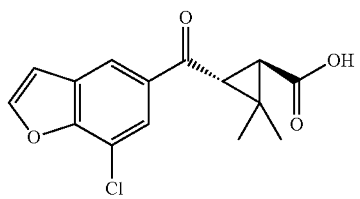 [SMILES: CC1(C)[C@H](C(=O)O)[C@H]1C(=O)c1cc(Cl)c2occc2c1] | (1R,3R)-3-(7-chlorobenzofuran-5-carbonyl)-2,2-dimethylcyclopropanecarboxylic acid |
| 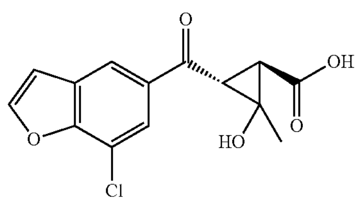 [SMILES: CC1(O)[C@H](C(=O)O)[C@H]1C(=O)c1cc(Cl)c2occc2c1] | (1R,3R)-3-(7-chlorobenzofuran-5-carbonyl)-2-hydroxy-2-methylcyclopropanecarboxylic acid |
| 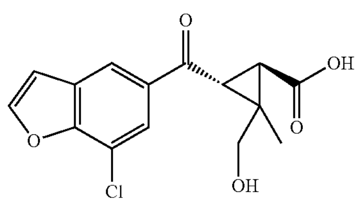 [SMILES: CC1(CO)[C@H](C(=O)O)[C@H]1C(=O)c1cc(Cl)c2occc2c1] | (1R,3R)-3-(7-chlorobenzofuran-5-carbonyl)-2-(hydroxymethyl)-2-methylcyclopropanecarboxylic acid |
| 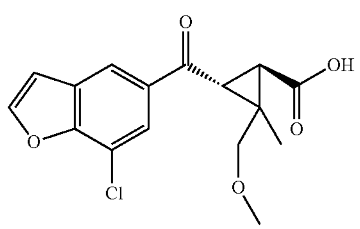 [SMILES: COCC1(C)[C@H](C(=O)O)[C@H]1C(=O)c1cc(Cl)c2occc2c1] | (1R,3R)-3-(7-chlorobenzofuran-5-carbonyl)-2-(methoxymethyl)-2-methylcyclopropanecarboxylic acid |
| 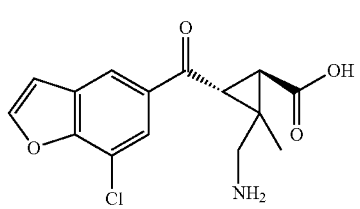 [SMILES: CC1(CN)[C@H](C(=O)O)[C@H]1C(=O)c1cc(Cl)c2occc2c1] | (1R,3R)-2-(aminomethyl)-3-(7-chlorobenzofuran-5-carbonyl)-2-methylcyclopropanecarboxylic acid |

| Structure | IUPAC Name |
|---|---|
| 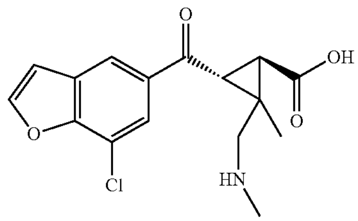 [SMILES: CNCC1(C)[C@H](C(=O)O)[C@H]1C(=O)c1cc(Cl)c2occc2c1] | (1R,3R)-3-(7-chlorobenzofuran-5-carbonyl)-2-methyl-2-((methylamino)methyl)cyclopropanecarboxylic acid |
| 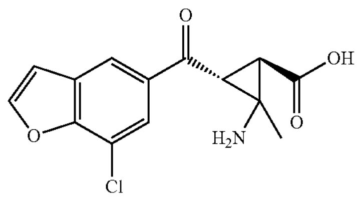 [SMILES: CC1(N)[C@H](C(=O)O)[C@H]1C(=O)c1cc(Cl)c2occc2c1] | (1R,3R)-2-amino-3-(7-chlorobenzofuran-5-carbonyl)-2-methylcyclopropanecarboxylic acid |
| 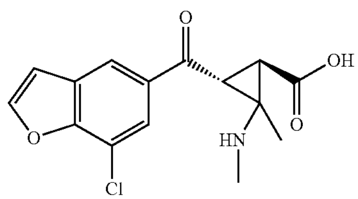 [SMILES: CNC1(C)[C@H](C(=O)O)[C@H]1C(=O)c1cc(Cl)c2occc2c1] | (1R,3R)-3-(7-chlorobenzofuran-5-carbonyl)-2-methyl-2-(methylamino)cyclopropanecarboxylic acid |
| 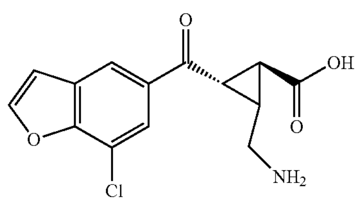 [SMILES: NCC1[C@H](C(=O)O)[C@H]1C(=O)c1cc(Cl)c2occc2c1] | (1S,3S)-2-(aminomethyl)-3-(7-chlorobenzofuran-5-carbonyl)cyclopropanecarboxylic acid |
| 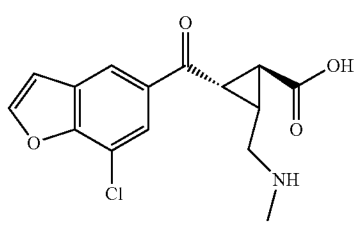 [SMILES: CNCC1[C@H](C(=O)O)[C@H]1C(=O)c1cc(Cl)c2occc2c1] | (1S,2S)-2-(7-chlorobenzofuran-5-carbonyl)-3-((methylamino)methyl)cyclopropanecarboxylic acid |
| 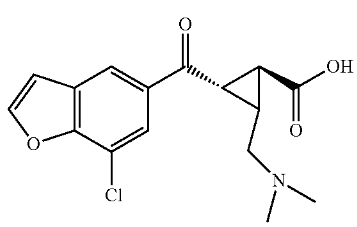 [SMILES: CN(C)CC1[C@H](C(=O)O)[C@H]1C(=O)c1cc(Cl)c2occc2c1] | (1S,2S)-2-(7-chlorobenzofuran-5-carbonyl)-3-((dimethylamino)methyl)cyclopropanecarboxylic acid |

| Structure | IUPAC Name |
|---|---|
| 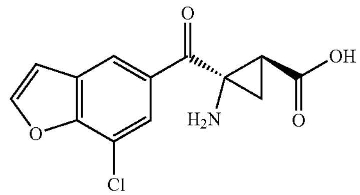 [SMILES: N[C@]1(C(=O)c2cc(Cl)c3occc3c2)C[C@@H]1C(=O)O] | (1S,2R)-2-amino-2-(7-chlorobenzofuran-5-carbonyl)cyclopropanecarboxylic acid |
| 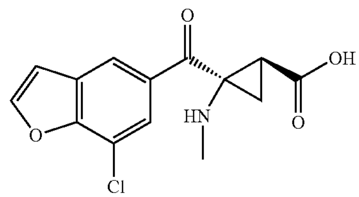 [SMILES: CN[C@]1(C(=O)c2cc(Cl)c3occc3c2)C[C@@H]1C(=O)O] | (1S,2R)-2-(7-chlorobenzofuran-5-carbonyl)-2-(methylamino)cyclopropanecarboxylic acid |
| 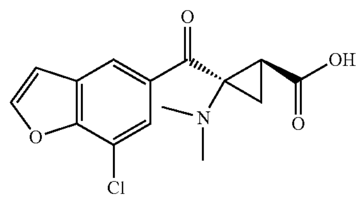 [SMILES: CN(C)[C@]1(C(=O)c2cc(Cl)c3occc3c2)C[C@@H]1C(=O)O] | (1S,2R)-2-(7-chlorobenzofuran-5-carbonyl)-2-(dimethylamino)cyclopropanecarboxylic acid |
| 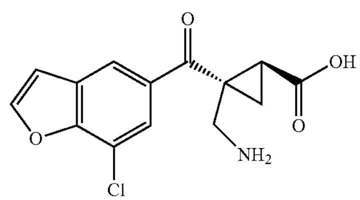 [SMILES: NC[C@]1(C(=O)c2cc(Cl)c3occc3c2)C[C@@H]1C(=O)O] | (1S,2S)-2-(aminomethyl)-2-(7-chlorobenzofuran-5-carbonyl)cyclopropanecarboxylic acid |
| 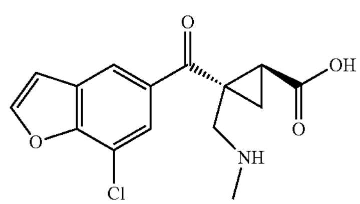 [SMILES: CNC[C@]1(C(=O)c2cc(Cl)c3occc3c2)C[C@@H]1C(=O)O] | (1S,2S)-2-(7-chlorobenzofuran-5-carbonyl)-2-((methylamino)methyl)cyclopropanecarboxylic acid |
| 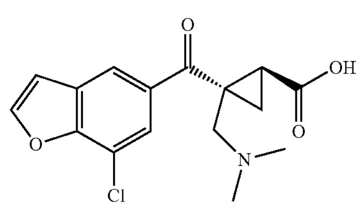 [SMILES: CN(C)C[C@]1(C(=O)c2cc(Cl)c3occc3c2)C[C@@H]1C(=O)O] | (1S,2S)-2-(7-chlorobenzofuran-5-carbonyl)-2-((dimethylamino)methyl)cyclopropanecarboxylic acid |
| 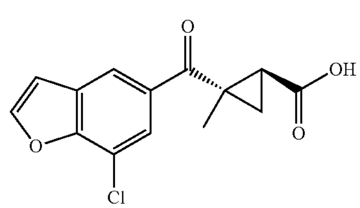 [SMILES: C[C@]1(C(=O)c2cc(Cl)c3occc3c2)C[C@@H]1C(=O)O] | (1S,2S)-2-(7-chlorobenzofuran-5-carbonyl)-2-methylcyclopropanecarboxylic acid |

The following are examples of compounds of Formula I which may be considered prodrugs, which may be prepared using the methods described above and known in the art and are expected to have activity against KMO and in the treatment of KMO-mediated diseases such as those disclosed herein.

| Structure | Mol. Weight | IUPAC Name |
|---|---|---|
| 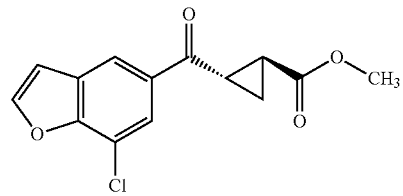 [SMILES: COC(=O)[C@H]1C[C@@H]1C(=O)c1cc(Cl)c2occc2c1] | 278.688 | methyl (1S,2S)-2-(7-chloro-1-benzofuran-5-carbonyl)cyclopropane-1-carboxylate |
| | 426.802 | [(3R,4S,5R,6S)-3,4,5,6-tetrahydroxyoxan-2-yl]methyl (1S,2S)-2-(7-chloro-1-benzofuran-5-carbonyl)cyclopropane-1-carboxylate |
| | 426.802 | [(3S,4S,5R)-3,4,5,6-tetrahydroxyoxan-2-yl]methyl (1S,2S)-2-(7-chloro-1-benzofuran-5-carbonyl)cyclopropane-1-carboxylate |
| 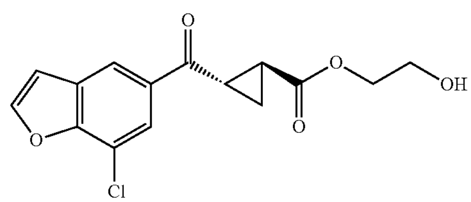 [SMILES: O=C(OCCO)[C@H]1C[C@@H]1C(=O)c1cc(Cl)c2occc2c1] | 308.714 | 2-hydroxyethyl (1S,2S)-2-(7-chloro-1-benzofuran-5-carbonyl)cyclopropane-1-carboxylate |
| 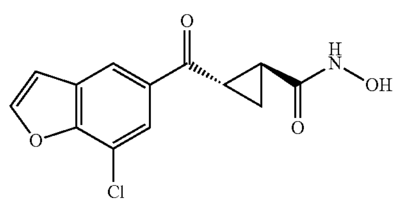 [SMILES: O=C(NO)[C@H]1C[C@@H]1C(=O)c1cc(Cl)c2occc2c1] | 279.676 | (1S,2S)-2-(7-chloro-1-benzofuran-5-carbonyl)-N-hydroxycyclopropane-1-carboxamide |
| 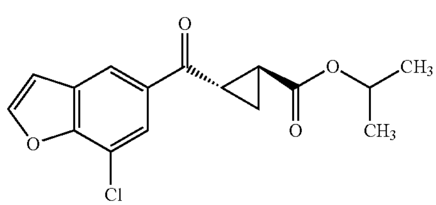 [SMILES: CC(C)OC(=O)[C@H]1C[C@@H]1C(=O)c1cc(Cl)c2occc2c1] | 306.741 | propan-2-yl (1S,2S)-2-(7-chloro-1-benzofuran-5-carbonyl)cyclopropane-1-carboxylate |
| 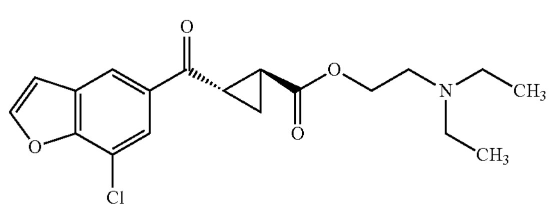 [SMILES: CCN(CC)CCOC(=O)[C@H]1C[C@@H]1C(=O)c1cc(Cl)c2occc2c1] | 363.835 | 2-(diethylamino)ethyl (1S,2S)-2-(7-chloro-1-benzofuran-5-carbonyl)cyclopropane-1-carboxylate |

-continued

| Structure | Mol. Weight | IUPAC Name |
|---|---|---|
| 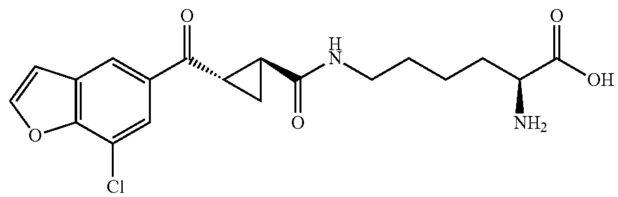 [SMILES: N[C@@H](CCCCNC(=O)[C@H]1C[C@@H]1C(=O)c1cc(Cl)c2occc2c1)C(=O)O] | 392.833 | (2S)-2-amino-6-{[(1S,2S)-2-(7-chloro-1-benzofuran-5-carbonyl)cyclopropyl]formamido}hexanoic acid |
| 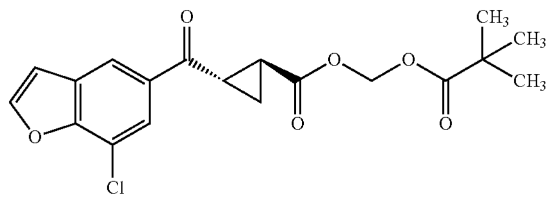 [SMILES: CC(C)(C)C(=O)OCOC(=O)[C@H]1C[C@@H]1C(=O)c1cc(Cl)c2occc2c1] | 378.804 | [(1S,2S)-2-(7-chloro-1-benzofuran-5-carbonyl)cyclopropanecarbonyloxy]methyl 2,2-dimethylpropanoate |
| 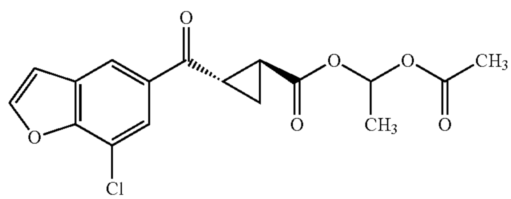 [SMILES: CC(=O)OC(C)OC(=O)[C@H]1C[C@@H]1C(=O)c1cc(Cl)c2occc2c1] | 350.75 | 1-[(1S,2S)-2-(7-chloro-1-benzofuran-5-carbonyl)cyclopropanecarbonyloxy]ethyl acetate |
| 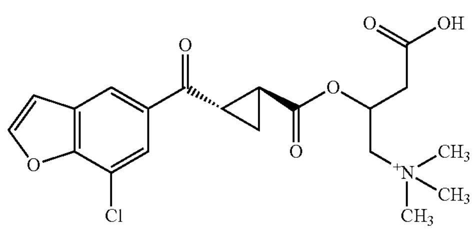 [SMILES: C[N+](C)(C)CC(CC(=O)O)OC(=O)[C@H]1C[C@@H]1C(=O)c1cc(Cl)c2occc2c1] | 408.853 | {3-carboxy-2-[(1S,2S)-2-(7-chloro-1-benzofuran-5-carbonyl)cyclopropanecarbonyloxy]propyl} trimethylazanium |
| 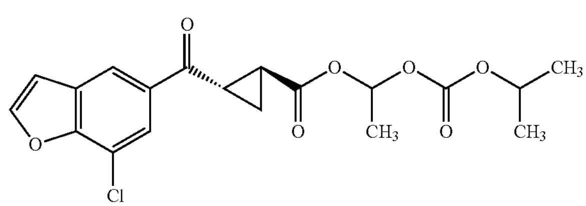 [SMILES: CC(C)OC(=O)OC(C)OC(=O)[C@H]1C[C@@H]1C(=O)c1cc(Cl)c2occc2c1] | 394.803 | 1-{[(propan-2-yloxy)carbonyl]oxy}ethyl (1S,2S)-2-(7-chloro-1-benzofuran-5-carbonyl)cyclopropane-1-carboxylate |
| 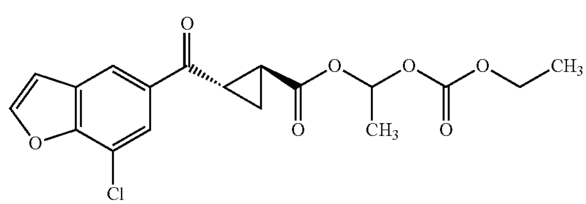 [SMILES: CCOC(=O)OC(C)OC(=O)[C@H]1C[C@@H]1C(=O)c1cc(Cl)c2occc2c1] | 380.776 | 1-[(ethoxycarbonyl)oxy]ethyl (1S,2S)-2-(7-chloro-1-benzofuran-5-carbonyl)cyclopropane-1-carboxylate |
| 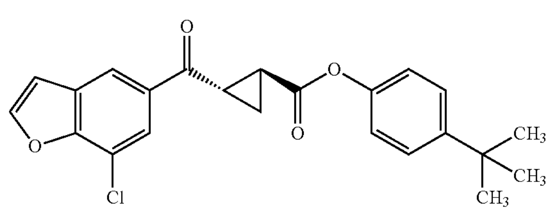 [SMILES: CC(C)(C)c1ccc(OC(=O)[C@H]2C[C@@H]2C(=O)c2cc(Cl)c3occc3c2)cc1] | 396.863 | 4-tert-butylphenyl (1S,2S)-2-(7-chloro-1-benzofuran-5-carbonyl)cyclopropane-1-carboxylate |

| Structure | Mol. Weight | IUPAC Name |
|---|---|---|
| | 320.767 | 2-methylpropyl (1S,2S)-2-(7-chloro-1-benzofuran-5-carbonyl)cyclopropane-1-carboxylate |
| | 320.767 | butyl (1S,2S)-2-(7-chloro-1-benzofuran-5-carbonyl)cyclopropane-1-carboxylate |
| 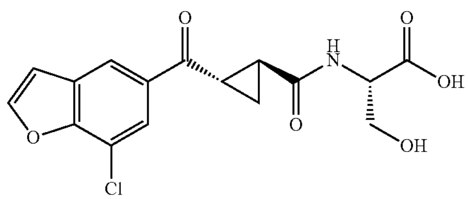 [SMILES: O=C(O)[C@H](CO)NC(=O)[C@H]1C[C@@H]1C(=O)c1cc(Cl)c2occc2c1] | 351.738 | (2S)-2-{[(1S,2S)-2-(7-chloro-1-benzofuran-5-carbonyl)cyclopropyl]formamido}-3-hydroxypropanoic acid |
| 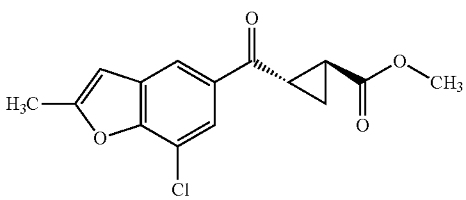 | 292.714 | methyl (1S,2S)-2-(7-chloro-2-methyl-1-benzofuran-5-carbonyl)cyclopropane-1-carboxylate |
| | 440.828 | [(3R,4S,5R,6S)-3,4,5,6-tetrahydroxyoxan-2-yl]methyl (1S,2S)-2-(7-chloro-2-methyl-1-benzofuran-5-carbonyl)cyclopropane-1-carboxylate |
| | 440.828 | [(3S,4S,5R)-3,4,5,6-tetrahydroxyoxan-2-yl]methyl (1S,2S)-2-(7-chloro-2-methyl-1-benzofuran-5-carbonyl)cyclopropane-1-carboxylate |
| 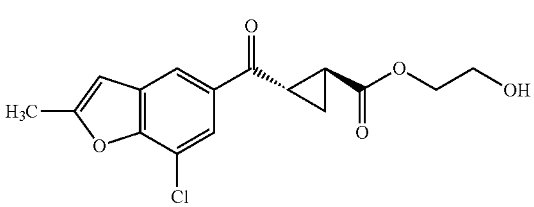 [SMILES: Cc1cc2cc(C(=O)[C@H]3C[C@@H]3C(=O)OCCO)cc(Cl)c2o1] | 322.74 | 2-hydroxyethyl (1S,2S)-2-(7-chloro-2-methyl-1-benzofuran-5-carbonyl)cyclopropane-1-carboxylate |

-continued

| Structure | Mol. Weight | IUPAC Name |
|---|---|---|
| 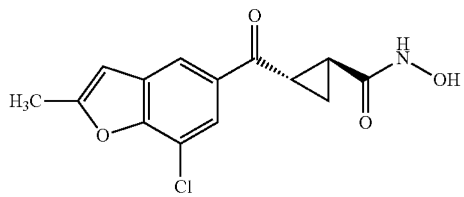 [SMILES: Cc1cc2cc(C(=O)[C@H]3C[C@@H]3C(=O)NO)cc(Cl)c2o1] | 293.702 | (1S,2S)-2-(7-chloro-2-methyl-1-benzofuran-5-carbonyl)-N-hydroxycyclopropane-1-carboxamide |
| 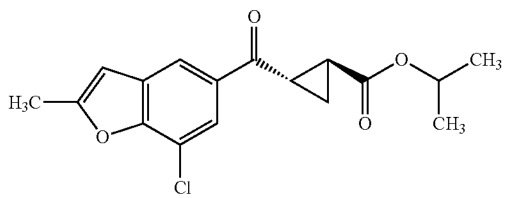 [SMILES: Cc1cc2cc(C(=O)[C@H]3C[C@@H]3C(=O)OC(C)C)cc(Cl)c2o1] | 320.767 | propan-2-yl (1S,2S)-2-(7-chloro-2-methyl-1-benzofuran-5-carbonyl)cyclopropane-1-carboxylate |
| 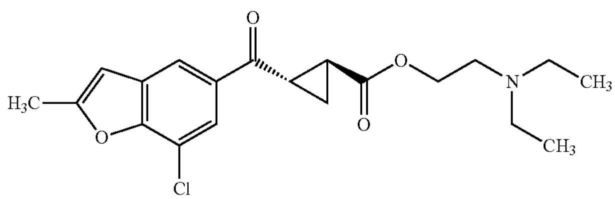 [SMILES: CCN(CC)CCOC(=O)[C@H]1C[C@@H]1C(=O)c1cc(Cl)c2oc(C)cc2c1] | 377.862 | 2-(diethylamino)ethyl (1S,2S)-2-(7-chloro-2-methyl-1-benzofuran-5-carbonyl)cyclopropane-1-carboxylate |
| 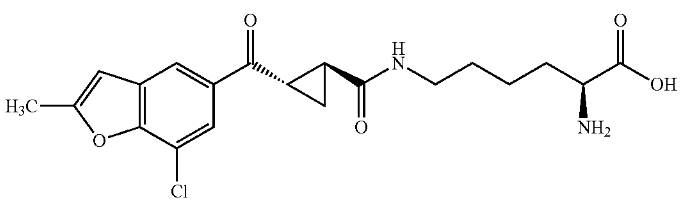 [SMILES: Cc1cc2cc(C(=O)[C@H]3C[C@@H]3C(=O)NCCCC[C@H](N)C(=O)O)cc(Cl)c2o1] | 406.86 | (2S)-2-amino-6-{[(1S,2S)-2-(7-chloro-2-methyl-1-benzofuran-5-carbonyl)cyclopropyl]formamido}hexanoic acid |
| 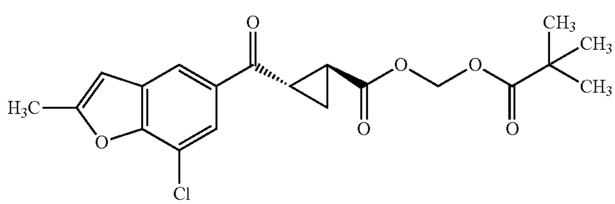 [SMILES: Cc1cc2cc(C(=O)[C@H]3C[C@@H]3C(=O)OCOC(=O)C(C)(C)C)cc(Cl)c2o1] | 392.83 | [(1S,2S)-2-(7-chloro-2-methyl-1-benzofuran-5-carbonyl)cyclopropanecarbonyloxy]methyl 2,2-dimethylpropanoate |
| 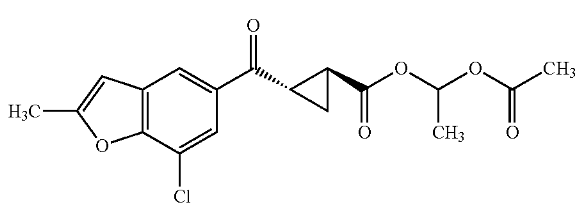 [SMILES: CC(=O)OC(C)OC(=O)[C@H]1C[C@@H]1C(=O)c1cc(Cl)c2oc(C)cc2c1] | 364.777 | 1-[(1S,2S)-2-(7-chloro-2-methyl-1-benzofuran-5-carbonyl)cyclopropanecarbonyloxy]ethyl acetate |
| 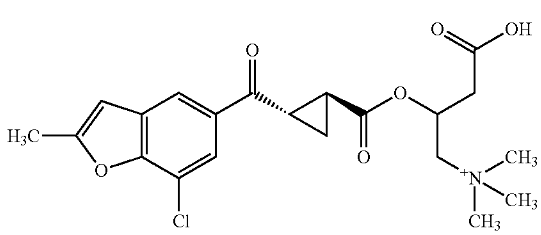 | 422.879 | {3-carboxy-2-[(1S,2S)-2-(7-chloro-2-methyl-1-benzofuran-5-carbonyl)cyclopropanecarbonyloxy]propyl}trimethylazanium |

-continued

| Structure | Mol. Weight | IUPAC Name |
|---|---|---|
| 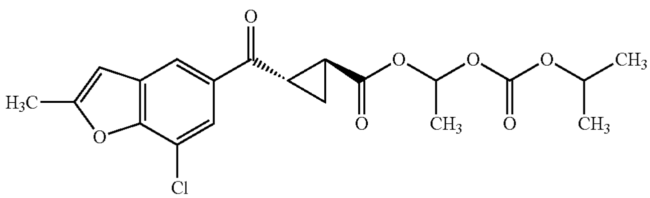 [SMILES: Cc1cc2cc(C(=O)[C@H]3C[C@@H]3C(=O)OC(C)OC(=O)OC(C)C)cc(Cl)c2o1] | 408.83 | 1-{[(propan-2-yloxy)carbonyl]oxy}ethyl (1S,2S)-2-(7-chloro-2-methyl-1-benzofuran-5-carbonyl)cyclopropane-1-carboxylate |
| 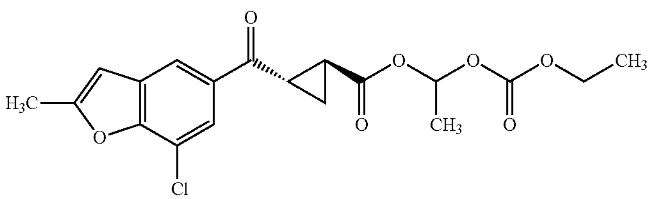 [SMILES: CCOC(=O)OC(C)OC(=O)[C@H]1C[C@@H]1C(=O)c1cc(Cl)c2oc(C)cc2c1] | 394.803 | 1-[(ethoxycarbonyl)oxy]ethyl (1S,2S)-2-(7-chloro-2-methyl-1-benzofuran-5-carbonyl)cyclopropane-1-carboxylate |
| 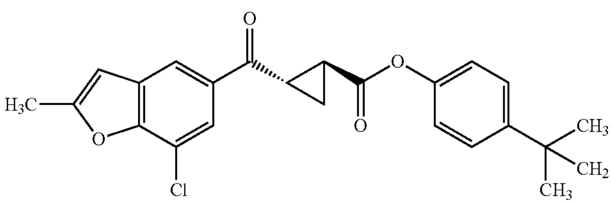 [SMILES: Cc1cc2cc(C(=O)[C@H]3C[C@@H]3C(=O)Oc3ccc(C(C)(C)C)cc3)cc(Cl)c2o1] | 410.89 | 4-tert-butylphenyl (1S,2S)-2-(7-chloro-2-methyl-1-benzofuran-5-carbonyl)cyclopropane-1-carboxylate |
| | 334.794 | 2-methylpropyl (1S,2S)-2-(7-chloro-2-methyl-1-benzofuran-5-carbonyl)cyclopropane-1-carboxylate |
| | 334.794 | butyl (1S,2S)-2-(7-chloro-2-methyl-1-benzofuran-5-carbonyl)cyclopropane-1-carboxylate |
| 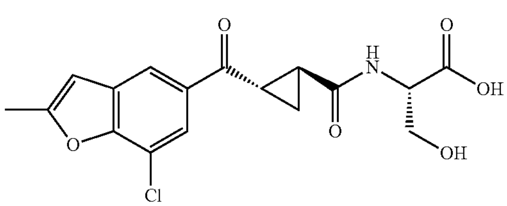 [SMILES: Cc1cc2cc(C(=O)[C@H]3C[C@@H]3C(=O)N[C@@H](CO)C(=O)O)cc(Cl)c2o1] | 365.765 | (2S)-2-{[(1S,2S)-2-(7-chloro-2-methyl-1-benzofuran-5-carbonyl)cyclopropyl]formamido}-3-hydroxypropanoic acid |
| 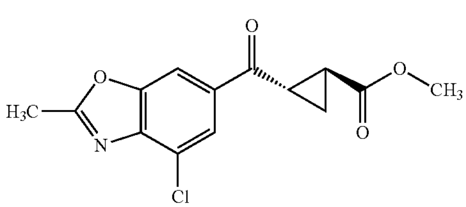 | 293.702 | methyl(1S,2S)-2-(4-chloro-2-methyl-1,3-benzoxazole-6-carbonyl)cyclopropane-1-carboxylate |

-continued

| Structure | Mol. Weight | IUPAC Name |
|---|---|---|
| | 441.816 | [(3R,4S,5R,6S)-3,4,5,6-tetrahydroxyoxan-2-yl]methyl(1S,2S)-2-(4-chloro-2-methyl-1,3-benzoxazole-6-carbonyl)cyclopropane-1-carboxylate |
| | 441.816 | [(3S,4S,5R)-3,4,5,6-tetrahydroxyoxan-2-yl]methyl(1S,2S)-2-(4-chloro-2-methyl-1,3-benzoxazole-6-carbonyl)cyclopropane-1-carboxylate |
| 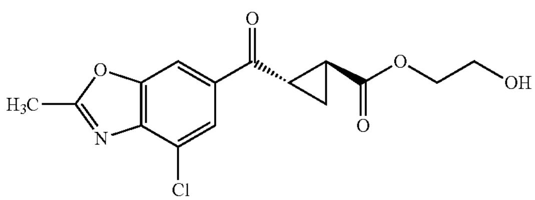 [SMILES: Cc1nc2c(Cl)cc(C(=O)[C@H]3C[C@@H]3C(=O)OCCO)cc2o1] | 323.728 | 2-hydroxyethyl (1S,2S)-2-(4-chloro-2-methyl-1,3-benzoxazole-6-carbonyl)cyclopropane-1-carboxylate |
| 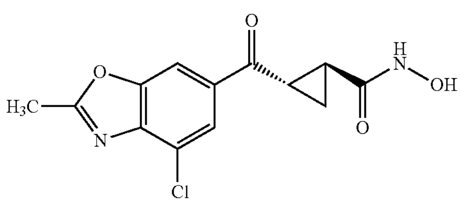 [SMILES: Cc1nc2c(Cl)cc(C(=O)[C@H]3C[C@@H]3C(=O)NO)cc2o1] | 294.69 | (1S,2S)-2-(4-chloro-2-methyl-1,3-benzoxazole-6-carbonyl)-N-hydroxycyclopropane-1-carboxamide |
| 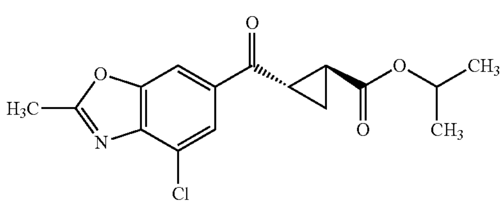 [SMILES: Cc1nc2c(Cl)cc(C(=O)[C@H]3C[C@@H]3C(=O)OC(C)C)cc2o1] | 321.756 | propan-2-yl (1S,2S)-2-(4-chloro-2-methyl-1,3-benzoxazole-6-carbonyl)cyclopropane-1-carboxylate |
| 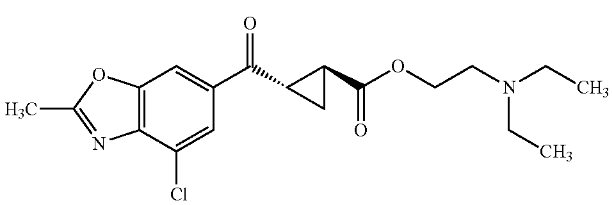 [SMILES: CCN(CC)CCOC(=O)[C@H]1C[C@@H]1C(=O)c1cc(Cl)c2nc(C)oc2c1] | 378.85 | 2-(diethylamino)ethyl (1S,2S)-2-(4-chloro-2-methyl-1,3-benzoxazole-6-carbonyl)cyclopropane-1-carboxylate |
| 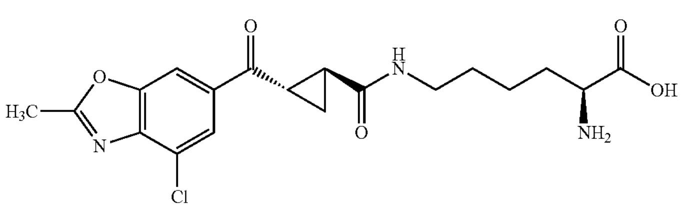 [SMILES: Cc1nc2c(Cl)cc(C(=O)[C@H]3C[C@@H]3C(=O)NCCCC[C@H](N)C(=O)O)cc2o1] | 407.848 | (2S)-2-amino-6-{[(1S,2S)-2-(4-chloro-2-methyl-1,3-benzoxazole-6-carbonyl)cyclopropyl]formamido}hexanoic acid |

-continued

| Structure | Mol. Weight | IUPAC Name |
|---|---|---|
| 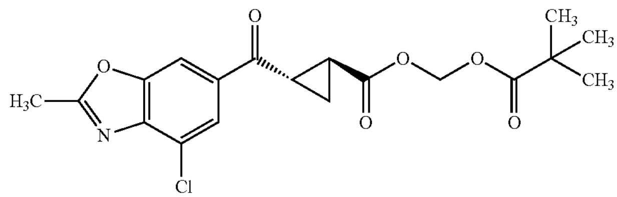 [SMILES: Cc1nc2c(Cl)cc(C(=O)[C@H]3C[C@@H]3C(=O)OCOC(=O)C(C)(C)C)cc2o1] | 393.818 | [(1S,2S)-2-(4-chloro-2-methyl-1,3-benzoxazole-6-carbonyl)cyclopropanecarbonyloxy]methyl 2,2-dimethylpropanoate |
| 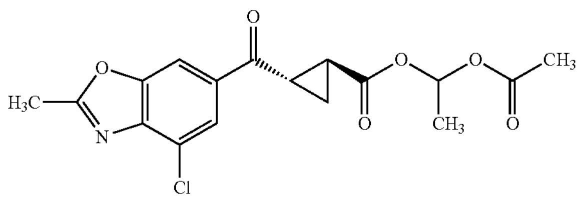 [SMILES: CC(=O)OC(C)OC(=O)[C@H]1C[C@@H]1C(=O)c1cc(Cl)c2nc(C)oc2c1] | 365.765 | 1-[(1S,2S)-2-(4-chloro-2-methyl-1,3-benzoxazole-6-carbonyl)cyclopropanecarbonyloxy]ethyl acetate |
| 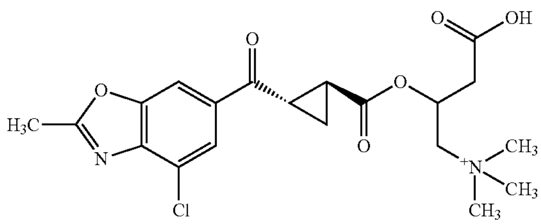 | 423.867 | {3-carboxy-2-[(1S,2S)-2-(4-chloro-2-methyl-1,3-benzoxazole-6-carbonyl)cyclopropanecarbonyloxy]propyl} trimethylazanium |
| 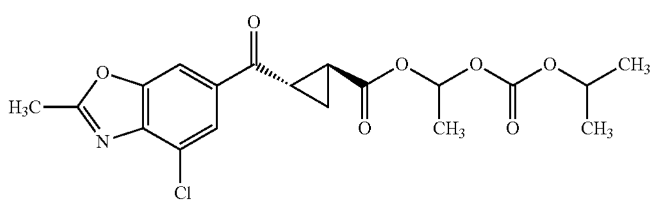 [SMILES: Cc1nc2c(Cl)cc(C(=O)[C@H]3C[C@@H]3C(=O)OC(C)OC(=O)OC(C)C)cc2o1] | 409.818 | 1-{[(propan-2-yloxy)carbonyl]oxy}ethyl (1S,2S)-2-(4-chloro-2-methyl-1,3-benzoxazole-6-carbonyl)cyclopropane-1-carboxylate |
| 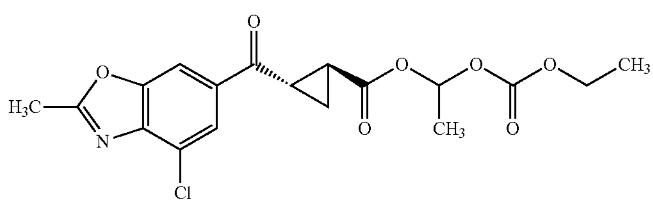 [SMILES: CCOC(=O)OC(C)OC(=O)[C@H]1C[C@@H]1C(=O)c1cc(Cl)c2nc(C)oc2c1] | 395.791 | 1-[(ethoxycarbonyl)oxy]ethyl (1S,2S)-2-(4-chloro-2-methyl-1,3-benzoxazole-6-carbonyl)cyclopropane-1-carboxylate |
| 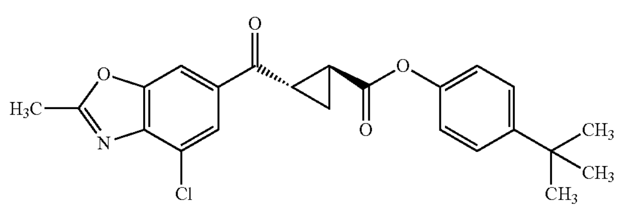 [SMILES: Cc1nc2c(Cl)cc(C(=O)[C@H]3C[C@@H]3C(=O)Oc3ccc(C(C)(C)C)cc3)cc2o1] | 411.878 | 4-tert-butylphenyl (1S,2S)-2-(4-chloro-2-methyl-1,3-benzoxazole-6-carbonyl)cyclopropane-1-carboxylate |
| 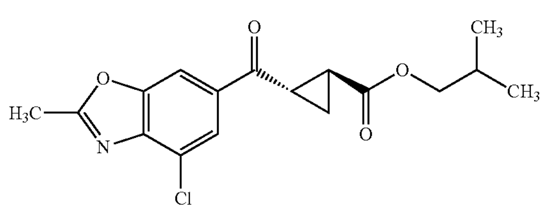 [SMILES: Cc1nc2c(Cl)cc(C(=O)[C@H]3C[C@@H]3C(=O)OCC(C)C)cc2o1] | 335.782 | 2-methylpropyl (1S,2S)-2-(4-chloro-2-methyl-1,3-benzoxazole-6-carbonyl)cyclopropane-1-carboxylate |

-continued

| Structure | Mol. Weight | IUPAC Name |
|---|---|---|
| 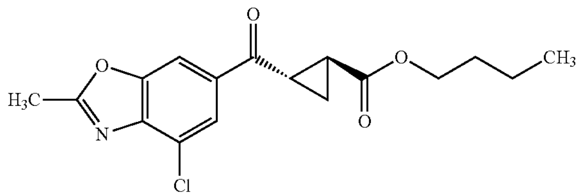 [SMILES: CCCCOC(=O)[C@H]1C[C@@H]1C(=O)c1cc(Cl)c2nc(C)oc2c1] | 335.782 | butyl (1S,2S)-2-(4-chloro-2-methyl-1,3-benzoxazole-6-carbonyl)cyclopropane-1-carboxylate |
| 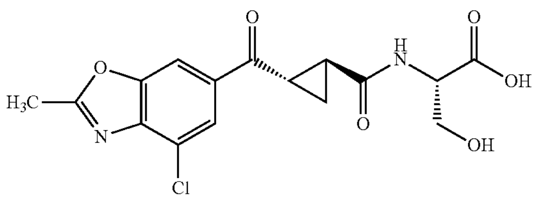 [SMILES: Cc1nc2c(Cl)cc(C(=O)[C@H]3C[C@@H]3C(=O)N[C@@H](CO)C(=O)O)cc2o1] | 366.753 | (2S)-2-{[(1S,2S)-2-(4-chloro-2-methyl-1,3-benzoxazole-6-carbonyl)cyclopropyl]formamido}-3-hydroxypropanoic acid |
| 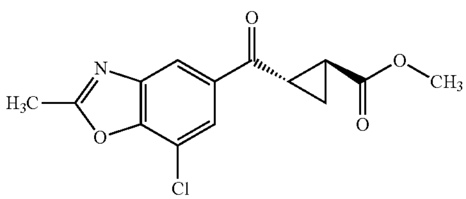 | 293.702 | methyl (1S,2S)-2-(7-chloro-2-methyl-1,3-benzoxazole-5-carbonyl)cyclopropane-1-carboxylate |
| | 441.816 | [(3R,4S,5R,6S)-3,4,5,6-tetrahydroxyoxan-2-yl]methyl (1S,2S)-2-(7-chloro-2-methyl-1,3-benzoxazole-5-carbonyl)cyclopropane-1-carboxylate |
| | 441.816 | [(3S,4S,5R)-3,4,5,6-tetrahydroxyoxan-2-yl]methyl (1S,2S)-2-(7-chloro-2-methyl-1,3-benzoxazole-5-carbonyl)cyclopropane-1-carboxylate |
| 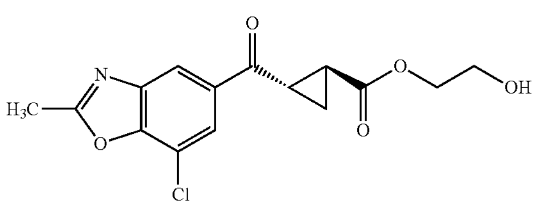 [SMILES: Cc1nc2cc(C(=O)[C@H]3C[C@@H]3C(=O)OCCO)cc(Cl)c2o1] | 323.728 | 2-hydroxyethyl (1S,2S)-2-(7-chloro-2-methyl-1,3-benzoxazole-5-carbonyl)cyclopropane-1-carboxylate |
| 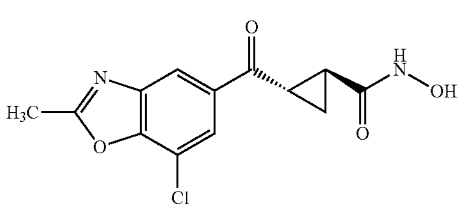 [SMILES: Cc1nc2cc(C(=O)[C@H]3C[C@@H]3C(=O)NO)cc(Cl)c2o1] | 294.69 | (1S,2S)-2-(7-chloro-2-methyl-1,3-benzoxazole-5-carbonyl)-N-hydroxycyclopropane-1-carboxamide |

-continued

| Structure | Mol. Weight | IUPAC Name |
|---|---|---|
| 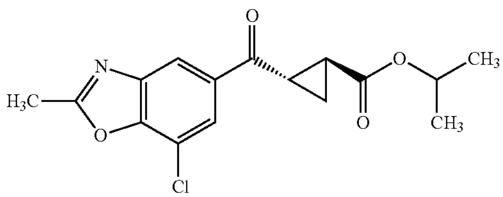 [SMILES: Cc1nc2cc(C(=O)[C@H]3C[C@@H]3C(=O)OC(C)C)cc(Cl)c2o1] | 321.756 | propan-2-yl (1S,2S)-2-(7-chloro-2-methyl-1,3-benzoxazole-5-carbonyl)cyclopropane-1-carboxylate |
| 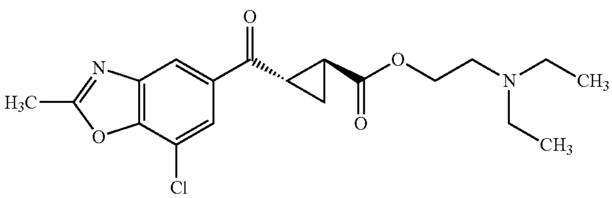 [SMILES: CCN(CC)CCOC(=O)[C@H]1C[C@@H]1C(=O)c1cc(Cl)c2oc(C)nc2c1] | 378.85 | 2-(diethylamino)ethyl (1S,2S)-2-(7-chloro-2-methyl-1,3-benzoxazole-5-carbonyl)cyclopropane-1-carboxylate |
| 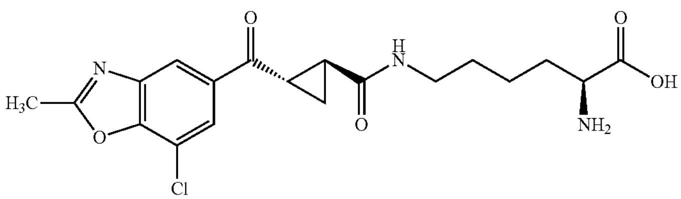 [SMILES: Cc1nc2cc(C(=O)[C@H]3C[C@@H]3C(=O)NCCCC[C@H](N)C(=O)O)cc(Cl)c2o1] | 407.848 | (2S)-2-amino-6-{[(1S,2S)-2-(7-chloro-2-methyl-1,3-benzoxazole-5-carbonyl)cyclopropyl]formamido}hexanoic acid |
| 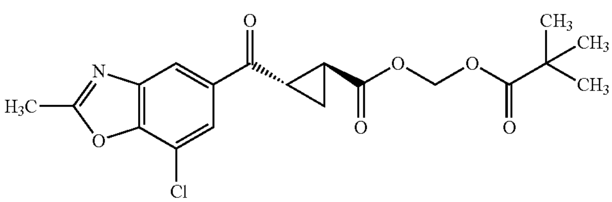 [SMILES: Cc1nc2cc(C(=O)[C@H]3C[C@@H]3C(=O)OCOC(=O)C(C)(C)C)cc(Cl)c2o1] | 393.818 | [(1S,2S)-2-(7-chloro-2-methyl-1,3-benzoxazole-5-carbonyl)cyclopropanecarbonyloxy]methyl 2,2-dimethylpropanoate |
| 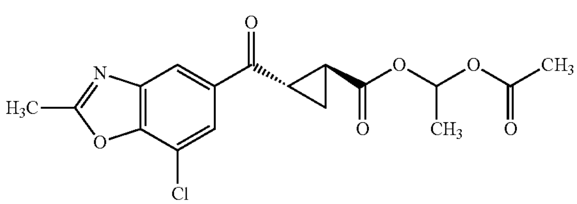 [SMILES: CC(=O)OC(C)OC(=O)[C@H]1C[C@@H]1C(=O)c1cc(Cl)c2oc(C)nc2c1] | 365.765 | 1-[(1S,2S)-2-(7-chloro-2-methyl-1,3-benzoxazole-5-carbonyl)cyclopropanecarbonyloxy]ethyl acetate |
| 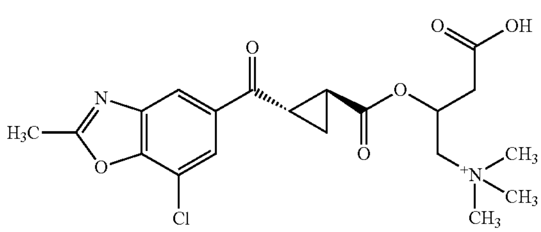 | 423.867 | {3-carboxy-2-[(1S,2S)-2-(7-chloro-2-methyl-1,3-benzoxazole-5-carbonyl)cyclopropanecarbonyloxy]propyl} trimethylazanium |
| 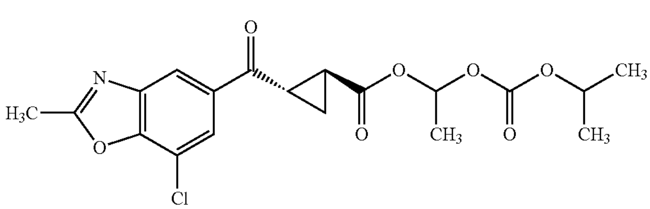 [SMILES: Cc1nc2cc(C(=O)[C@H]3C[C@@H]3C(=O)OC(C)OC(=O)OC(C)C)cc(Cl)c2o1] | 409.818 | 1-{[(propan-2-yloxy)carbonyl]oxy}ethyl (1S,2S)-2-(7-chloro-2-methyl-1,3-benzoxazole-5-carbonyl)cyclopropane-1-carboxylate |

| Structure | Mol. Weight | IUPAC Name |
|---|---|---|
| 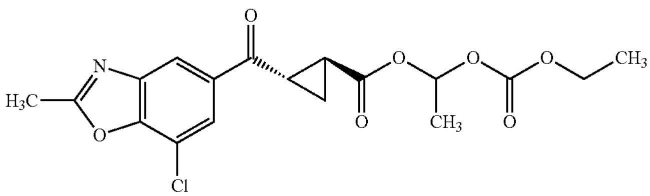 [SMILES: CCOC(=O)OC(C)OC(=O)[C@H]1C[C@@H]1C(=O)c1cc(Cl)c2oc(C)nc2c1] | 395.791 | 1-[(ethoxycarbonyl)oxy]ethyl (1S,2S)-2-(7-chloro-2-methyl-1,3-benzoxazole-5-carbonyl)cyclopropane-1-carboxylate |
| 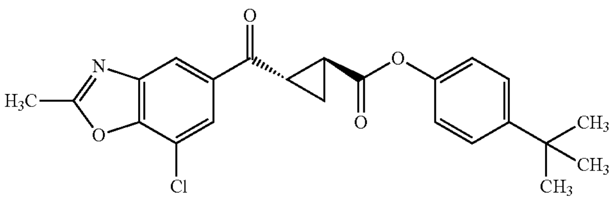 [SMILES: Cc1nc2cc(C(=O)[C@H]3C[C@@H]3C(=O)Oc3ccc(C(C)(C)C)cc3)cc(Cl)c2o1] | 411.878 | 4-tert-butylphenyl (1S,2S)-2-(7-chloro-2-methyl-1,3-benzoxazole-5-carbonyl)cyclopropane-1-carboxylate |
| | 335.782 | 2-methylpropyl (1S,2S)-2-(7-chloro-2-methyl-1,3-benzoxazole-5-carbonyl)cyclopropane-1-carboxylate |
| | 335.782 | butyl (1S,2S)-2-(7-chloro-2-methyl-1,3-benzoxazole-5-carbonyl)cyclopropane-1-carboxylate |
| 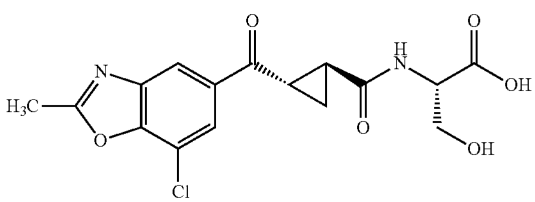 [SMILES: Cc1nc2cc(C(=O)[C@H]3C[C@@H]3C(=O)N[C@@H](CO)C(=O)O)cc(Cl)c2o1] | 366.753 | (2S)-2-{[(1S,2S)-2-(7-chloro-2-methyl-1,3-benzoxazole-5-carbonyl)cyclopropyl]formamido}-3-hydroxypropanoic acid |

Biology Example 1

A generalized procedure for monitoring L-Kynurenine (KYN) hydroxylation to form product 3-Hydroxy-Kynurenine (3OH-KYN) by LC/MS is described below. Product is quantified by multiple reaction monitoring using MS.

Key Reagents:
Compound: Stock concentrations: 10 mM in 100% DMSO
Cell line: CHO GST HIS KMO cell line, 1E4 cells/well/100 μl in 96 well cell plate
Substrate: L-Kynurenine (Sigma: Cat# K3750, stock concentration: 10 mM in 100 mM potassium phosphate buffer, pH 7.4)
Assay Conditions:
Medium: OptiMem (Reduced Serum Medium 1×, +L-Glutamine+HEPES−Phenol Red; GIBCO: Cat#11058)
Assay Volume: 200 μl
Plate Format: 96 well plate, transparent (Corning)
Read-Out: product (3OH-KYN) quantification using product specific MRM
Reader: LC/MS/MS Assay Protocol:
prepare serial dilution (factor 3) of compound in 100% DMSO (top concentration=6.67 mM, 100% DMSO) [8 points: 6.67 mM; 2.22 mM; 0.74 mM; 0.247 mM; 0.082 mM; 0.027 mM; 0.009 mM; 0.003 mM]
prepare 300-fold concentrated solution of each compound concentration (top concentration 22.22 μM, 0.3% DMSO) in OptiMem medium [22.2 μM; 7.41 μM; 2.47 μM; 0.82 μM; 0.27 μM; 0.09 μM; 0.03 μM; 0.01 μM]
prepare substrate (10 mM) at concentration of 1.1 mM in medium
medium of cell plate is drawed off
cells are washed with OptiMem (100 W/well) and thawed off again
assay mix: 90 μl OptiMem/well+90 μl compound/well of each concentration
[final compound top concentration: 10 μM; 0.15% DMSO]
[final compound bottom concentration: 0.004 μM; 0.15% DMSO]

pre-incubation: 30 min at 37° C.
add 20 µl/well of the 1.1 mM substrate solution (final assay concentration: 100 µM)
positive control: 200 µl OptiMem
negative control: 180 µl OptiMem+20 µl 1.1 mM substrate
incubate ~24 h at 37° C.
transfer 100 µl of each well in a transparent 96 well plate (Corning)
add 100 µl/well 10% trichloro acetic acid (TCA) in water
centrifugate plate for 3 min at 4000 rpm
detect product by LC/MS (injection of 50 µl/well; 2.5 fold overfill of the 20 µl sample loop)
Data analysis: $IC_{50}$'s are calculated using automated fitting algorithm (A+ Analysis).

Biology Example 2

A method of monitoring L-Kynurenine (KYN) hydroxylation to form product 3-Hydroxy-Kynurenine (3OH-KYN) by LC/MS is described below. Product is quantified by multiple reaction monitoring.
Key Reagents:
Compound: Stock concentrations: 10 mM in 100% DMSO
Enzyme: KMO enzyme prepared at Evotec via mitochondria isolation from CHO-GST HIS KMO cells
Substrate: L-Kynurenine (Sigma: Cat# K3750)
  [stock concentration: 10 mM in 100 mM potassium phosphate buffer, pH 7.4]
Assay Conditions:
Buffer: 100 mM potassium phosphate, pH 7.4, 200 µM NADPH, 0.4 U/ml G6P-DH (Glucose 6-phosphate dehydrogenase), 3 mM G6P (D-Glucose 6-phosphate)
Assay Volume: 40 µl
Plate Format: 384 well plate, transparent (Matrix)
Read-Out: product (3OH-KYN) quantification using product specific MRM
Reader: LC/MS/MS
Assay Protocol:
  prepare serial dilution (factor 3) of compound in 100% DMSO (top concentration=10 mM, 100% DMSO)
    [8 points: 10 mM; 3.33 mM; 1.11 mM; 0.37 mM; 0.12 mM; 0.04 mM; 0.0137 mM; 0.0045 mM, 0.0015 mM]
  prepare 3.33-fold concentrated solution of each compound concentration (top concentration 300 µM, 3% DMSO) in assay buffer
    [concentrations: 300 µM; 100 µM; 33.3 µM; 11.1 µM; 3.70 µM; 1.23 µM; 0.41 µM; 0.137 µM]
  prepare substrate (10 mM) at concentration of 1 mM in assay buffer
  assay mix: 4 µl compound/well of each concentration+24 µl assay buffer/well+8 µl KMO human enzyme+4 µl 1 mM substrate (final concentration=100 µM)
    [final compound top concentration: 30 µM; 0.3% DMSO]
    [final compound bottom concentration: 0.0137 µM; 0.3% DMSO]
  positive control: 4 µl 50 µM FCE28833 in assay buffer [0.5% DMSO] (final assay concentration=5 µM)+24 µl assay buffer/well+8 µl KMO human enzyme+4 µl 1 mM substrate (final concentration=100 µM)
  negative control: 28 µl assay buffer/well+8 µl KMO human enzyme+4 µl 1 mM substrate (final concentration=100 µM)
  incubate 400 min at RT
  add 40 µl/well 10% trichloro acetic acid in water to stop the assay and precipitate protein
  centrifuge plate for 3 min at 4000 rpm
  product detection by LC/MS (injection of 50 µl/well; 2.5 fold overfill of the 20 µl sample loop)
Data Analysis:
  $IC_{50}$'s are calculated using automated fitting algorithm (A+ Analysis).

Biology Example 3

A method of monitoring L-Kynurenine (KYN) hydroxylation to form 3-Hydroxy-Kynurenine (3OH-KYN) by LC/MS is described. Product is quantified by multiple reaction monitoring (MRM method).
Key Reagents:
Compound: Stock concentrations: 10 mM in 100% DMSO
Enzyme: KMO enzyme prepared at Evotec from mouse liver (4-6 weeks old) via mitochondria isolation as described in the literature
Substrate: L-Kynurenine (Sigma: Cat# K3750, stock concentration: 10 mM in 100 mM potassium phosphate buffer, pH 7.4)
Assay Conditions:
Buffer: 100 mM potassium phosphate, pH 7.4, 200 µM NADPH, 0.4 U/ml G6P-DH (Glucose 6-phosphate Dehydrogenase), 3 mM G6P (D-Glucose 6-phosphate)
Assay Volume: 40 µl
Plate Format: 384 well plate, transparent (Matrix)
Read-Out: product (3OH-KYN) quantification using product specific MRM
Reader: LC/MS/MS
Assay Protocol:
  prepare serial dilution (factor 3) of compound in 100% DMSO (top concentration=10 mM, 100% DMSO)
    [8 points: 10 mM; 3.33 mM; 1.11 mM; 0.37 mM; 0.12 mM; 0.04 mM; 0.0137 mM; 0.0045 mM, 0.0015 mM]
  prepare 3.33-fold concentrated solution of each compound concentration (top concentration 300 µM, 3% DMSO) in assay buffer
    [concentrations: 300 µM; 100 µM; 33.3 µM; 11.1 µM; 3.70 µM; 1.23 µM; 0.41 µM; 0.137 µM]
  prepare substrate (10 mM) at concentration of 1 mM in assay buffer
  assay mix: 4 µl compound/well of each concentration+24 µl assaybuffer/well+8 µl KMO mouse enzyme+4 µl 1 mM substrate (final concentration=100 µM)
    [final compound top concentration: 30 µM; 0.3% DMSO]
    [final compound bottom concentration: 0.0137 µM; 0.3% DMSO]
  positive control: 4 µl 50 µM FCE28833 in assay buffer, 0.5% DMSO [final assay concentration=5 µM]+24 µl assaybuffer/well+8 µl KMO mouse enzyme+4 µl 1 mM substrate [final concentration=100 µM]
  negative control: 28 µl assay buffer/well+8 µl KMO mouse enzyme+4 µl 1 mM substrate
    [final concentration=100 µM]
  incubate 40 min at RT
  add 40 µl/well 10% trichloro acetic acid in water to stop the assay and precipitate protein
  centrifuge plate for 3 min at 4000 rpm
  product detection by LC/MS (injection of 20 µl/well, 2 fold overfill of the 10 µl sample loop)
Data Analysis:
  $IC_{50}$'s are calculated using automated fitting algorithm (A+ Analysis).

Biology Example 4

Using the assay protocols substantially similar to those of Biology Example 3, the following compounds were tested.

| Structure | IUPAC Name | Percent Inhibition at 30 μM |
|---|---|---|
| 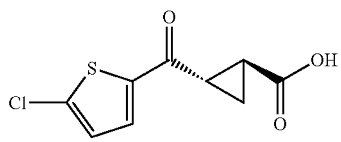 [SMILES: O=C(O)[C@H]1C[C@@H]1C(=O)c1ccc(Cl)s1] | (1S,2S)-2-[(5-Chlorothiophen-2-yl)carbonyl]cyclopropane-1-carboxylic acid | 100.7 |
| 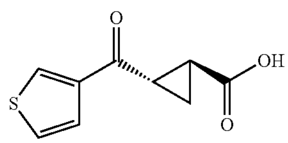 [SMILES: O=C(O)[C@H]1C[C@@H]1C(=O)c1ccsc1] | (1S,2S)-2-[(Thiophen-3-yl)carbonyl]cyclopropane-1-carboxylic acid | 83.2 |
| 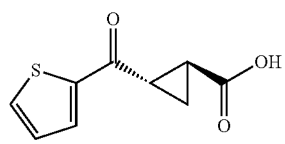 [SMILES: O=C(O)[C@H]1C[C@@H]1C(=O)c1cccs1] | (1S,2S)-2-[(Thiophen-2-yl)carbonyl]cyclopropane-1-carboxylic acid | 80.3 |
| 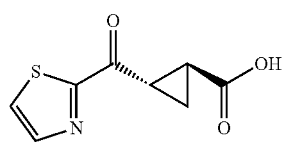 [SMILES: O=C(O)[C@H]1C[C@@H]1C(=O)c1nccs1] | (1S,2S)-2-[(1,3-Thiazol-2-yl)carbonyl]cyclopropane-1-carboxylic acid | 28.7 (at 10 uM) |
| 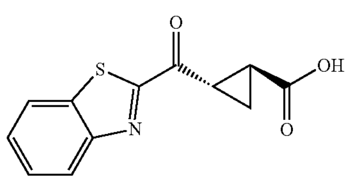 [SMILES: O=C(O)[C@H]1C[C@@H]1C(=O)c1nc2ccccc2s1] | (1S,2S)-2-[(1,3-Benzothiazol-2-yl)carbonyl]cyclopropane-1-carboxylic acid | 91.8 |
| 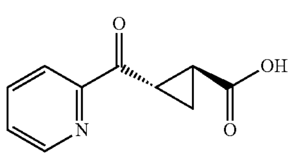 [SMILES: O=C(O)[C@H]1C[C@@H]1C(=O)c1ccccn1] | (1S,2S)-2-[(Pyridin-2-yl)carbonyl]cyclopropane-1-carboxylic acid | 45.6 |
| 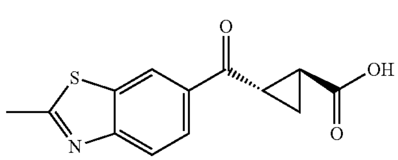 [SMILES: Cc1nc2ccc(C(=O)[C@H]3C[C@@H]3C(=O)O)cc2s1] | (1S,2S)-2-(2-methyl-1,3-benzothiazole-6-carbonyl)cyclopropane-1-carboxylic acid | 74.5 |
| 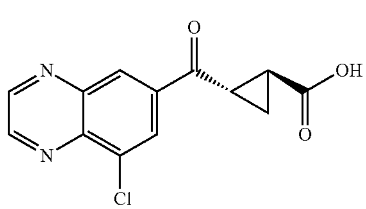 [SMILES: O=C(O)[C@H]1C[C@@H]1C(=O)c1cc(Cl)c2nccnc2c1] | (1S,2S)-2-(8-chloroquinoxaline-6-carbonyl)cyclopropane-1-carboxylic acid | 100.6 |

Table of compounds with inhibition information

| Table of compounds with inhibition information | | |
|---|---|---|
| Structure | IUPAC Name | Percent Inhibition at 30 μM |
| | (1S,2S)-2-(8-chloroquinoline-6-carbonyl)cyclopropane-1-carboxylic acid | 100.5 |
| 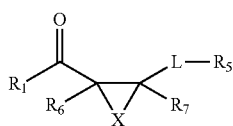 | (1S,2S)-2-(7-chloro-1-benzofuran-5-carbonyl)cyclopropane-1-carboxylic acid | 100.4 |

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed is:

1. A compound of Formula I

Formula I or a pharmaceutically acceptable salt or prodrug thereof, wherein
$R_1$ is 1,3-benzothiazol-2-yl, 2-methyl-1,3-benzothiazol-6-yl, 8-chloroquinoxalin-6-yl, 8-chloroquinolin-6-yl, 7-chloro-2-methyl-1-benzofuran-5-yl, 7-chloro-1-benzofuran-5-yl, 8-chloroisoquinolin-6-yl, 5-chloroquinazolin-7-yl, 8-chloroquinazolin-6-yl, 8-chlorocinnolin-6-yl, 4-chlorobenzo[d]oxazol-6-yl, 4-chloro-2-methylbenzo[d]oxazol-6-yl, 4-chloro-1H-benzo[d]imidazol-6-yl, 7-chlorobenzo[d]oxazol-5-yl, 7-chloro-2-methylbenzo[d]oxazol-5-yl, 7-chlorobenzo[d]thiazol-5-yl, 7-chloro-2-methylbenzo[d]thiazol-5-yl, 7-chloro-1H-indol-5-yl, 7-chloro-1H-indazol-5-yl, 7-chloro-1-methyl-1H-indazol-5-yl, 7-chlorobenzo[d]isoxazol-5-yl, 7-chloro-1-methyl-1H-indol-5-yl, or 7-chlorobenzofuran-5-yl;
X is —$CR_2R_3$—;
$R_2$ and $R_3$ are independently chosen from hydrogen, optionally substituted amino, hydroxyl, lower alkoxy, and optionally substituted lower alkyl;
L is —C(O)O—;
$R_5$ is hydrogen; and
$R_6$ and $R_7$ are independently chosen from hydrogen, halo, optionally substituted amino, hydroxyl, lower alkoxy, and optionally substituted lower alkyl.

2. The compound of claim 1, or a pharmaceutically acceptable salt or prodrug thereof, wherein $R_2$ is hydrogen, hydroxyl, lower alkoxy, amino optionally substituted with one or more alkyl groups, or lower alkyl optionally substituted with one or more groups independently chosen from halo, hydroxyl, lower alkoxy, and amino optionally substituted with one or more alkyl groups.

3. The compound of claim 2, or a pharmaceutically acceptable salt or prodrug thereof, wherein $R_2$ is hydrogen, amino, methylamino, dimethylamino, hydroxyl, methyl, methoxy, difluoromethyl, trifluoromethyl, hydroxymethyl, methoxymethyl, aminomethyl, (methylamino)methyl, or (dimethylamino)methyl.

4. The compound of claim 1, or a pharmaceutically acceptable salt or prodrug thereof, wherein $R_3$ is hydrogen or lower alkyl.

5. The compound of claim 4, or a pharmaceutically acceptable salt or prodrug thereof, wherein $R_3$ is hydrogen or methyl.

6. The compound of claim 1, or a pharmaceutically acceptable salt or prodrug thereof, wherein $R_2$ and $R_3$ are hydrogen.

7. The compound of claim 1, or a pharmaceutically acceptable salt or prodrug thereof, wherein $R_2$ is methyl and $R_3$ is hydrogen.

8. The compound of claim 1, or a pharmaceutically acceptable salt or prodrug thereof, wherein $R_2$ and $R_3$ are methyl.

9. The compound of claim 1, or a pharmaceutically acceptable salt or prodrug thereof, wherein $R_1$ is 7-chlorobenzofuran-5-yl, 7-chloro-2-methylbenzo[d]oxazol-5-yl, or 4-chlorobenzo[d]oxazol-6-yl.

10. The compound of claim 1, or a pharmaceutically acceptable salt or prodrug thereof, wherein $R_7$ is hydrogen, amino, methylamino, dimethylamino, aminomethyl, (methylamino)methyl, (dimethylamino)methyl, methoxymethyl, methyl, 1-aminoethyl, 1-methoxy-ethyl, methoxy, or halo.

11. The compound of claim 10, or a pharmaceutically acceptable salt or prodrug thereof, wherein $R_7$ is methyl.

12. The compound of claim 10, or a pharmaceutically acceptable salt or prodrug thereof, wherein $R_7$ is hydrogen.

13. The compound of claim 1, or a pharmaceutically acceptable salt or prodrug thereof, wherein $R_6$ is hydrogen, amino, methylamino, dimethylamino, aminomethyl, methylaminomethyl, (dimethylamino)methyl, or methyl.

14. The compound of claim 13, or a pharmaceutically acceptable salt or prodrug thereof, wherein $R_6$ is hydrogen.

15. A compound, or a pharmaceutically acceptable salt or prodrug thereof, selected from:
- (1S,2S)-2-(2-methyl-1,3-benzothiazole-6-carbonyl)cyclopropane-1-carboxylic acid,
- (1S,2S)-2-(7-chloro-1-benzofuran-5-carbonyl)cyclopropane-1-carboxylic acid,
- (1S,2S)-2-(7-chloro-2-methyl-1-benzofuran-5-carbonyl)cyclopropane-1-carboxylic acid,
- (1S,2S)-2-(8-chloroquinoline-6-carbonyl)cyclopropane-1-carboxylic acid,
- (1S,2S)-2-(8-chloroquinoxaline-6-carbonyl)cyclopropane-1-carboxylic acid,
- (1S,2S)-2-[(1,3-Benzothiazol-2-yl)carbonyl]cyclopropane-1-carboxylic acid,
- (1S,2S)-2-(8-chloroisoquinoline-6-carbonyl)cyclopropanecarboxylic acid,
- (1S,2S)-2-(5-chloroquinazoline-7-carbonyl)cyclopropanecarboxylic acid,
- (1S,2S)-2-(8-chloroquinazoline-6-carbonyl)cyclopropanecarboxylic acid,
- (1S,2S)-2-(8-chlorocinnoline-6-carbonyl)cyclopropanecarboxylic acid,
- (1S,2S)-2-(4-chlorobenzo[d]oxazole-6-carbonyl)cyclopropanecarboxylic acid,
- (1S,2S)-2-(4-chloro-2-methylbenzo[d]oxazole-6-carbonyl)cyclopropanecarboxylic acid,
- (1S,2S)-2-(4-chloro-1H-benzo[d]imidazole-6-carbonyl)cyclopropanecarboxylic acid,
- (1S,2S)-2-(7-chlorobenzo[d]oxazole-5-carbonyl)cyclopropanecarboxylic acid,
- (1S,2S)-2-(7-chloro-2-methylbenzo[d]oxazole-5-carbonyl)cyclopropanecarboxylic acid,
- (1S,2S)-2-(7-chlorobenzo[d]thiazole-5-carbonyl)cyclopropanecarboxylic acid,
- (1S,2S)-2-(7-chloro-2-methylbenzo[d]thiazole-5-carbonyl)cyclopropanecarboxylic acid,
- (1S,2S)-2-(7-chloro-1H-indole-5-carbonyl)cyclopropanecarboxylic acid,
- (1S,2S)-2-(7-chloro-1H-indazole-5-carbonyl)cyclopropanecarboxylic acid,
- (1S,2S)-2-(7-chloro-1-methyl-1H-indazole-5-carbonyl)cyclopropanecarboxylic acid,
- (1S,2S)-2-(7-chlorobenzo[d]isoxazole-5-carbonyl)cyclopropanecarboxylic acid,
- (1S,2S)-2-(7-chloro-1-methyl-1H-indole-5-carbonyl)cyclopropanecarboxylic acid,
- (1R,2S)-1-amino-2-(7-chlorobenzofuran-5-carbonyl)cyclopropanecarboxylic acid,
- (1R,2S)-2-(7-chlorobenzofuran-5-carbonyl)-1-(methylamino)cyclopropanecarboxylic acid,
- (1R,2S)-2-(7-chlorobenzofuran-5-carbonyl)-1-(dimethylamino)cyclopropanecarboxylic acid,
- (1S,2S)-1-(aminomethyl)-2-(7-chlorobenzofuran-5-carbonyl)cyclopropanecarboxylic acid,
- (1S,2S)-2-(7-chlorobenzofuran-5-carbonyl)-1-((methylamino)methyl)cyclopropanecarboxylic acid,
- (1S,2S)-2-(7-chlorobenzofuran-5-carbonyl)-1-((dimethylamino)methyl)cyclopropanecarboxylic acid,
- (1S,2S)-2-(7-chlorobenzofuran-5-carbonyl)-1-methylcyclopropanecarboxylic acid,
- (1R,2R)-2-(7-chlorobenzofuran-5-carbonyl)-1-fluorocyclopropanecarboxylic acid,
- (1R,2S)-2-(7-chlorobenzofuran-5-carbonyl)-1-methoxycyclopropanecarboxylic acid,
- (1S,2S)-2-(7-chlorobenzofuran-5-carbonyl)-1-(methoxymethyl)cyclopropanecarboxylic acid,
- (1R,3R)-2-amino-3-(7-chlorobenzofuran-5-carbonyl)cyclopropanecarboxylic acid,
- (1R,2R)-2-(7-chlorobenzofuran-5-carbonyl)-3-(methylamino)cyclopropanecarboxylic acid,
- (1R,2R)-2-(7-chlorobenzofuran-5-carbonyl)-3-(dimethylamino)cyclopropanecarboxylic acid,
- (1S,2S)-2-(7-chlorobenzofuran-5-carbonyl)-3-methylcyclopropanecarboxylic acid,
- (1R,3R)-3-(7-chlorobenzofuran-5-carbonyl)-2,2-dimethylcyclopropanecarboxylic acid,
- (1R,3R)-3-(7-chlorobenzofuran-5-carbonyl)-2-hydroxy-2-methylcyclopropanecarboxylic acid,
- (1R,3R)-3-(7-chlorobenzofuran-5-carbonyl)-2-(hydroxymethyl)-2-methylcyclopropanecarboxylic acid,
- (1R,3R)-3-(7-chlorobenzofuran-5-carbonyl)-2-(methoxymethyl)-2-methylcyclopropanecarboxylic acid,
- (1R,3R)-2-(aminomethyl)-3-(7-chlorobenzofuran-5-carbonyl)-2-methylcyclopropanecarboxylic acid,
- (1R,3R)-3-(7-chlorobenzofuran-5-carbonyl)-2-methyl-2-((methylamino)methyl)cyclopropanecarboxylic acid,
- (1R,3R)-2-amino-3-(7-chlorobenzofuran-5-carbonyl)-2-methylcyclopropanecarboxylic acid,
- (1R,3R)-3-(7-chlorobenzofuran-5-carbonyl)-2-methyl-2-(methylamino)cyclopropanecarboxylic acid,
- (1S,3S)-2-(aminomethyl)-3-(7-chlorobenzofuran-5-carbonyl)cyclopropanecarboxylic acid,
- (1S,2S)-2-(7-chlorobenzofuran-5-carbonyl)-3-((methylamino)methyl)cyclopropanecarboxylic acid,
- (1S,2S)-2-(7-chlorobenzofuran-5-carbonyl)-3-((dimethylamino)methyl)cyclopropanecarboxylic acid,
- (1S,2R)-2-amino-2-(7-chlorobenzofuran-5-carbonyl)cyclopropanecarboxylic acid,
- (1S,2R)-2-(7-chlorobenzofuran-5-carbonyl)-2-(methylamino)cyclopropanecarboxylic acid,
- (1S,2R)-2-(7-chlorobenzofuran-5-carbonyl)-2-(dimethylamino)cyclopropanecarboxylic acid,
- (1S,2S)-2-(aminomethyl)-2-(7-chlorobenzofuran-5-carbonyl)cyclopropanecarboxylic acid,
- (1S,2S)-2-(7-chlorobenzofuran-5-carbonyl)-2-((methylamino)methyl)cyclopropanecarboxylic acid,
- (1S,2S)-2-(7-chlorobenzofuran-5-carbonyl)-2-((dimethylamino)methyl)cyclopropanecarboxylic acid, and
- (1S,2S)-2-(7-chlorobenzofuran-5-carbonyl)-2-methylcyclopropanecarboxylic acid.

16. A pharmaceutical composition comprising at least one compound of claim 1, or a pharmaceutically acceptable salt or prodrug thereof, and at least one pharmaceutically acceptable excipient.

* * * * *

UNITED STATES PATENT AND TRADEMARK OFFICE
CERTIFICATE OF CORRECTION

PATENT NO. : 9,884,853 B2
APPLICATION NO. : 14/392304
DATED : February 6, 2018
INVENTOR(S) : Leticia M. Toledo-Sherman et al.

It is certified that error appears in the above-identified patent and that said Letters Patent is hereby corrected as shown below:

On the Title Page

Column 2, Line 14 In the Abstract (item (57)), please replace "Also described are methods of treatment include administering at least one compound" with --Also described are methods of treatment including administering at least one compound--.

In the Claims

In Claim 1, Column 91, Lines 52-53, please replace "7-chloro-2-methyl-1-benzofuran-5-yl, 7-chloro-1-benzofuran-5-yl, 8-chloroisoquinolin-6-yl," with --7-chloro-2-methyl-1-benzofuran-5-yl, 8-chloroisoquinolin-6-yl,--.

Signed and Sealed this
Seventeenth Day of October, 2023

Katherine Kelly Vidal
*Director of the United States Patent and Trademark Office*